US012807610B2

(12) United States Patent
Da Silva Pereira De Sousa et al.

(10) Patent No.: US 12,807,610 B2
(45) Date of Patent: Nov. 24, 2026

(54) PYRAZINO [1,2-b]QUINAZOLINE-3,6-DIONES DERIVATIVES, THEIR PRODUCTION AND USES THEREOF

(71) Applicants: CIIMAR—CENTRO INTERDISCIPLINAR DE INVESTIGAÇÃO MARINHA E AMBIENTAL, Matosinhos (PT); UNIVERSIDADE DO PORTO, Oporto (PT); Universidade Nova De Lisboa, Lisbon (PT)

(72) Inventors: Maria Emilia Da Silva Pereira De Sousa, Oporto (PT); Solida Long, Oporto (PT); Madalena Maria De Magalhaes Pinto, Oporto (PT); Diana Resende, Oporto (PT); Anake Kijjoa, Oporto (PT); Paulo Manuel Rodrigues Martins Da Costa, Oporto (PT); Joana Manuela Machado Freitas Da Silva, Oporto (PT); Fatima Nogueira, Lisbon (PT)

(73) Assignees: CIIMAR—CENTRO INTERDISCIPLINAR DE INVESTIGAÇÃO MARINHA E AMBIENTAL, Matosinhos (PT); UNIVERSIDADE DO PORTO, Oporto (PT); UNIVERSIDADE NOVA DE LISBOA, Lisbon (PT)

( * ) Notice: Subject to any disclaimer, the term of this patent is extended or adjusted under 35 U.S.C. 154(b) by 1302 days.

(21) Appl. No.: 17/632,648

(22) PCT Filed: Aug. 20, 2020

(86) PCT No.: PCT/IB2020/057831
§ 371 (c)(1),
(2) Date: Feb. 3, 2022

(87) PCT Pub. No.: WO2021/033159
PCT Pub. Date: Feb. 25, 2021

(65) Prior Publication Data

US 2022/0274987 A1 Sep. 1, 2022

(30) Foreign Application Priority Data

Aug. 20, 2019 (PT) ........................................ 115744

(51) Int. Cl.

| | |
|---|---|
| ***C07D 471/14*** | (2006.01) |
| ***A61K 45/06*** | (2006.01) |
| ***C07D 487/04*** | (2006.01) |

(52) U.S. Cl.
CPC ............ *C07D 471/14* (2013.01); *A61K 45/06* (2013.01); *C07D 487/04* (2013.01)

(58) Field of Classification Search
CPC .................................................... C07D 471/14
See application file for complete search history.

(56) References Cited

FOREIGN PATENT DOCUMENTS

WO 00/18769 A2 4/2000

OTHER PUBLICATIONS

Bastos et. al. (Microbiological Research 159 (2004) 317-322)) (Year: 2004).*
Gansen et. al. (J. Org. Chem. 2000, 65, 1022-1030) (Year: 2000).*
Diana I.S. P. Resende et al., "Chemistry of the fumiquinazolines and structurally related alkaloids", Natural Product Reports, Jan. 2019, pp. 7-34.
Lucinda J. Bessa et al., "Neofiscalin A and fiscalin C are potential novel indole alkaloid alternatives for the treatment of multidrug-resistant Gram-positive bacterial infections", FEMS Microbiology Letters Advance Access published Jun. 2016. 16 pages.
Solida Long et al., "Antitumor Activity of Quinazolinone Alkaloids Inspired by Marine Natural Products", Marine Drugs, Jul. 2018. 18 pages.
Solida Long et al., "Synthesis of New Proteomimetic Quinazolinone Alkaloids and Evaluation of Their Neuroprotective and Antitumor Effects", Molecules, Feb. 2019. 17 pages.
Francisco Javier Gamo et al., "Thousands of chemical starting points for antimalarial lead identification", Nature, vol. 465, May 2010, p. 305-310.
Lijuan Liao, "Alkaloidal Metabolites from a Marine-Derived *Aspergillus* sp. Fungus", Journal of Natural Products, Jan. 2015, pp. 349-354.
Lijuan Liao et al., Supporting Information, "Alkaloidal Metabolites from a Marine-Derived *Aspergillus* sp. Fungus" Jan. 2015. 36 pages.
Marley Garcia Silva et al., "Antibacterial activity from *Penicillium corylophilum* Dierckx", Microbiological Research, Jun. 2004, pp. 317-322.
Xioa-Fei Shang et al., "Biologically active quinoline and quinazoline alkaloids part I", Medicinal Research Reviews, Sep. 2017.

* cited by examiner

*Primary Examiner* — John S Kenyon
*Assistant Examiner* — Rehana Ismail
(74) *Attorney, Agent, or Firm* — Leason Ellis LLP

(57) ABSTRACT

The present disclosure relates to pyrazino [1,2-b]quinazoline-3,6-diones compounds, in particular it relates to pyrazino [1,2-b]quinazoline-3,6-diones compounds having antibacterial activity and/or antimalarial activity.

17 Claims, 7 Drawing Sheets

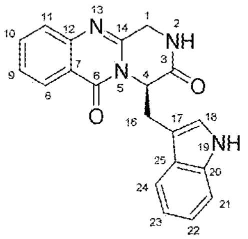
1, glyantrypine
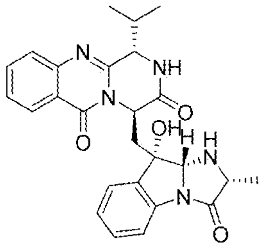
2, neofiscalin A
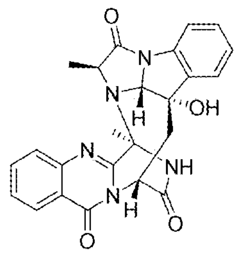
3, 2'-*epi*-fumiquinazoline D
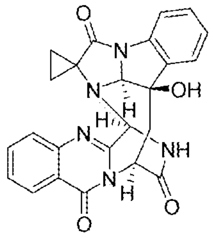
4, cottoquinazoline D
Fig. 1
Antimalarial drugs
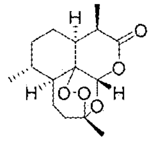
5. Artemisinin
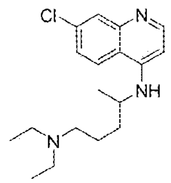
6. Chloroquine
Target compounds
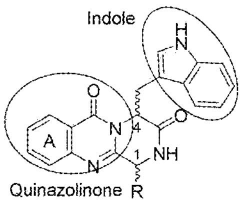
**Pyrazino[2,1-*b*]quinazoline--3,6-dione indole alkaloid**
Antimalarial lead drug candidates
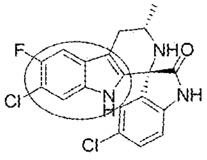
7. Spiroindolone
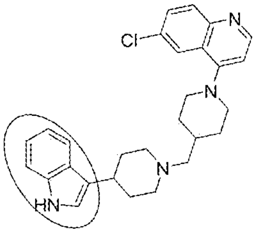
8. TCMDC-134281
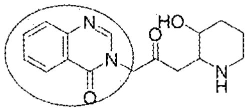
9.Febrifugine
Fig. 2

First modification

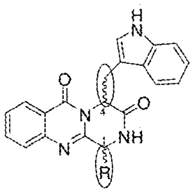

10, R = *i*-Pr, (1*S*, 4*S*)
11, R = *i*-Pr, (1*R*, 4*S*)
12, R = *i*-Pr, (1*S*, 4*R*)
13, R = *i*-Pr, (1*R*, 4*R*)
14, R = *i*-Bu, (1*S*, 4*S*)
15, R = *i*-Bu, (1*R*, 4*S*)
16, R = *i*-Bu, (1*S*, 4*R*)
17, R = *i*-Bu, (1*R*, 4*R*)

Second modification

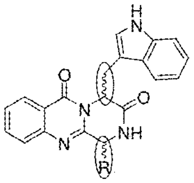

18, R = *s*-Bu, (1*R*, 4*S*)
19, R = *s*-Bu, (1*S*, 4*R*)
20, R = $(CH_2)_2SCH_3$, (1*R*, 4*S*)
21, R = $(CH_2)_2SCH_3$, (1*S*, 4*R*)
22, R = $CH_2C_6H_4OCH_2C_6H_5$, (1*S*, 4*S*)
23, R = $CH_2C_6H_4OCH_2C_6H_5$, (1*R*, 4*S*)
24, R = $CH_2C_6H_4OH$, (1*S*, 4*S*)
25, R = $CH_2C_6H_4OH$, (1*R*, 4*S*)
26, R = $CH_3$ (1*R*, 1*R*)

Third modification

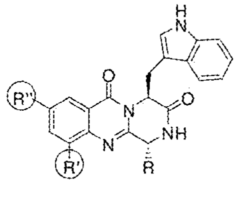

27, R = *i*-Pr, R' = Cl, R'' = H, (1*S*, 4*R*)
28, R = *i*-Bu, R' = Cl, R'' = H, (1*S*, 4*R*)
29, R = *s*-Bu, R' = Cl, R'' = H, (1*S*, 4*R*)
30, R = *i*-Pr, R' = R'' = Cl (1*S*, 4*R*)
31, R = *i*-Bu, R' = R'' = Cl, (1*S*, 4*R*)
32, R = *s*-Bu, R' = R'' = Cl, (1*S*, 4*R*)
33, R = *i*-Pr, R' = I, R'' = H, (1*S*, 4*R*)
34, R = *i*-Pr, R' = Br, R'' = H, (1*S*, 4*R*)
35, R = *i*-Bu, R' = I, R'' = H, (1*S*, 4*R*)
36, R = *i*-Bu, R' = Br, R'' = H, (1*S*, 4*R*)
37, R = *i*-Bu, R' = R'' = I, (1*S*, 4*R*)
38, R= $CH_2C_6H_4OCH_2C_6H_5$, R' =R'' =Cl

Fourth modification

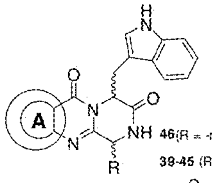

46(R = -methylenindole)
39-45 (R = *i*-Bu)

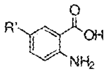

39, R = OH
40, R = Me
41, R = OMe

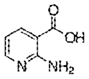

43

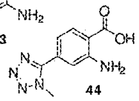

44

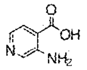

42

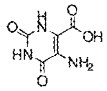

45

Fig. 3

*Structure-actiity relationship*

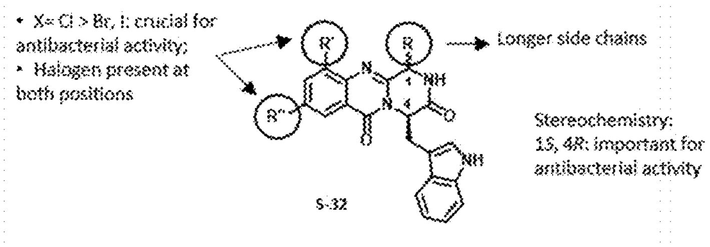

Fig. 4

PYRAZINO [1,2-b]QUINAZOLINE-3,6-DIONES DERIVATIVES, THEIR PRODUCTION AND USES THEREOF

CROSS-REFERENCE TO RELATED APPLICATIONS

This application is a U.S. National Stage Application under 35 U.S.C. § 371 of International Patent Application No. PCT/IB2020/057831, filed Aug. 20, 2020, which claims priority to Portugal Patent Application No. 115744, filed Aug. 20, 2019, the contents of which are each hereby incorporated by reference in their respective entireties.

TECHNICAL FIELD

The present disclosure relates to pyrazino [1,2-b]quinazoline-3,5-diones compounds, in particular it relates to pyrazino [1,2-b]quinazoline-3,6-diones compounds having antibacterial activity and/or antimalarial activity.

BACKGROUND

Infectious diseases caused by microorganisms stand as a major threat to public health. Since antibiotics were first introduced as medicines, these drugs have been used to prevent or treat infections in several applications. Nonetheless, antibacterial resistance has increased dramatically, becoming an emergency in healthcare during the last 40 years. Among 50 emerging infectious agents that have been identified, 10% have developed resistance to multiple drugs including antibiotics such as vancomycin, methicillin, carbapenems, and cephalosporins. Despite enormous efforts, the number of therapeutically useful compounds that aim for circumventing the resistance is continuously decreasing and no truly novel class of compounds has been introduced into therapy, causing the world to face the "post-antibiotic era". In order to stop the clinical consequences of the development and spread of antimicrobial resistance both the preservation of current antimicrobials through their appropriate use, as well as the discovery and development of new agents are mandatory.

Malaria represents a major threat to the public health worldwide, with over 219 million clinical cases in 2017 with 435 thousand of deaths. Though the number of cases has shown a decrease since 2010, evidences of slower *Plasmodium falciparum* parasite clearance have appeared in some countries in Southeast Asia especially at Greater Mekong Subregion (GMS) including Lao PDR, Thailand, Cambodia, Myanmar, and Vietnam. These represent a serious threat to global malaria control and eradication. The frontline therapies for the treatment of symptomatic malaria are artemisinin (5) combination therapies (ACTs) for *P. falciparum* infections and in the case of infections with *P. vivax*, chloroquine (CQ, 6) or ACTs are usually employed. This evidence, along with widespread resistance to other historical antimalarials, highlights the need to identify new chemical diversity, ideally with novel antimalarial modes of action.

Several reports emphasized the discovery of new sophisticated antimicrobials from marine sources as a promising strategy to overcome the ever-increasing drug-resistant infectious diseases. In the last years, fungal alkaloids containing an indolomethyl pyrazino[1,2-b] quinazoline-3,6-dione scaffold were isolated from marine organisms and presented very interesting antimicrobial activities (1). For instance, glyantypine (1) isolated from *Cladosporium* sp. PJX-41, exhibited moderate inhibitory activity against bacteria *Vibrio harvevi* (MIC=32 μg/mL) and neofiscalin A (2) found in *Neosartorya siamensis* KUFC 6349 exhibited a potent antibacterial activity against *Staphylococcus aureus* and *Enterococcus faecalis* (MIC=8 μg/mL) [2].

Strategies used for the development of novel antimalarial drugs include the discovery of new active molecules from natural products, repurposing of commercially available drugs, development of hybrid compounds, and rational drug design with molecular modifications of existing antimalarial and hits. The malarial chemotherapy has always been successfully influenced by natural products and nature is still an important source of antimalarial drugs. Recently, the analysis of Tres Cantos Antimalarial Set (TCAMS) suggested that indole-based antimalarials are the key core for the development of the next generation of antimalarial drugs since the indole scaffold is known as an important moiety present in several lead drug candidates with new mechanisms of action, such as the spiroindolone (7), febrifugine (9), and aminoindole derivatives. For example, TCMDC-134281 (8) exhibited very potent antiplasmodial properties against *P. falciparum* 3D7 strain ($EC_{50}$=34 nM). However, although TCMDC-134281 showed no significant cytotoxicity against human HepG2 hepatoma cell line ($EC_{50}$>10 μM), the presence of the 4-aminoquinolyl moiety (an essential pharmacophore of CQ) might be responsible for its cross-resistance with CQ (6) and poor-drug-like properties [5].

General Description

The present disclosure relates to four possible approaches to obtain indole-containing pyrazino[2,1-b]quinazoline-3,6-diones comprising a subclass of alkaloids mostly isolated from marine and terrestrial sources. These structurally unique alkaloids contain simultaneously a quinazoline core which can be found in the structure of the natural febrifugine (9) and an indole moiety commonly found in several drug lead candidates such as spiroindolone (7) and TCMDC-134281 (8). This hybrid structure comprises a quinazoline core and an indole core such that the observed inhibitory growth of MRSA may be observed and cross-resistance with CQ and ACTs may be overcome.

The first approach is based on the synthesis of enantiomeric pairs of two members of this quinazolinone family (structural modifications at C-1 and C-4 stereochemistry), including the marine-derived alkaloid fiscalin B (7A).

The second approach is based on the synthesis of other derivatives of these natural alkaloids, but with modification of the C-1 side chain and stereochemistry, by using different amino acids.

The third approach is based on the synthesis of indolomethyl pyrazino[1,2-b]quinazoline-3,6-dione analogs: the introduction of halogen atoms in the aromatic ring of the anthranilic acid (Ant).

The fourth approach is based on the synthesis of ring A variations on the pyrazino[2,1-b]quinazoline-3,6-dione scaffold or with an additional indole moiety.

The present disclosure relates to a compound of formula I

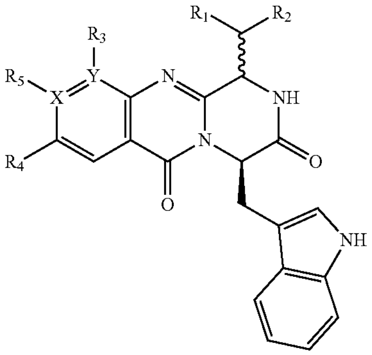

wherein $R^1$, $R^2$, $R^3$, $R^4$, $R^5$, X and Y are independently selected from each other;

$R^1$ and $R^2$ are selected from H or $CH_3$ or $CH(CH_3)_2$ or $CH_2CH_3$, $R^3$ and $R^4$ are selected from H or Cl or Br or I or F or OH or $OCH_3$, $R^5$ is H or

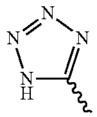

, and

X and Y are selected from N or C;

or a pharmaceutically acceptable salt, or ester or solvate, thereof, provided that when X and Y are C then $R^4$ is different from H; or when X and Y are C then $R^4$ is H and $R^5$ is

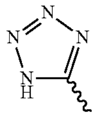

;

or when X is N then $R^5$ is absent or when Y is N then $R^3$ is absent.

In an embodiment, X and Y may be C.

In an embodiment, $R^1$ may be H or $CH_3$.

In an embodiment, $R^2$ may be $CH_3$ or $CH(CH_3)_2$ or $CH_2CH_3$.

In an embodiment, $R^3$ may be H or Cl or I, preferably $R^3$ may be H or Cl.

In as embodiment, $R^4$ may be Cl or I, preferably $R^4$ may be Cl.

In an embodiment, $R^5$ may be H.

In an embodiment, the compound may be

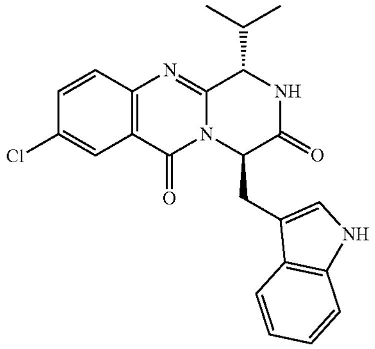

or

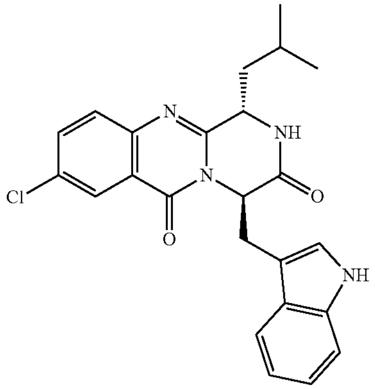

or

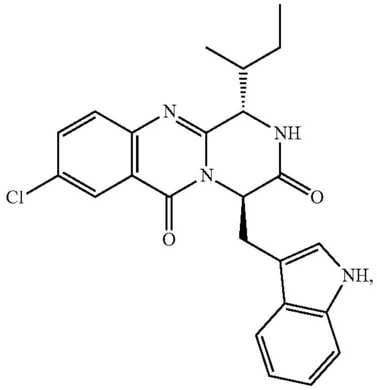

preferably the compound may be

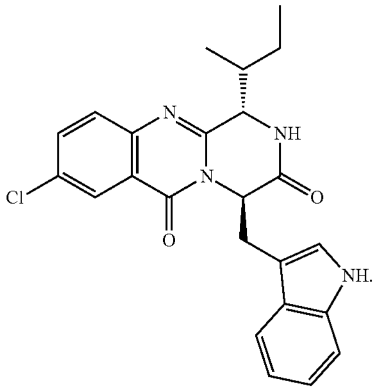 [SMILES: CCC(C)[C@@H]1NC(=O)[C@@H](Cc2c[nH]c3ccccc23)n2c1nc1ccc(Cl)cc1c2=O]

In an embodiment, the compound may be
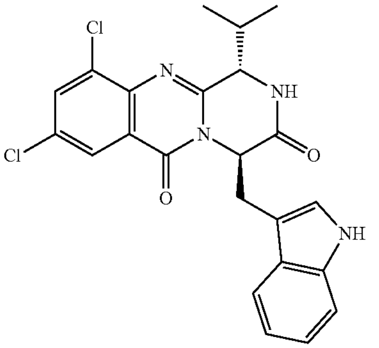
or,
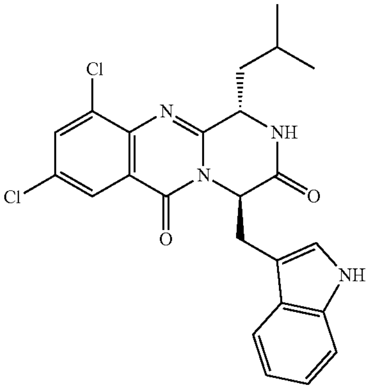
or,
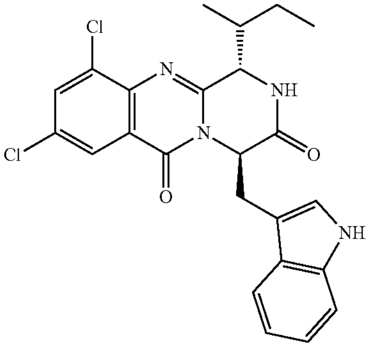
or,
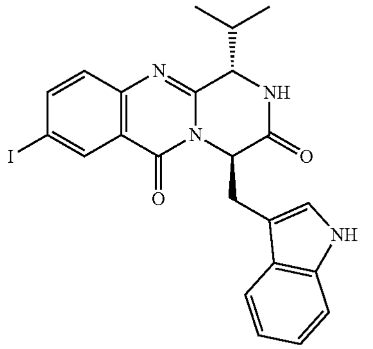
or,
-continued
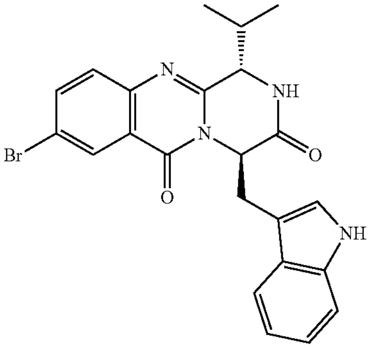
or,
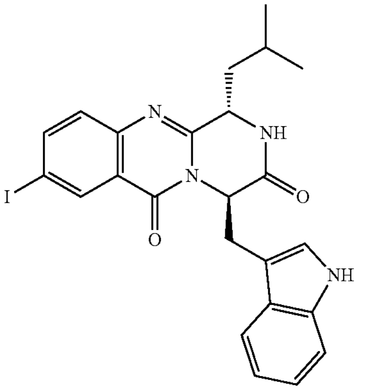
or,
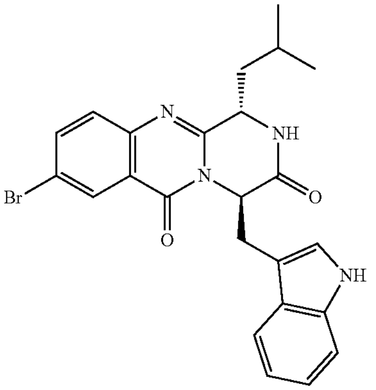
or,
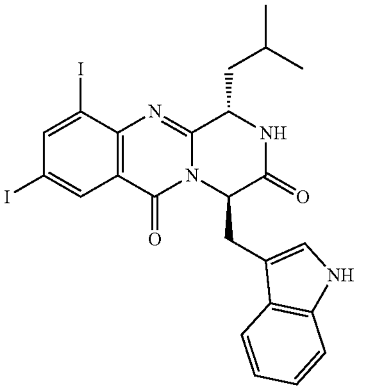
or, -continued
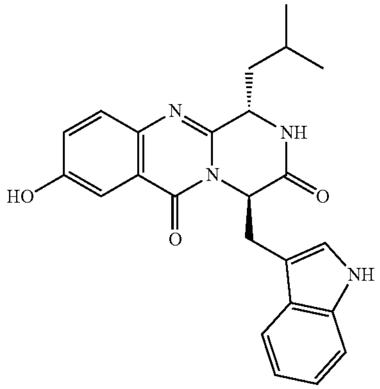
or,
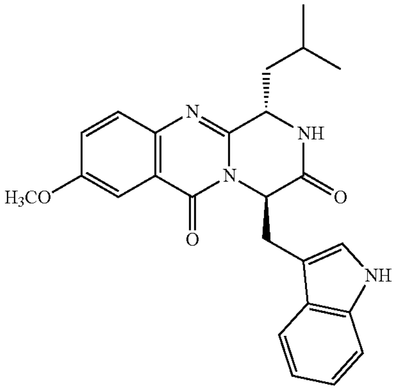
or,
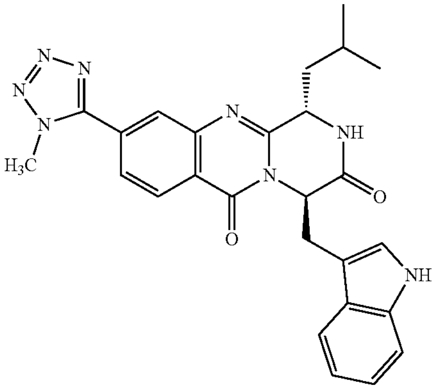
or,
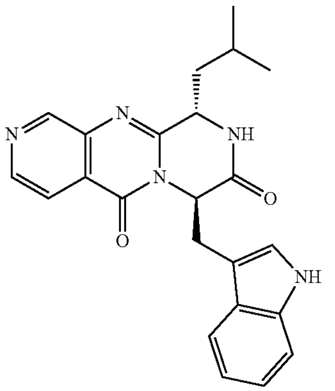
or,
-continued
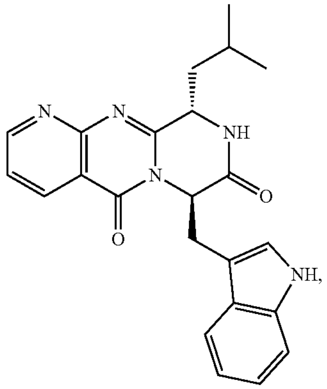
preferably the compound may be
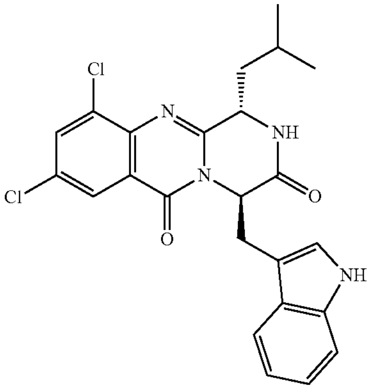
or
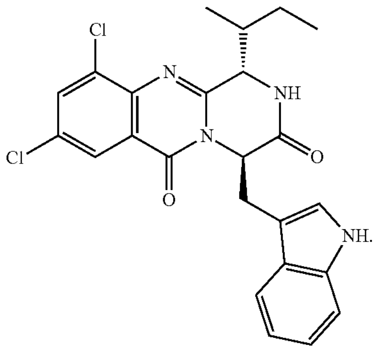
The present disclosure also relates to a compound for use in medicine. Preferably, the compound of formula I is

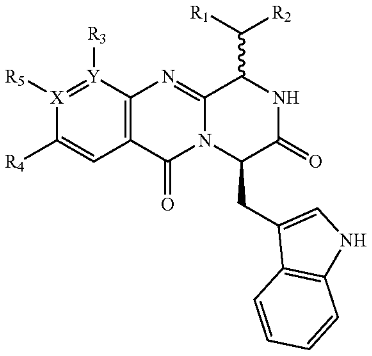

wherein $R^1$, $R^2$, $R^3$, $R^4$, $R^5$, X and Y are independently selected from each other;

$R^1$ and $R^2$ are selected from H or $CH_3$ or $CH(CH_3)_2$ or $CH_2CH_3$, $R^3$ and $R^4$ are selected from H or Cl or Br or I or F or OH or $OCH_3$, $R^5$ is H or

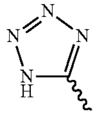
, and

X and Y are selected from N or C;

or a pharmaceutically acceptable salt, or ester or solvate thereof, provided that when X is N then $R^5$ is absent or when Y is N then $R^3$ is absent for use in the treatment or prevention of bacterial infections and/or for use in the treatment or prevention of malaria.

In an embodiment, the compounds may be selected from

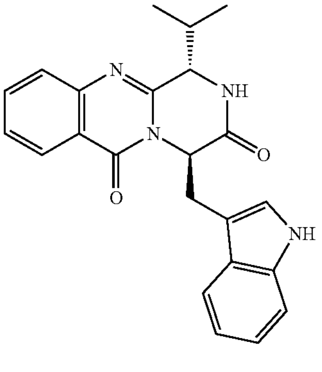
or,

-continued

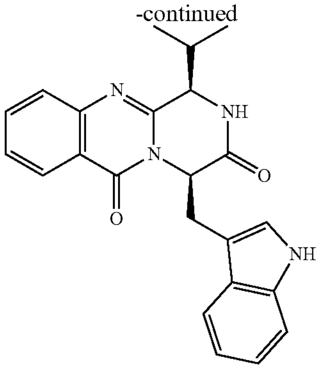
or,

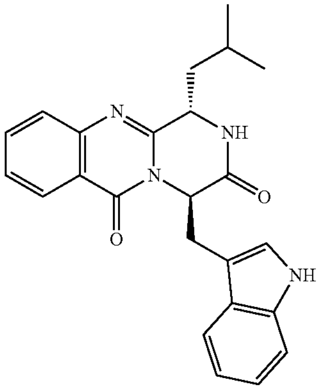
or,

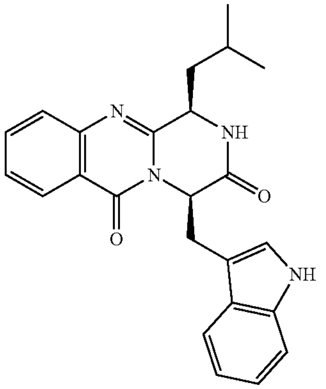
or,

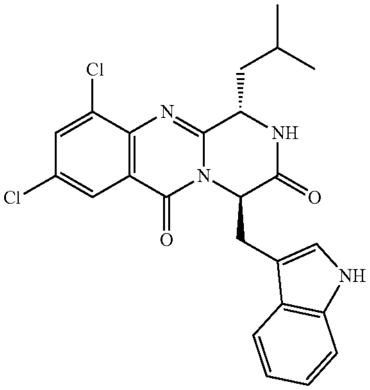 [SMILES: CC(C)C[C@@H]1NC(=O)[C@@H](Cc2c[nH]c3ccccc23)n2c1nc1c(Cl)cc(Cl)cc1c2=O]

and it may be for use in the treatment or prevention of malaria.

In an embodiment, any of the compounds herein disclosed may be for use in the treatment of Gram-positive bacterial infections, preferably caused by *Staphylococcus* spp. and/or *Enterococcus* spp., more preferably caused by *Staphylococcus aureus* and/or *Enterococcus faecalis*.

In an embodiment, any of the compounds herein disclosed may be for use in the treatment of bacterial infections, preferably caused by *Staphylococcus aureus* and *Enterococcus faecalis*, wherein the compound may be

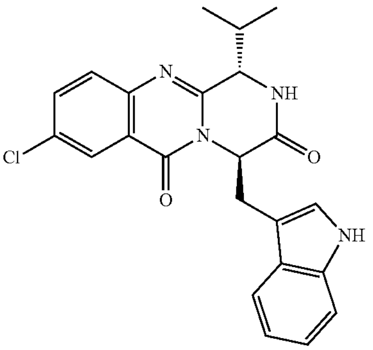

or,

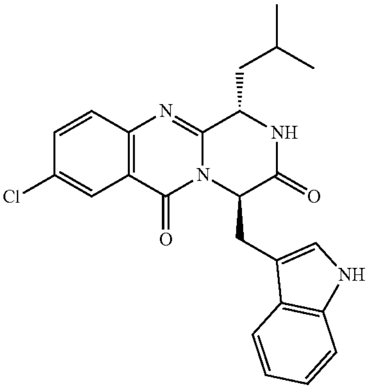

or,

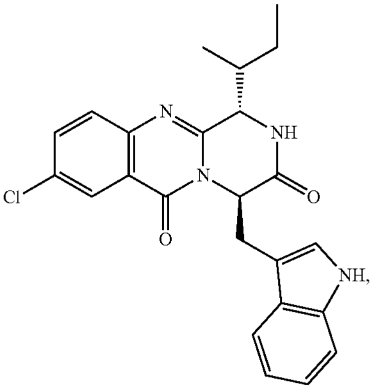

preferably wherein the compound may be

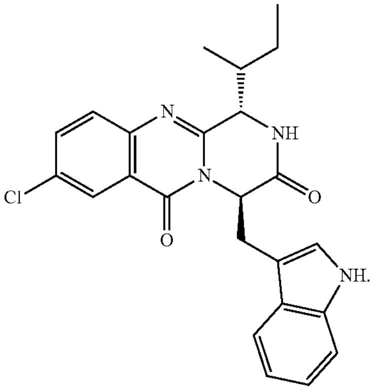 [SMILES: CCC(C)[C@@H]1NC(=O)[C@@H](Cc2c[nH]c3ccccc23)n2c1nc1ccc(Cl)cc1c2=O]

In embodiment, any of the compounds herein disclosed may be for use in the treatment of bacterial infections, preferably caused by *Staphylococcus aureus*, wherein the compound may be

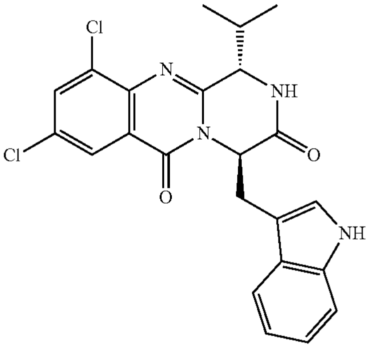

or,

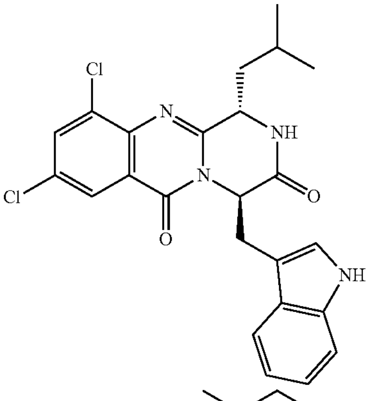

or,

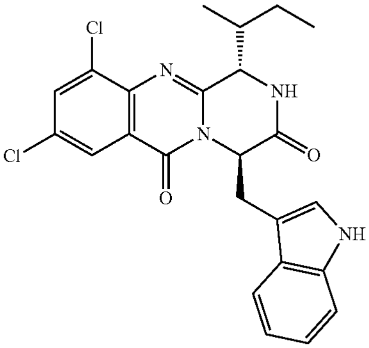

or,

-continued

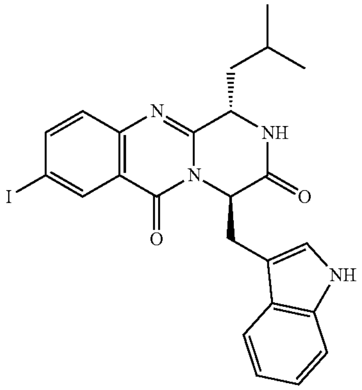

or,

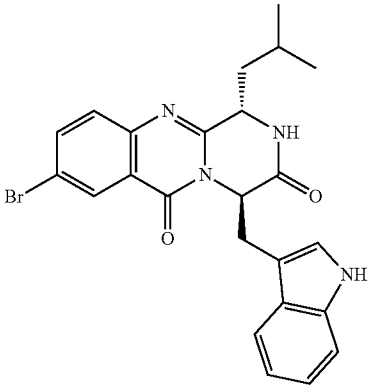

or,

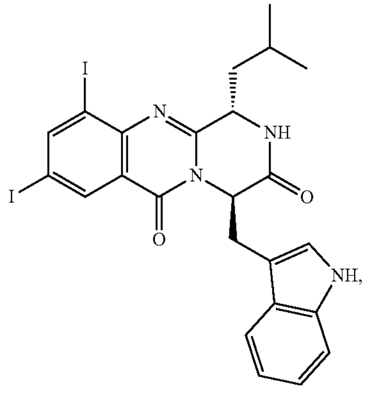

preferably wherein the compound may be

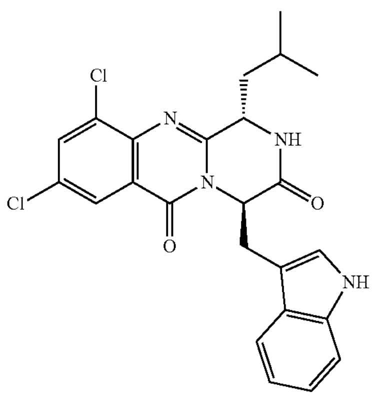

or

-continued

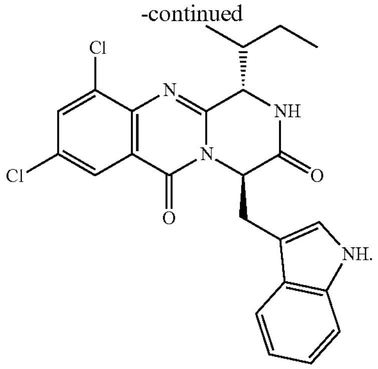

The present disclosure also relates to a composition comprising any of the compounds herein disclosed or composition for use, wherein any of the compounds herein disclosed is in a therapeutically effective amount and a pharmaceutically acceptable excipient.

In an embodiment, the above-mentioned composition may further comprise an antibiotic preferably wherein the antibiotic is a fluoroquinolone, preferably selected from ciprofloxacin, norfloxacin, pefloxacin, enofloxacin, ofloxacin, levofloxacin, moxifloxacin, or mixtures thereof.

BRIEF DESCRIPTION OF THE DRAWINGS

The following figures provide preferred embodiments for the present disclosure and should not be seen as limiting the scope of the disclosure.

FIG. 1. Examples of marine antimicrobials.

FIG. 2. Current antimalarial drugs 5 and 6, indole containing antimalarial compounds 7 and 8, natural antimalarial compound 9, and the scaffold of the target compounds, indole-containing pyrazino[2,1-b]quinazoline-3,6-dione.

FIG. 3. Structures of the third and fourth approaches of indole-containing pyrazino[2,1-b]quinazoline-3,6-diones synthesized.

FIG. 4. Structure-activity relationship for antibacterial activity of the library of quinazolinones 10-37.

DETAILED DESCRIPTION

Figure 5:
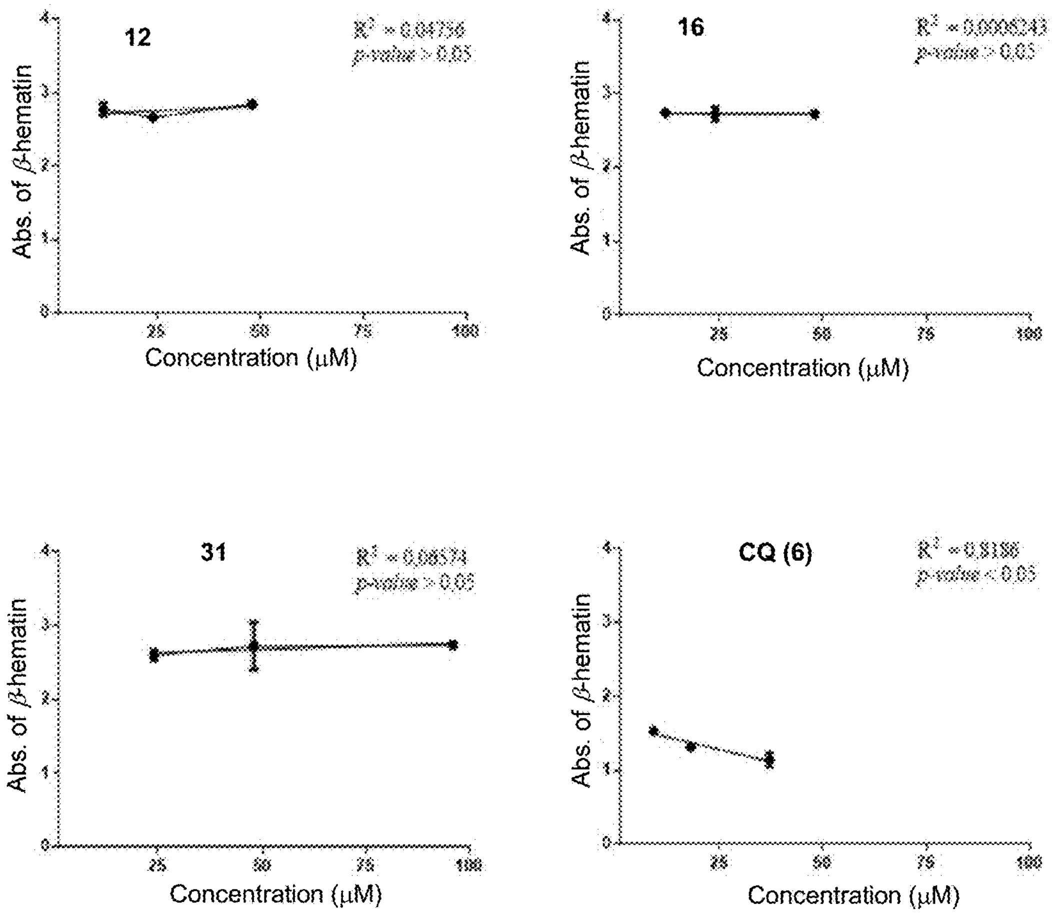
FIG. 5. The inhibition of polimerization of hemozoin in vitro of compound 12, 16, 31, and CQ (6). The error bars represent a mean±SD.

The present disclosure relates to antibacterial activity and/or to antimalarial activity of the compounds herein disclosed.

The compounds herein disclosed are synthetized using the approaches (1st, 2nd, 3rd and 4th approaches) summarized in FIG. 3.

The chemistry of compounds of the 1st approach (compounds 10-17) and 2nd approach (compounds 19, 21, 23, 25 and 26) is described in references 3 and 4. It was, however, surprisingly found that compounds of the 1st and 2nd approaches may nave antimalarial activity, as it will be described below.

Chemistry for the 3rd approach. The eleven new indolomethyl pyrazino[1,2-b]quinazoline-3,6-dione derivatives of the third approach were synthesized by a previously described approach using a microwave assisted multicomponent polycondensation of amino acids (Table 1). The coupling of halogenated commercial anthranilic acids (47) to N-protected L-α-amino acids (48), and further dehydrative cyclization using triphenyl phosphite [$(PhO)_3P$], generated the intermediates benzoxazin-4-ones 49 which, followed by the addition of D-tryptophan methyl ester (50) under microwave irradiation, furnished the desirable final products 27-37 (2-14% yield) with partial epimerization (Table 1). Using this methodology only anti isomers were produced (1S, 4R) and the different side chains at C-1 were

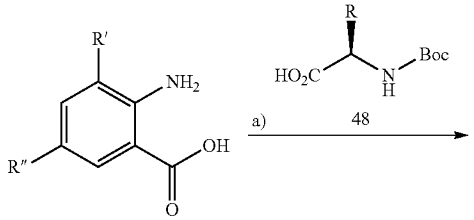

47

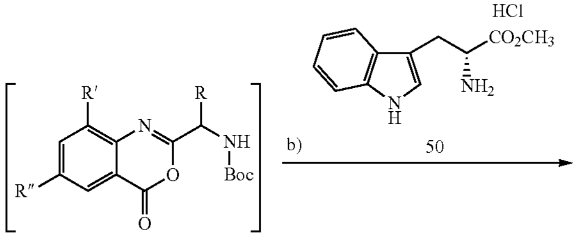

49

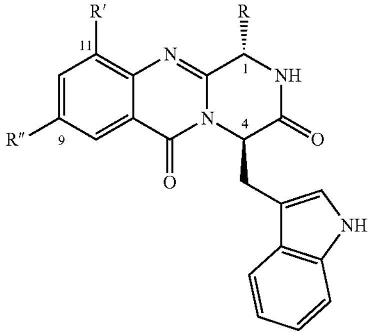

27-37

TABLE 1

| Synthesis of halogenated quinazolinone derivatives 27-37 [a] | | | | | | | |
|---|---|---|---|---|---|---|---|
| Compound | R | R' | R" | Yield (%) | [α]D[b] | e.r.[c] | %[d] |
| 27 | i-Pr | Cl | H | 5 | −273 | 56 (27a):44 (27b) | 92 |
| 28 | i-Bu | Cl | H | 3 | +154 | 44 (28a):56 (28b) | 99 |
| 29 | s-Bu | Cl | H | 2 | +130 | 46:54 | 93 |
| 30 | i-Pr | Cl | Cl | 5 | +140 | 43:57 | 90 |
| 31 | i-Bu | Cl | Cl | 4.5 | −169 | 60 (31a):40 (31b) | >99 |
| 32 | s-Bu | Cl | Cl | 2.6 | −264 | 71:29 | >99 |
| 33 | i-Pr | I | H | 4.1 | −175 | 51:49 | 95 |
| 34 | i-Pr | Br | H | 1.2 | −170 | 50:50 | 95 |
| 35 | i-Bu | I | H | 11.8 | −165 | 51:49 | 98 |
| 36 | i-Bu | Br | H | 13.8 | −243 | 51:49 | 98 |
| 37 | i-Bu | I | I | 3.5 | −229 | 54:46 | 90 |
| 38 | $CH_2C_6H_4OCH_2C_6H_5$ | Cl | Cl | 2.2 | +244 | 67:33 | 90 |

[a] Reaction conditions: a) dried-pyridine, $(PhO)_3P$, 55° C., 16-24 h; b) dried-pyridine, $(Ph)_3P$, 220° C., 1.5 min;
[b] Optical rotation;
[c] e.r. = enantiomeric ratio determined by enantiosselectiv LC (column: amylose, Lux ® 5 μm Amylose-1, 250 × 4.6 mm, flow rate: 0.5 ml/min, mobile phase: hexane/EtOH, 9:1), numbers atributted with letters a and b correspond to the respective enantiomers
[d] = % purity determined by RP-LC.

obtained by selecting diverse L-α-amino acids—valine, leucine, and isoleucine. The purities of the compounds were determined by reversed-phase liquid chromatography, (RP-LC, C18, MeOH: $H_2O$; 50:50) and was found to be higher than 95% while for compound 30 and 37 purities were of 90%.

In the present disclosure, the general conditions for the synthesis of compounds 27-37 is as follows. In a closed vial, 5-chloro anthranilic acid (47 in which R'=H and R"=Cl, 34 mg, 200 μmol) for 27, 28, and 29, or 3,5-dichloro anthranilic acid, (47 in which R' and R"=Cl, 41 mg, 200 μmol) for 30, 31, and 32, or 5-iodoanthranilic acid, (47 in which R'=H and R"=I, 53 mg, 200 μmol) for 33 and 35, or 5-bromo anthranilic acid, (47 in which R'=H and R"=Br, 43 mg, 200 μmol) for 34 and 36, or 3,5-diodo anthranilic acid (47 in which R' and R"=I, 78 mg, 200 μmol) for 37; was added N-Boc-L-valine (48 which R=i-Pr, 44 mg, 200 μmol) for 27, 30, 33 and 34, or N-Boc-L-leucine (48 in which R=i-Bu, 46 mg, 200 μmol) for 28, 31, 35, and 37, or N-Boc-L-isoleucine (48 in which R=s-Bu, 46 mg, 200 μmol) for 29 and 32 (as present in Table 1), and triphenylphosphite (63 μL, 220 μmol) were added along with 1 mL of dried pyridine. The vial was heated in heating block with stirring at 55° C. for 16-24 h. After cooling the mixture to room temperature, D-tryptophan methyl ester hydrochloride (50, 51 mg, 200 μmol) was added, and the mixture was irradiated in the microwave at a constant temperature at 220° C. for 1.5 min. Four reaction mixtures were prepared in the same conditions and treated in parallel. After removing the solvent with toluene, the crude product was purified by flash column chromatography using hexane:EtOAc (60:40) as a mobile phase. The preparative TLC was performed using $CH_2Cl_2$:$Me_2CO$ (95:5) as mobile phase. The major compound appeared as a black spot with no fluorescence under the UV light. The desired compounds were collected as yellow solids. Before analysis, compounds were recrystallized from methanol.

In an embodiment, the characterization of (1S, 4R)-4-((1H-indol-3-yl)methyl)-8-chloro-1-isopropyl-1,2-dihydro-6H-pyrazino[2,1-b]quinazoline-3,6(4H)-dione (27) is as follows: Yield: 39.8 mg, 7%; e.r=56:44; mp: 200.3.202.4° C.

$$[\alpha]_D^{30} = -273(c0.05; CHCl_3);$$

$v_{max}$(KBr) 3277, 2924, 1682, 1592, 1470,1323, 741 $cm^{-1}$; $^1H$ NMR (300 MHz, $CDCl_3$): δ8.33 (d, 1H, J=2.5 Hz, CH), 8.33 (br, 1H, NH-indol), 7.70 (dd, 1H, J=8.7 and 2.5 Hz, CH), 7.50 (d, J=8.7 Hz, CH), 7.39 (d, 1H, J=8.0 Hz, CH-Trp), 7.30 (d, J=8.1 Hz, CH-Trp), 7.12 (t, 1H, J=8.0 Hz, CH-Trp), 6.92 (t, 1H, J=8.0 Hz, CH-Trp), 6.63 (d, 1H, J=2.3 Hz, CH-Trp), 5.64 (dd, 1H, J=5.4 and 2.7, CH*-Trp), 5.72 (s, 1H, NH-amide), 3.73 (dd, 1H, J=15.0 and 2.7 Hz, $CH_2$-Trp), 3.63 (dd, 1H, J=15.0 and 5.4 Hz, $CH_2$-Trp), 2.76 (d, J=2.3 Hz, CH*-val), 2.60 (dtd, 1H, J=13.9, 6.9, and 2.3 Hz, CH-val), 0.64 (d, 6H, J=6.1 Hz, $CH_3$-val); $^{13}C$ NMR (75 MHz, $CDCl_3$): δ169.2 (C=O), 159.9 (C=O), 150.6 (C=N), 145.6 (C), 136.1 (C-Trp 135.7 (CH), 132.8 (C), 128.9 (CH), 127.2 (C-Trp), 126.2 (CH), 123.6 (CH-Trp), 122.5 (CH-Trp), 121.2 (C), 119.9 (CH-Trp), 118.6 (CH-Trp), 111.1 (CH-Trp), 109.1 (C-Trp), 57.0 (CH*-Trp), 58.0 (CH*-val), 29.3 (CH-val), 27.3 ($CH_2$-Trp), 18.8 ($CH_3$-val), 14.8 ($CH_3$-val); (+)-HRMS-ESI m/z: 421.1442 $(M+H)^+$, 443,1264 $(M+Na)^+$ (calculated for $C_{23}H_{22}O_2Cl$, 421.1432; $C_{23}H_{21}N_4O_2ClNa$, 443.1252).

In an embodiment, the characterization of (1S,4R)-4-(1H-indol-3-yl)methyl)-8-chloro-1-isobutyl-1,2-dihydro-6H-pyrazino[2,1-b]quinazoline-3,6(4H)-dione (28) is as follows: Yield: 12.3 mg, 3%; e.r=44:56; mp: 2082-210.1° C.;

$$[\alpha]_D^{30} = +154(c0.15; CHCl_3);$$

$v_{max}$ (KBr)) 3277, 2924, 1682, 1592, 1470, 1323, 741 $cm^{-1}$; $^1H$ NMR (300 MHz, $CDCl_3$): δ8.33 (d, 1H, J=2.4 Hz, CH), 8.07 (br, 1H, NH-indol), 7.70 (dd, 1H, J=8.7 and 2.4 Hz, CH), 7.54 (d, J=8.7 Hz, CH), 7.46 (d, 1H, J=7.8 Hz, CH-Trp), 7.29 (d, J=7.8 Hz, CH-Trp), 7.13 (t, 1H, J=7.8 Hz, CH-Trp), 6.98 (t, 1H, J=7.8 Hz, CH-Trp), 6.65 (d, 1H, J=2.4 Hz, CH-Trp), 5.65 (dd, 1H, J=5.3 and 2.7, CH*-Trp), 5.71 (s, 1H, NH-amide), 3.76 (dd, 1H, J=15.1 and 2.7 Hz, $CH_2$-Trp), 3.6:3 (dd, 1H, J=15.1 and 5.3 Hz, $CH_2$-Trp), 2.70 (dd, J=9.7 and 2.3 Hz, CH*-Leu), 1.97 (ddd, 1H, J=11.8, 7.7, and 2.1 Hz, CH-Leu), 1.39-1.30 (m, 2H, $CH_2$-Leu), 0.77 (d, 3H, J=6.4 Hz, $CH_3$-Leu), 0.28 (d. 3H, J=6.5 Hz, $CH_3$-Leu); $^{13}C$ NMR (75 MHz, $CDCl_3$): δ169.1 (C=O), 159.8 (C=O), 151.9 (C=N), 145.5 (C), 136.0 (C-Trp 135.1 (CH), 132.9 (C), 129.1 (CH), 127.2 (C-Trp), 126.2 (CH), 123.6 (CH-Trp), 122.7 (CH-Trp), 121.2 (C), 120.2 (CH-Trp), 118.7 (CH-Trp), 111.1 (CH-Trp), 109.5 (C-Trp), 57.5 (CH*-Trp), 50.8 (CH*-Leu), 40.2 ($CH_2$-Leu), 27.2 ($CH_2$-Trp), 24.1 (CH-Leu), 23.3 ($CH_3$-Leu), 19.7 ($CH_3$-Leu); (+)-HRMS-ESI m/z: 435.1579 $(M+H)^+$, 457.1206 $(M+Na)^+$ (calculated for $C_{24}H_{24}N_4O_2Cl$, 435.1588; $C_{24}H_{23}N_4O_2ClNa$, 457.1408).

In an embodiment, the characterization of (1S,4R)-4-((1H-indol-3-yl)methyl)-1-((S)-sec-butyl)-8-chloro-1,2-dihydro-6H-pyrazino[2,1-b]quinazoline-3,6(4H)-dione (29) is as follows: Yield: 16.7 mg, 3%; e.r=46:54; mp: 209.1-211.2° C.;

$$[\alpha]_D^{30} = +130(c0.03;$$

$v_{max}$(KBr) 3277, 2924, 1682, 1592, 1470, 1323, 741 $cm^{-1}$; $^1H$ NMR (300 MHz, $CDCl_3$): δ8.33 (d, 1H, J=2.4 Hz, CH), 8.05 (br, 1H, NH-indol), 7.70 (dd, 1H, J=8.7 and 2.4 Hz, CH), 7.49 (d, J=8.7 Hz, CH), 7.38 (d, 1H, J=8.0 Hz, CH-Trp), 7.29 (d, J=8.0 Hz, CH-Trp), 7.13 (t, 1H, 8.0 Hz, CH-Trp), 6.92 (t, 1H, J=8.0 Hz, CH-Trp), 6.63 (d, 1H, J=2.4 Hz, CH-Trp), 5.64 (dd, 1H, J=5.3 and 2.8, CH*-Trp), 5.80 (s, 1H, NH-amide), 3.72 (dd, 1H, J=15.1 and 2.8 Hz, $CH_2$-Trp), 3.62 (dd, 1H, J=15.1 and 5.3 Hz, $CH_2$-Trp), 2.69 (d, J=2.2 Hz, CH*-Ile), 2.29 (ddd, 1H, J=11.6, 7.7, and 4.8 Hz, CH*-Ile), 0.99-0.79 (m, 2H), 0.70 (d, 3H, J=7.7 Hz, $CH_3$-Ile), 0.63 (d, 3H. J=7.2 Hz, $CH_3$-Ile); $^{13}C$ NMR (75 MHz, $CDCl_3$)) δ169.1 (C=O), 159.9 (C=O), 150.7 (C=N), 145.5 (C), 136.0 (C-Trp 135.1 (CH), 132.8 (C), 128.9 (CH), 127.2 (C-Trp), 126.2 (CH), 123.5 (CH-Trp), 122.7 (CH-Trp), 121.1 (C), 120.1 (CH-Trp), 118.6 (CH-Trp), 111.1 (CH-Trp), 109.2 (C-Trp), 58.3 (CH*-Ile), 57.0 (CH*-Trp), 36.2 (CH-Leu), 27.3 ($CH_2$-Trp), 23.1 ($CH_2$-Ile), 15.6 ($CH_3$-Ile), 12.0 ($CH_3$-Ile); (+)-HRMS-ESI m/z: 435.1580 $(M+H)^+$, 457.1394 $(M+Na)^+$ (calculated for $C_{24}H_{24}N_4O_2Cl$, 434.1588; $C_{24}H_{23}N_4O_2ClNa$, 457.1408).

In an embodiment, the characterization of (1S, 4R)-4-((1H-indol-3-yl)methyl)-8,10-dichloro-1-isopropyl-1,2-dihydro-6H-pyrazino[2,1-b]quinazoline-3,6(4H)-dione (30) is as follows: Yield: 22.1 mg, 5%; e.r=43:57; mp: 232.9-235.1° C.;

$$[\alpha]_D^{30} = +140(c0.038;$$

$CHCl_3$); $v_{max}$ (KBr) 3293, 2954, 1671, 1611, 1511, 1465, 1240, 112, and 697 $cm^{-1}$, $^1H$ NMR (300 MHz, DMSO-$d_6$); δ10.2 (br, 1H, NH-indol), 8.20 (d, 1H, J=2.4 Hz, CH), 7.83 (d, 1H, J=2.4 Hz, CH), 7.37 (d, 1H, J=8.1 Hz, CH-Trp), 7.33 (d, J=8.1 Hz, CH-Trp), 7.11 (s, 1H, NH-amide), 7.07 (t, 1H, J=7.6 Hz, CH-Trp), 6.87 (t, 1H, J=7.6 Hz, CH-Trp), 6.66 (d, 1H, J=2.3 Hz, CH-Trp), 5.50 (dd, 1H, J=5.3 and 2.9, CH*-Trp), 3.69 (dd, 1H, J=14.9 and 2.9 Hz, $CH_2$-Trp), 3.58

(dd, 1H, J=14.9 and 5.3 Hz, $CH_2$-Trp), 2.76 (d, J=2.2 Hz, CH*-val), 2.60-254 (m, 1H, CH-val), 0.71 (dd, 6H, J=8.4 and 7.2 Hz, $CH_3$-val); $^{13}C$ NMR (75 MHz, $CDCl_3$): δ169.2 (C═O), 159.9 (C═O), 150.6 (C═N), 145.7 (C), 136.0 (C-Trp), 135.1 (CH), 132.8 (C), 128.9 (CH), 127.2 (C-Trp), 126.2 (CH), 123.6 (CH-Trp), 122.7 (CH-Trp), 121.2 (C), 120.1 (CH-Trp), 118.6 (CH-Trp), 111.1 (CH-Trp), 109.2 (C-Trp), 58.1 (CH*-val), 57.0 (CH*-Trp), 29.3 (CH-val), 27.3 ($CH_2$-Trp), 18.8 ($CH_3$-val), 14.8 ($CH_3$-val; (+)-HRMS-ESI m/z: 455.1436 $(M+H)^+$ (calculated for $C_{23}H_{21}N_4O_2Cl_2$455.1041).

In an embodiment, the characterization of (1S, 4R)-4-((1H-indol-3-yl)methyl)-8,10-dichloro-1-isobutyl-1,2-dihydro-6H-pyrazino[2,1-b]quinazoline-3,6(4H)-dione (31) is as follows: Yield: 41.8 mg, 4.5%; e.r=60:40; mp: 253.4-254.3° C.;

$$\{\alpha\}_D^{30} = -169\ (c\ 0.04;\ CHCl_3);$$

$v_{max}$(KBr) 3289, 2960, 1680, 1600, 1556, 1315, 757, 720 $cm^{-1}$, $^1H$ NMR (300 MHz, DMSO-$d_6$): 10.22 (hr, 1H, NH-indol), δ8.13 (d. 1H, J=2.4 Hz, CH), 7.75 (d, 1H, J=2.4 Hz, CH), 7.33 (d, 1H, J=8.0 Hz, CH-Trp), 7.25 (d, J=8.0 Hz, CH-Trp), 7.19 (br, NH-amide), 7.00 (t, 1H, J=8.0 Hz, CH-Trp), 6.82 (t, 1H, J=8.0 Hz, CH-Trp), 6.60 (d, 1H, J=2.4 Hz, CH-Trp), 5.42 (dd, 1H, J=5.4 and 2.9, CH*-Trp), 3.63 (dd, 1H, J=15.0 and 2.9 Hz, $CH_2$-Trp), 3.50 (dd, 1H, J=15.0 and 5.4 Hz, $CH_2$-Trp), 2.68 (dd, J=7.3 and 4.9 Hz, CH*-Leu), 1.94-1.86 (m, 1H $CH_2$-Leu), 1.50 (tt, 1H, J=13.2 and 6.5 Hz, CH-Leu), 1.29-1.22 (m, 1H, $CH_2$-Leu), 0.56 (d, 3H, J=6.6 Hz, $CH_3$-Leu), 0.35 (d, 3H, J=6.6 Hz, $CH_3$-Leu); $^{13}C$ NMR (75 MHz, DMSO-$d_6$): δ168.4 (C═O), 158.8 (C═O), 152.8 (C═N), 142.0 (C), 135.9 (C-Trp), 134.1. (CH), 132.6 (C), 131.4 (C), 126.5 (C-Trp), 124.3 (CH), 123.5 (CH-Trp), 121.6 (CH-Trp), 121.5 (C), 118.9 (CH-Trp), 117.7 (CH-Trp), 111.1 (CH-Trp), 107.7 (C-Trp), 57.3 (CH*-Trp), 50.6 (CH*-Leu), 39.6 ($CH_2$-Leu), 26.2 ($CH_2$-Trp), 23.8 (CH-Leu), 22.1 ($CH_3$-Leu), 20.5 ($CH_3$-Leu); (+)-HRMS-ESI m/z: 469.1186 $(M+H)^+$, 491.1008 $(M+Na)^+$ (calculated for $C_{24}H_{23}N_4O_2Cl_2$, 469.1198; $C_{24}H_{22}N_4O_2Cl_2Na$, 491.1018).

In an embodiment, the characterization of (1S, 4R)-4 ((1H-indol-3-yl)methyl)-1-((S)-sec-butyl) 8,10-dichloro-1, 2-dihydro-6H-pyrazino[2,1-b]quinazoline-3,6(4H)-dione (32) is as follows: Yield: 22.4 mg, 2.6%; e.r=71:29; mp: 252.9-254.7° C.;

$$[\alpha]_D^{30} = -264\ (c\ 0.034;\ CHCl_3);$$

$v_{max}$(KBr) 3373, 3074, 2922, 1698, 1609, 1550, 1450, 1262, 794 $cm^{-1}$; $^1H$ NMR (300 MHz, $CDCl_3$): δ8.33 (d, 1H, J=2.4 Hz, CH), 8.05 (br, 1H, NH-indol), 7.70 (d, 1H, J=2.4 Hz, CH), 7.38 (d, 1H, J=7.9 Hz, CH-Trp), 7.29 (d, J=7.9 Hz, CH-Trp), 7.13 (t, 1H, J=7.9 Hz, CH-Trp), 6.92 (t, 1H, J=7.9 Hz, CH-Trp), 6.63 (d, 1H, J=2.4 Hz, CH-Trp), 5.64 (dd, 1H, J=5.3 and 2.8, CH*-Trp), 5.80 (s, 1H, NH-amide), 3.72 (dd, 1H, J=15.0 and 2.8 Hz, $CH_r$-Trp), 3.62 (dd, 1H, J=15.0 and 5.3 Hz, $CH_2$-Trp), 2.69 (d, J=2.2 Hz, CH*-Ile), 2.29 (ddd, 1H, J=11.6, 7.9, and 4.8 Hz, CH*-Ile), 0.99-0.79 (m, 2H, $CH_2$-Ile), 0.70 (d, 3H, J=7.3 Hz, $CH_3$-Ile), 0.63 (d, 3H, J=7.3 Hz, $CH_3$-Ile); $^{13}C$ NMR (75 MHz, $CDCl_3$): δ168.9 (C═O), 159.5 (C═O), 151.3 (C═N), 142.5 (C), 136.1 (C-Trp) 135.0 (CH), 133.2 (C), 132.4 (C), 127.1 (C-Trp), 125.1 (CH), 123.5 (CH-Trp), 122.9 (CH-Trp), 122.1 (C), 120.2 (CH-Trp), 118.6 (CH-Trp), 111.1 (CH-Trp), 109.2 (C-Trp), 58.2 (CH*-Ile), 57.3 (CH*-Trp), 36.2 (CH-Leu), 27.1 ($CH_2$-Trp), 23.6 ($CH_2$-Ile), 15.5 ($CH_3$-Ile), 12.1 (CH-Ile; (+)-HRMS-ESI m/z: 469.1186 $(M+H)^+$, 491.1024 $(M+Na)^+$ (calculated for $C_{24}H_{23}N_4O_2Cl_2$, 469.1198; $C_{24}H_{22}N_4O_2Cl_2Na$, 491.1018).

In an embodiment, the characterization of (1S,4R)-4-((1H-indol-3-yl)methyl)-8-iodo-1-isopropyl 1,2-dihydro-6H-pyrazino[2,1-b]quinazoline-3,6(4H)-dione (33) is as follows: Yield: 21.2 mg, 4.1%; e.r=51:49; mp: 246.5-248.2 C;

$$[\alpha]_D^{30} = -175\ (c\ 0.041;$$

$v_{max}$ (KBr) 3311, 3192, 2963, 1681, 1655, 1588, 1464, 1246, 828, and 741 $cm^{-1}$; $^1H$ NMR (300 MHz, $CDCl_3$): δ8.71 (d, 1H, J=2.4 Hz, CH), 8.04 (br, 1H, NH-indol), 8.02 (dd, 1H, J=8.6 and 2.1 Hz, CH), 7.41 (d, 1H, J=8.0 Hz, CH-Trp), 7.30 (d, J=8.4 Hz, CH) 7.29 (d, J=8.4 Hz, CH-Trp), 7.13 (ddd, 1H, J=8.0, 7.1 and 0.9 Hz, CH-Trp), 6.94 (ddd, 1H, J=8.0, 7.1 and 0.9 Hz, CH-Trp), 6.61 id, 1H, J=2.4 Hz, CH-indol), 5.64 (dd, 1H, J=5.4 and 2.8, CH*-Trp), 5.67 (s, 1H, NH-amide), 3.73 (dd, 1H, J=14.9 and 2.7 Hz, $CH_2$-Trp), 3.61 (dd, 1H, J=15.1 and 5.4 Hz, CH-Trp), 2.64 (d, J=2.4 Hz, CH*-val), 2.63-2.56 (m, 1H, CH-val), 0.63 (d, 6H, J=6.8 Hz, $CH_3$-val); $^{13}C$ NMR (75 MHz, $CDCl_3$): δ169.1 (C═O), 159.5 (C═O), 151.0 (C═N), 146.3 (C), 143.5 (CH), 136.0 (C-Trp 135.7 (CH), 129.0 (CH), 127.2 (C-Trp) 123.5 (CH-indol), 122.7 (CH-Trp), 121.7 (C), 120.2 (CH-Trp), 118.7 (CH-Trp), 111.1 (CH-Trp), 109.3 (C-indol), 91.4 (C), 58.1 (CH*-val), 57.0 (CH*-Trp) 29.7 (CH-val), 27.3 (CH Trp), 18.8 ($CH_3$-val), 14.8 ($CH_3$-val); (+)-HRMS-ESI m/z: 513.0778 $(M+H)^+$ (calculated for $C_{23}H_{22}N_4O_2I$, 513.0787).

In an embodiment, the characterization of (1S,4R)-4-((1H-indol-3-yl)methyl)-8-bromo-1-isopropyl-1,2-dihydro-6H-pyrazino[2,1-b]quinazoline-3,6(4H)-dione (34) is as follows: Yield: 10.9 mg, 1.2%; e.r=50:50; mp: 236.5-238.0° C.;

$$[\alpha]_D^{30} = -170\ (c\ 0.03;\ CHCl_3);$$

$v_{max}$ (KBr) 3292, 3193, 2958, 1681, 1666, 1592, 1466, 1237, 832, and 742 $cm^{-1}$; $^1H$ NMR (300 MHz, $CDCl_3$): δ8.50 (d, 1H, J=2.2 Hz, CH), 8.05 (br, 1H, NH-indol), 7.84 (dd, 1H, J=8.7 and 2.2 Hz, CH), 7.41 (J=8.7 Hz, CH), 7.29 (dd, 2H, J=8.0 and 2.2 Hz, CH-Trp (2)), 7.13 (ddd, 1H, J=8.0, 7.1 and 1.0 Hz, CH-Trp), 6.93 (ddd, 1H, J=8.0, 7.1 and 1.1 Hz, CH-Trp), 6.62 (d, 1H, J=2.4 Hz, CH-Trp), 5.64 (dd, 1H, J=5.4 and 2.8, CH*-Trp), 5.63 (s, 1H, NH-amide), 3.73 (dd, 1H, J=14.9 and 2.8 Hz, $CH_2$-Trp), 3.62 (dd, 1H, J=15.0 and 5.4 Hz, $CH_2$-Trp), 2.66 (d, J=2.4 Hz, CH*-val), 2.60 (m, 1H, CH-val), 0.65 (d, 3H, J=6.5 Hz, $CH_3$-val), 0.63 (d, 3H, J=6.4 Hz, $CH_3$-val); $^{13}C$ NMR (75 MHz, $CDCl_3$); δ169.1 (C═O), 159.7 (C═O), 150.9 (C═N), 145.9 (C), 138.1 (CH), 136. (C-Trp), 129.4 (C), 129.1 (CH), 127.2 (C-trp), 123.5 (CH-indol), 122.7 (CH-Trp), 121.5 (C), 120.6 (CH-Trp), 120.2 (C), 118.7 (CH-Trp), 111.1 (CH-Trp), 109.3 (C-Trp), 57.0 (CH*-trp), 53.8 (CH*-val), 29.7 (CH-val), 27.3 ($CH_2$-Trp), 18.8 ($CH_3$-val), 14.8 ($CH_3$-val); (+)-HRMS-ESI m/z: 465.0987 $(M+H)^+$, 487.0726 $(M+Na)^+$ (calculated for $C_{23}H_{22}N_4O_2Br$: 465.0926; $C_{23}H_{21}N_4O_2BrNa$: 487.0746).

In an embodiment, the characterization of (1S,4R)-4-((1H-indol-3-yl)methyl)-8-iodo-1-isobutyl-1,2-dihydro-6H-pyrazino[2,1-b]quinazoline-3,6(4H)-dione (35) is as follows: Yield: 62.4 mg, 11.8%; e.r=51:49; mp: 192.1-194.3° C.;

$$[\alpha]_D^{30} = -165\ (c0.038;\ CHCl_3);$$

$v_{max}$(KBr) 3318, 2956, 1671, 1686, 1593, 1464, 1247, 790, and 740 $cm^{-1}$, $^1$H NMR (300 MHz, $CDCl_3$); δ8.70 (d, 1H, J=2.1 Hz, CH), 8.03 (br, 1H, NH-indol), 8.03 (dd, 1H, J=8.6 and 2.1 Hz, CH), 7.44 (d, J=7.9 Hz, CH-Trp), 7.33 (d, 1H, J=8.6 Hz, CH), 7.29 (d, J=7.9 Hz, CH-Trp), 7.13 (t, 1H, J=7.9 Hz, CH-Trp), 6.98 (t, 1H, J=7.9 Hz, CH-Trp), 6.68 (d, 1H, J=2.4 Hz, CH-Trp), 5.96 (s, 1H, NH-amide), 5.65 (dd, 1H, J=5.2 and 2.8, CH*-Trp), 3.76 (dd, 1H, J=15.0 and 2.8 Hz, $CH_2$-Trp), 3.63 (dd, 1H, J=15.0 and 5.2 Hz, $CH_2$-Trp), 2.69 (dd, 9.6 and 3.3 Hz, CH*-Leu), 2.02-1.92 (m, 1H, CH-Leu), 1.40-1.30 (m, 2H, $CH_2$-Leu), 0.79 (d, 3H, J=6.5 Hz, $CH_2$-Leu), 0.29 (d, 3H, J=6.4 Hz, $CH_3$-Leu); $^{13}$C NMR (75 MHz, $CDCl_3$): δ169.5 (C═O), 159.4 (C═O), 152.1 (C═N), 146.3 (C), 143.4 (CH), 136.1 (C-Trp), 135.7 (C), 129.2 (CH), 127.1 (C-Trp), 123.5 (CH-Trp), 122.9 (CH-Trp), 121.8 (C), 120.4 (CH-Trp), 118.7 (CH-Trp), 111.2 (CH-Trp), 109.5 (C-Trp), 91.5 (C), 57.4 (CH*-Trp), 51.0 (CH*-leu), 40.1 ($CH_2$-Leu), 27.1 ($CH_2$-Trp), 24.1 (CH-Leu), 23.3 ($CH_3$-Leu), 19.7 ($CH_3$-Leu); (+)-HRMS-ESI m/z: 527.0936 $(M+H)^+$, 549.0748 $(M+Na)^+$ (calculated for $C_{24}H_{24}N_4O_2I$, 527.0944; $C_{24}H_{23}N_4O_2INa$, 549,0764).

In an embodiment, the characterization of (1S,4R)-4-((1H-indol-3-yl)methyl)-8-bromo-1-isobutyl-1,2-dihydro-6H-pyrazino[2,1-b]quinazoline-3,6(4H)-dione (36) is as follows: Yield: 64.6 mg, 13.8%; e.r=51:49; mp: 227.0-228.2° C.;

$$[\alpha]_D^{30} = -243(c0.037;\ CHCl_3);$$

$v_{max}$(KBr) 3284, 2959, 1686, 1658, 1599, 1433, 1245, 746, and 684 $cm^{-1}$; $^1$H NMR (300 MHz, $CDCl_3$): δ8.50 (d, 1H, J=2.3 Hz, CH), 8.06 (br, 1H, NH-indol), 7.84 (dd, 1H, 8.5 and 2.3 Hz, CH), 7.47 (dd, 2H, J=8.1 and 1.9 Hz, CH-Trp (2)), 7.29 (d, J=8.5 Hz, CH-Trp), 7.14 (t, 1H, J=8.0 Hz, CH-Trp), 6.92 (t, 7.9 Hz, CH-Trp), 6.65 (d, 1H, J=2.4 Hz, CH-Trp), 5.65 (dd, 1H, J=5.2 and 2.9, CH*-Trp), 5.71 (s, 1H, NH-amide), 3.76 (dd, 1H, J=15.0 and 2.9 Hz, $CH_2$-Trp), 3.63 (dd, 1H, J=15.0 and 5.2 Hz, $CH_2$-Trp), 2.70 (dd, J=9.7 and 3.3 Hz, CH*-Leu), 2.07-4.89 (m, 1H, CH-Leu), 1.38-1.21 (m, 2H, $CH_2$-Leu), 0.77 (d, 3H, J=6.3 Hz, $CH_3$-Leu), 0.28 (d, 3H, J=6.5 Hz, $CH_3$-Leu); $^{13}$C NMR (75 MHz, $CDCl_3$): δ169.1 (C═O), 159.7 (C═O), 152.0 (C═N), 145.8 (C), 137.8 (CH), 136.8 (C-Trp), 129.4 (C), 129.2 (CH), 127.1 (C-Trp), 123.8 (CH-Trp), 122.9 (CH-Trp), 121.6 (C), 120.6 (CH), 120.4 (CH-Trp), 118.7 (CH-Trp), 111.2 (CH-Trp), 109.6 (C-Trp), 57.5 (CH*-Trp), 50.8 (CH*-Leu), 40.1 ($CH_2$-Leu), 27.1 ($CH_2$-Trp), 24.1 (CH-Leu), 23.3 ($CH_3$-Leu), 19.7 ($CH_3$-Leu); (+)-HRMS-ESI m/z: 479.1086 $(M+H)^+$, 501.0912 $(M+Na)^+$ (calculated for $C_{24}H_{24}N_4O_2Br$, 479.1082; $C_{24}H_{23}N_4BrNa$, 501.0900).

In an embodiment, the characterization of (1S,4R)-4-(1H-indol-3-yl)methyl)-8,10-diodo-1-isobutyl-1,2-dihydro-6H-pyrazino[2,1-b]quinazoline-3,6(4H)-dione (37) is as follows: Yield: 22.5 mg, 3.5%; e.r=54:46; mp: 242.8-243.8° C.;

$$[\alpha]_D^{30} = -229\ (c\,0.032;$$

$v_{max}$ (KBr) 3313, 2955, 1681, 1599, 1462, 1261, 772, and 669 $cm^{-1}$; $^1$H NMR (300 MHz, DMSO-$d_6$): 10.17 (br, 1H, NH-indol), δ8.62 (d, 1H, J=1.9 Hz, CH), 8.55 (d, 1H, J=1.9 Hz, CH), 7.41 (d, 1H, J=8.0 Hz, CH-Trp), 7.33 (d, J=8.0 Hz, CH-Trp), 7.11 (br, NH-amide), 7.09 (t, 1H, J=7.9 Hz, CH-Trp), 6.91 (t, 1H, J=7.9 Hz, CH-Trp), 6.68 (d, 1H, J=2.3 Hz, CH-indol), 5.50 (dd, 1H, J=5.2 and 2.9, CH*-Trp), 3.72 (dd, 1H, J=14.9 and 2.9 Hz, $CH_2$-Trp), 3.58 (dd, 1H, J=15.0 and 5.2 Hz, $CH_2$-Trp), 2.75 (dd, J=6.6 and 5.3 Hz, CH*-Leu), 2.11-1.95 (m, 1H, $CH_2$-Leu), 1.68-4.53 (m, 1H $CH_2$-Leu), 1.38-1.23 (m, 1H, J=13.2 and 6.5 Hz, $CH_2$-Leu), 0.62 (t, 3H, J=6.5 Hz, $CH_3$-Leu), 0.47 (d, 3H, J=6.6 Hz, $CH_3$-leu); $^{13}$C NMR (75 MHz, DMSO-$d_6$): δ158.4 (C═O), 162.0 (C═O), 153.0 (C═N), 151.1 (C), 136.2 (C-Trp), 135.9 (C), 127.1 (C-Trp), 123.4 (CH-Trp), 121.8 (C), 121.5 (CH-Trp), 119.0 (CH-Trp), 117.8 (CH-Trp), 111.0 (CH-Trp), 107.8 (C-Trp), 91.5 (CH), 89.2 (CH), 57.4 (CH*-Trp), 50.5 (CH*-Leu), 39.4 ($CH_2$-Leu), 26.3 ($CH_2$Trp), 23.9 (CH-Leu), 21.8 ($CH_3$-Leu), 20.6 ($CH_3$-Leu); (+)-HRMS-ESI m/z: 652.9915 $(M+H)^+$, 674.9746 $(M+Na)^+$ (calculated for $C_{24}H_{23}N_4O_2Cl_2$, 652.9910; $C_{24}H_{22}N_4O_2Na$, 674.9730).

The quantitative analysis of enantioselective liquid chromatography was carried out as follows. Compounds 27-37 were prepared using HPLC grades n-hexane:EtOH (50:50) at a final concentration 50 μg/ml. The HPLC system comprised a JASCO model 880-PU intelligent HPLC pump (JASCO corporation, Tokyo, Japan), equipped with a 7125 injector (Rheodyne LCC, Rohnert Park, CA, USA) fitted with a 20 μL LC loop, a JASCO model 880-30 solvent mixer involving a 875-UV intelligent UV/VIS detector, a system equipped with a chiral column (Lux® 5 μm Amylose-1, 250×4.6 trim). The data acquisition was performed using ChromNAC chromatography Data system (version 1.19.1) from JASCO Corporation (Tokyo, Japan). The mobile phase consisted of the mixture of n-hexane:EtOH (90:10, v/v), at a flow rate of 0.5 mL/min. The mobile phase was prepared in a volume/volume ratio and degassed in an ultrasonic bath for at least 15 min before use. The chromatographic analyses were carried out in isocratic mode at 22±2° C., in duplicate. The UV detection was performed at a wavelength of 254 nm. The volume void time was considered to be equal to the peak of solvent, front and was taken from each particular run. The enantiomeric ratio (e.r) were determined by the mean percentage of peak area of eluted peaks.

The semipreparative enantioselective resolution was as follows. Compound 27, 28 and 31 were prepared in the mixture of HLCP grade solvent n-hexane:EtoH (50:50) at the concentration 10 mg/mL, and the injection volume was 100-200 μL. The HPLC system is similar to what described in quantitative analysis equipped with an in-house column amylose tris-3,5-dimethylphenylcarbamate coated with Nucleosil (500 A, 7 mm, 20%, w/w) packed into a stainless-steel (200 mm×7 mm I.D. size) column, prepared in the UFSCar laboratory. Semi-preparative chromatographic separations were first achieved through multiple injection with 200 μL at a flow rate of 2 mL/min. The chromatographic analyses were carried out in isocratic mode at 22±2° C. The UV detection was performed at a wavelength of 254 nm. The fraction collected was analyzed using the analytical column to determine their enantiomeric ratio/excess with the condition described above.

Chemistry for the 4$^{th}$ approach. Regarding the fourth approach of indole-containing pyrazino[2,1-b]quinazoline-3,6-diones 39-46, the compounds were also prepared via the highly effective and environmentally friendly microwave-assisted multicomponent polycondensation of amino acids. This methodology allowed us to prepare the fourth approach of pyrazinoquinazoline alkaloids through treatment of the anthranilic acid (51) derivatives with N-Boc-L-amino acids (52) and $(PhO)_3P$ at 55° C. for 16-20 h. Thereafter, D-tryptophan methyl ester hydrochloride (53) was added, and the mixture was stirred under microwave irradiation (300 W) at 220° C. for 1.5 min to furnish the final products 39.46 (Table 2).

TABLE 2

Microwave-assisted multicomponent synthesis of indole-containing quinazolinone alkaloids 39-46.

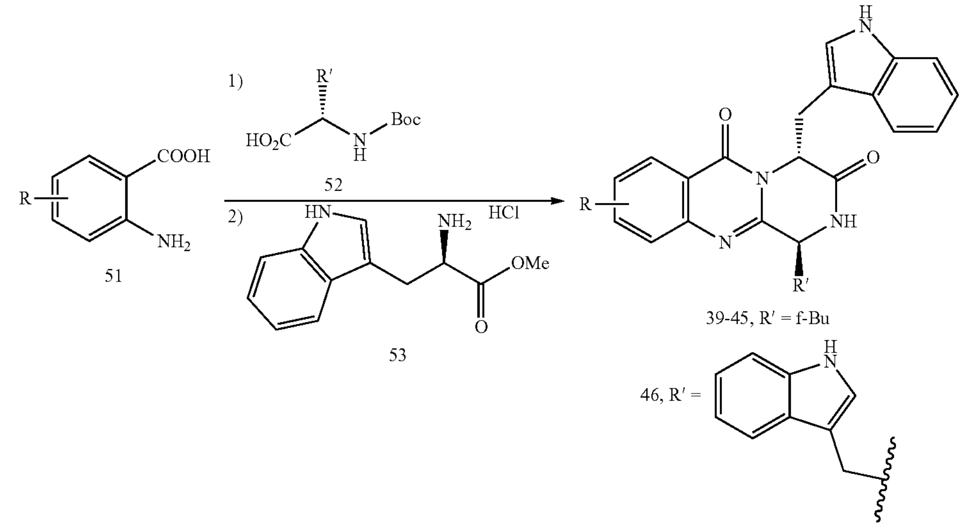

51

52

53

39-45, R′ = f-Bu

46, R′ =

| Anthranilic acid | Product | Compound | ClogP[a] | MW | Yield[b]/er[c] |
|---|---|---|---|---|---|
| 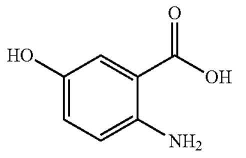 | 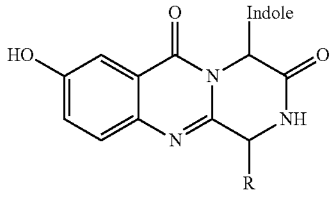 | 39 | 3.671 | 416.48 | 6.9/47:53 |
| 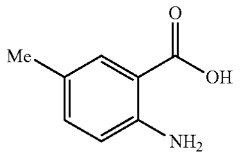 [SMILES: Nc1ccc(O)cc1C(=O)O] | 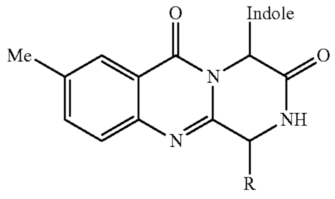 | 40 | 4.088 | 414.51 | 3.1/42:58 |
| 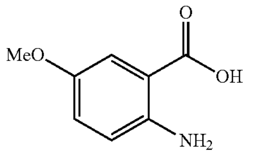 | 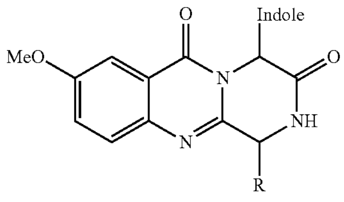 | 41 | 3.814 | 430.51 | 5.8/30:70 |
| 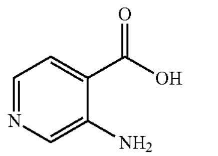 | 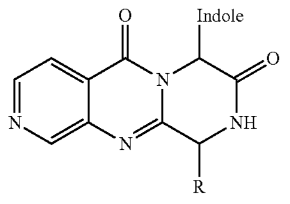 | 42 | 2.456 | 401.47 | 9.4/46:54 |

TABLE 2-continued
Microwave-assisted multicomponent synthesis of indole-containing quinazolinone alkaloids 39-46.
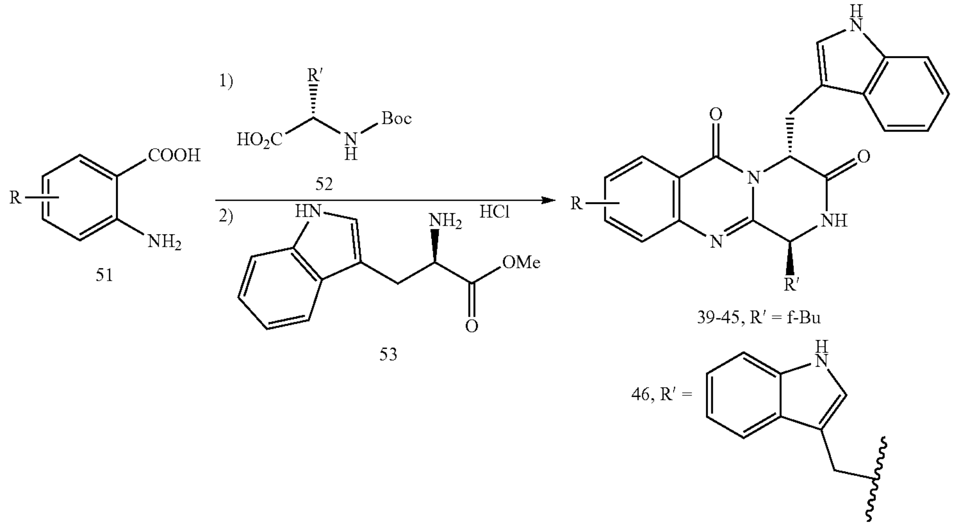
51
52
53
39-45, R′ = f-Bu
46, R′ =
| Anthranilic acid | Product | Compound | ClogP[a] | MW | Yield[b]/er[c] |
|---|---|---|---|---|---|
| 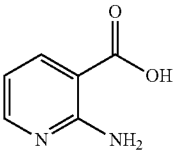 | 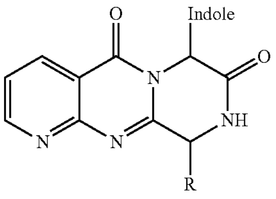 | 43 | 2.456 | 401.47 | 12.1/46:54 |
| 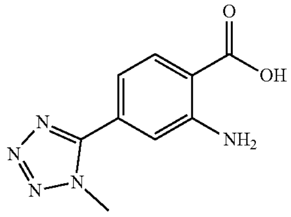 [SMILES: Cn1nnnc1-c1ccc(C(=O)O)c(N)c1] | 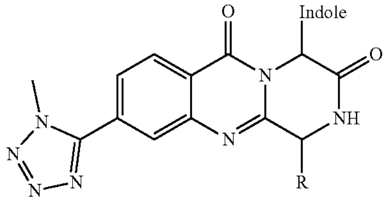 | 44 | 3.082 | 482.55 | 1.0/47:53 |
| 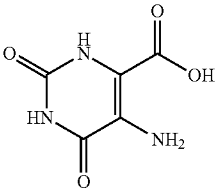 [SMILES: Nc1c(C(=O)O)[nH]c(=O)[nH]c1=O] | 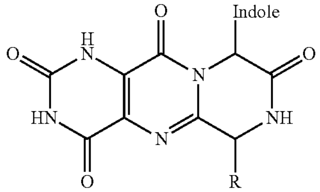 | 45 | 1.277 | 434.55 | 2.3/57:43 |
| 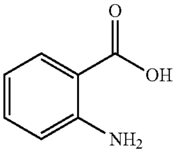 | 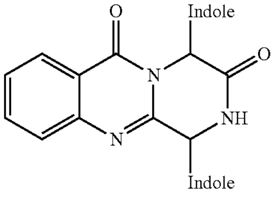 | 46 | 3.690 | 473.54 | 5.7/99:1 |
Reagents and conditions:
1) (PhO)3P, py, 55° C., 24 h,
2) PhO)3P, py, 220° C., 1.5 min,
[a]calculated based on Cambio Draw,
[b]obtained after purification,
[c]determined by enantioselective liquid chromatography.

In the present disclosure, the general conditions for the synthesis of quinazolinone-3,6-(4H)-diones compounds 39-46 is as follows. In a closed vial, 5-hydroxy-anthranilic acid (51a, 184 mg, 1.2 mmol) for 39, 5-methyl-anthranilic acid (51b, 181 mg, 1.2 mmol) for 40, 5-methoxy-anthranilic acid (51c, 200 mg, 1.2 mmol) for 41, 3-aminoisonicotinic acid (51d, 116 mg, 1.2 mmol) for 42, 2-aminoisonicotinic acid (51e, 116 mg, 200 μmol) for 43, 4-triazole-anthranilic acid (51f, 124 mg, 1.2 mmol) for 44, or 5-aminoordotic add (51 g, 205 mg, 1.2 mmol) for 45, or anthranilic acid (51h, 140 mg, 1.2 mmol) for 46 with N-Boc-L-leucine (52a, 299 mg, 1.2 mmol) for 39-45 or N-Boc-L-tryptophan, (52b, 365 mg, 1.2 mmol) for 46 and triphenyl phosphite (495 μL, 1.44 mmol) were added along with 6 mL of dried pyridine. The vial was heated in heating block with stirring at 55° C. for 16-24 h. After cooling the mixture to room temperature, n-tryptophan methyl ester hydrochloride (53, 306 mg, 1.2 mmol) was added, and the mixture was divided into 3 individual vials, and irradiated in the microwave at the constant temperature at 220° C. for 1.5 min. After removing the solvent with toluene, the crude product was purified by flash column chromatography using n-hexane:EtOAc (60; 40) as a mobile phase. The preparative TLC was performed using $CH_2Cl_2$:$Me_2CO$ (95:5) as mobile phase. The major compound appeared as a black spot with no fluorescence under the UV light. The desirable compounds 39-46 were collected as yellow solids, Before analysis, compounds were recrystallized from methanol.

In an embodiment, the characterization of (1S,4R)-4-(1H-indol-3-yl)methyl)-8-hydroxy-1-isobutyl-1,2-dihydro-6H-pyrazino[2,1-b]quinazoline-3,6(4H)-dione (39) is a follows: Yield: 38.5 mg, 6.9%; mp: 162.4-163.5° C. (MeOH);

$$[\alpha]_D^{30} = -74.60(c\,0.042;$$

$v_{max}$ (KBr) 3185, 3070, 1666,1617, 1431, 1247 and 776 $cm^{-1}$; $^1H$ NMR (300 MHz, $CDCl_3$): δ8.63 (d, 1H, J=3.6 Hz, CH), 8.02 (s, 1H, NH-Trp), 7.73 (d, 1H-J=2.9 Hz, OH), 7.53 (d, 2H, J 8.9 Hz, CH(2)), 7.34 (dd, 2H, J 7.7 and 4.0 Hz, CH-Trp (2)), 7.14 (t, 1H, J 7.1 Hz, CH-Trp), 7.00 (t, 1H, J 7.2 Hz, CH-Trp), 6.64 (d, 1H, J 23 Hz, CH-Trp), 5.66 (dd, 1H, J 5.3 and 3.0 Hz, CH*-Trp), 5.60 (s, 1H, NH-amide), 3.76 (dd, 1H, J 14.9 and 2.8 Hz, CH-Trp), 3.64 (dd, 1H, J 15.3 and 5.4 Hz, $CH_2$-Trp), 2.70 (dd, 1H, J 83 and 4.0 Hz, CH*-Leu), 1.70-1.59 (m, 1H CH-Leu), 1.42-1.33 (m, 2H, $CH_2$-Leu) 0.77 (d, 3H, J=6.3 Hz, $CH_3$-Leu), 0.27 (d, 3H, J=6.4 Hz, $CH_3$-Leu); $^{13}C$ NMR (75 MHz, Acetone $d_6$): δ169.7 (C═O), 161.1 (C═O), 157.2 (C—OH), 150.1 (C═N), 141.6 (C), 137.3 (C-Trp), 129.9 (CH), 128.3 (C-Trp), 124.9 (CM-Trp), 124.7 (CH), 122.5 (CH-Trp), 122.3 (C), 119.9 (CH-Trp), 119.1 (CH-Trp), 112.1 (CH-Trp), 110.0 (CH), 109.8 (C-Trp), 58.5 (CH*-Trp), 51.4 (CH*-Leu), 40.7 (CH-Leu), 27.4 ($CH_2$-Trp), 24.8 ($CH_2$-Leu), 23.3 ($CH_3$-Leu), 21.1 ($CH_3$-Leu).

In an embodiment, the characterization of (1S,4R)-4-((1H-indol-3-yl)methyl)-1-isobutyl-8-methyl-1,2-dihydro-6H-pyrazino[2,1-b]quinazoline-3,6(4H)-dione (40) is as follows: Yield: 15.6 mg, 3.1%; mp:156.7-157.0° C. (MeOH);

$$[\alpha]_D^{30} = -182(c0.055;$$

$v_{max}$(KBr) 3067, 2915, 1682, 1470, and 770 $cm^{-1}$; $^1H$ NMR (300 MHz, $CDCl_3$): δ8.16 (s, 1H, CH), 8.04 (br, 1H, NH-Trp), 7.59 (dd, 1H, J 8.3, 2.0 Hz, CH), 7.50 (d, 2H, J 8.2 CH & CH-Trp), 7.28 (d, 1H, J 8.2 Hz, CH-Trp), 7.13 (t, 1H, J 7.6 Hz, CH-Trp), 6.99 (t, 1H, J 7.9 Hz, CH-Trp), 6.63 (d, 1H, J 2.3 Hz, CH-Trp), 5.70 (s, 1H, NH-amide), 5.68 (dd, 1H, 15.4 and 2.9 Hz, CH*-Trp), 3.76 (dd, 1H, J 15.0 and 2.8 Hz, $CH_2$-Trp), 3.65 (dd, 1H, J 15.1 and 5.4 Hz, $CH_2$-Trp), 2.71 (dd, 1H, J 9.8 and 3.3 Hz, CH*-Leu), 2.53 (s, 3H, $CH_3$), 1.99 (ddd, 1H, J 13.7, 10.4, and 3.2 Hz, CH-Leu), 1.40-1.27 (m, 2H, $CH_2$-Led), 0.77 (d, 3H, J 6.4 Hz, $CH_3$-Leu), 0.27 (d, 3H, J 6.5 Hz, $CH_3$-Leu); $^{13}C$ NMR (75 MHz, $CDCl_3$): δ169.5 (C═O), 160.9 (C═O), 150.6 (C═N), 145.0 (C), 137.3 (C), 136.2 (CH), 136.1 (C-Trp), 127.2 (CH), 126.2 (CH), 123.5 (CH-Trp), 122.8 (CH-Trp), 120.3 (C), 119.9 (CH-Trp), 118.9 (CH-Trp), 111.1 (CH-Trp), 109.8 (C-Trp), 57.2 (C*-Trp), 50.7 (C*-Leu), 40.2 ($CH_2$-Leu), 27.1 ($CH_2$-Trp), 24.13 (CH-Leu), 23.3 ($CH_3$-Leu), 21.4 ($CH_3$), 19.7 ($CH_3$-Leu).

In an embodiment, the characterization of (1S,4R)-4-(1H-indol-3-yl)methyl)-1-isobutyl-8-methoxy-1,2-dihydro-6H-pyrazino[2,1-b]quinazoline-3,6(4H)-dione (41) is as follows: Yield: 36.6 mg, 5.83%; mp: 152.7-153.3° C. (MeOH);

$$[\alpha]_D^{30} = -222.22(c0.06;$$

$v_{max}$(KBr) 3184, 2956, 1666, 1617, 1464, 1247, and 776 $cm^{-1}$; $^1H$ NMR (300 MHz, DMSO-$d_6$): δ10.35 (s, 1H, NH-Trp), 7.69 (d, 1H, J 2.7 Hz, CH), 7.52 (d, 1H, J 8.9 Hz, CH-Trp), 7.38 (d, 1H, J 8.0 Hz, CH), 7.36 (dd, 1H, 7.9 and 4.0 Hz, CH), 7.31 (d, 1H, J 8.1 Hz, CH-Trp), 7.21 (s, 1H, NH-amide), 7.05 (t, 1H, J 7.1 Hz, CH-Trp), 6.87 (t, 1H, J 7.4 Hz, CH-Trp), 6.68 (d, 1H, J 2.3 Hz, CH-Trp), 5.56 (dd, 1H, J 5.1 and 3.1 Hz, CH*-Trp), 3.97 (s, 3H, O—$CH_3$), 3.68 (dd, 1H, J 14.8 and 3.0 Hz, $CH_2$-Trp), 3.60 (dd, 1H, J 14.9 and 5.3 Hz, $CH_2$-Trp), 2.77 (dd, 1H, J 8.6 and 3.8 Hz, CH*-Leu), 2.08-1.87 (m, 1H, CH-Leu), 1.58-1.26 (m, 2H, $CH_2$-Leu), 0.69 (d, J 6.5 Hz, CH-Leu), 0.37 (d, 3H, J 6.5 Hz, $CH_3$-Leu), $^{13}C$ NMR (75 MHz, DMSO-$d_6$): δ168.6 (C═O), 160.0 (C═O), 157.9 (C—O), 150.0 (C═N), 141.2 (C), 136.2 (C), 128.9 (CH), 127.1 (C-Trp), 124.3 (CH-Trp), 121.4 (CH-Trp), 120.7 (C), 118.8 (CH-Trp), 118.8 (CH), 117.9 (CH-Trp), 111.5 (CH-Trp), 108.2 (C-Trp), 57.3 (C-Trp), 55.7 ($CH_3$), 50.3 (C*-Leu), 39.3 ($CH_2$-Leu), 26.4 ($CH_2$-Trp), 23.6 (CH-Leu), 22.9 ($CH_3$-Leu), 20.9 ($CH_3$-Leu).

In an embodiment, the characterization of (1S,4R)-4-((1H-indol-3-yl)methyl)-1-isobutyl-1,2-dihydro-6H-pyrazino[1,2-α]pyrido[3,4-d]pyrimidine-3,6(4H)-dione (42) is as follows: Yield: 45.2 mg, 9.37%; mp: 115.3-116.6° C. (MeOH);

$$[\alpha]_D^{30} = -176.30\,(c0.043;$$

$CHCl_3$); $v_{max}$(KBr) 3265, 2956,1682, 1469, 1233, and 741 $cm^{-1}$; $^1H$ NMR (300 MHz, $CDCl_3$): δ9.05 (s, 1H, CH), 8.74 (d, 1H, J 5.2 Hz, CH), 8.14 (s, 1H, NH-Trp), 8.13 (d, J 4.9 Hz, CH), 7.45 (d, 1H, J 8.0 Hz, CH-Trp), 7.31 (d, 1H, J 8.2 Hz, CH-Trp), 7.15 (dt, 1H, J 7.6 and 0.8 Hz, CH-Trp), 6.97 (dt, 1H, J 7.6 and 0.8 Hz, CH-Trp), 6.66 (d, 1H, J 2.1 Hz, CH-Trp), 5.73 (s, 1H, NH-amide), 5.66 (dd, 1H, J 5.2 and 1.9 Hz, CH*-Trp), 3.79 (dd, 1H, J 15.1 and 2.8 Hz, $CH_2$-Trp), 3.63 (dd, 1H, J 15.1 and 5.3 Hz, CH-Trp), 2.75 (dd, 1H, J 9.6 and 3.3 Hz, CH*-Leu), 2.08-1.87 (m, 1H, CH-Leu), 1.45-1.28 (m, 2H, $CH_2$-Leu), 0.78 (d, J 6.3 Hz, $CH_3$-Leu), 0.30 (d, 3H, J 6.5 Hz, $CH_3$-Leu); $^{13}C$ NMR (75 MHz, $CDCl_3$): δ168.8 (C═O), 159.8 (C═O), 153.81 (C═N), 151.2 (CH), 146.4 (CH), 136.2 (C-Trp), 127.0 (C-Trp), 123.5 (CH-Trp), 123.0 (CH-Trp), 120.5 (CH-Trp), 118.7 (CH), 118.6 (CH-Trp), 111.3 (CH-Trp), 109.4 (C-Trp), 57.7 (C*-Trp), 50.9 (C*-Leu), 40.2 ($CH_2$-Leu), 27.0 ($CH_2$-Trp), 24.2 (CH-Leu) 23.3 (CH-Leu), 19.7 ($CH_3$-Leu).

In an embodiment, the characterization of (7R,10S)-7-(1H-indol-3-yl)methyl)-10-isobutyl-9,10-dihydro-5H-pyrazino[1,2-a]pyrido(2,3-d) pyrimidine-5,8(7H)-done (43) is as follows: Yield: 58.3 mg, 12.1%; mp: 111.3-111.5° C. (MeOH);

$$[\alpha]_D^{30} = -153.15(c0.037;$$

$v_{max}$ (KBr) 3295, 3067, 2915, 1682, 1600, 1470,770, and 697 $cm^{-1}$; $^1H$ NMR (300 MHz, $CDCl_3$): δ9.01 (d, 1H, J 4.6 Hz, CH), 8.71 (d, 1H, J 7.9 Hz, CH), 8.07 (s, 1H, NH-Trp), 7.54 (d, 1H, J 7.8 Hz, CH-Trp), 7.51 (dd, 1H, J 7.9 and 4.5 Hz, CH), 7.31 (d, 1H, J 8.2 Hz, CH-Trp), 7.15 (dt, 1H, J 7.6 and 0.8 Hz, CH-Trp), 7.01 (dt, 1H, J 7.6 and 0.8 Hz, CH-Trp), 6.61 (d, 1H, J 2.4 Hz, CH-Trp), 5.69 (s, 1H, NH-amide), 5.64 (dd, 1H, J 5.3 and 2.8 Hz, CH*-Trp), 3.81 (dd, 1H, J 15.1 and 2.6 Hz, $CH_2$-Trp), 3.61 (dd, 1H, J 15.0 and 5.3 Hz, $CH_2$-Trp); 2.76 (dd, 1H, J 10.4 and 3.1 Hz, CH*-Leu), 1.21-1.14 (m, 1H, CH-Leu), 1.05-0.98 (m, 2H, $CH_2$-Leu), 0.78 (d, J 6.5 Hz, $CH_3$-Leu), 0.22 (d, 3H, J 6.5 Hz, $CH_3$-Leu); $^{13}C$ NMR (75 MHz, $CDCl_3$): δ169.1 (C═O), 160.0 (C═O), 153.81 (C═N), 147.1 (CH), 138.6 (CH), 136.1 (C-Trp), 127.2 (C-Trp), 123.4 (CH-Trp), 121.1 (CH-Trp), 119.8 (CH), 118.4 (CH-Trp), 111.3 (CH-Trp), 109.4 (C-Trp), 57.5 (C*-Trp), 51.0 (C*-Leu), 40.2 ($CH_2$-Leu), 27.2 ($CH_2$-Trp), 24.3. (CH-Leu) 23.5 (CH-Leu), 19.6 ($CH_3$-Leu).

In an embodiment, the characterization of (1S,4R)-4-((1H-indol-2-yl)methyl)-1-isobutyl-9-(1-methyl-1H-tetrazol-5-yl)-1,2-dihydro-6H-pyrazino [2,1-b]quinazoline-3,6 (4H)-dione (44) is as follows: Yield: 5.8 mg, 1%; mp: 202.8-203.2° C. (MeOH);

$$[\alpha]_D^{30} = -125.68(c0.061; CHCl_3);$$

$v_{max}$(KBr) 3356, 3119, 3053, 1671, 1457, 1261, and 740 $cm^{-1}$; $^1H$ NMR (300 MHz, $CDCl_3$): δ8.47 (d, 1H. J 8.3 Hz, CH), 8.41 (d, 1H, J 1.1 Hz, CH), 8.27 (dd, 1H, J 8.3 and 1.5 Hz, CH), 8.10 (s, 1H, NH-Trp), 7.50 (d, 1H, J 8.0 Hz, CH-Trp), 7.30 (d, 1H, J 8.3 Hz, CH-Trp), 7.13 (t, 1H, J 7.6 Hz, CH-Trp), 6.98 (d, 1H, J 7.5 Hz, CH-Trp), 6.67 (d, 1H, J 2.3 Hz, CH-Trp), 5.75 (s, 1H, NH-amide), 5.68 (dd, 1H, J 5.1 and 2.8 Hz, CH*-Trp), 4.45 (s, 3H, $CH_3N$), 3.79 (dd, 1H, J 15.0 and 2.8 Hz, $CH_2$-Trp), 3.66 (dd, 1H, J 15.1 and 5.3 Hz, $CH_2$-Trp), 2.74 (dd, 1H, J 9.2 and 3.4 Hz, CH*-Leu), 2.09-1.96 (m, 1H, CH-Leu), 1.43-1.30 (m, 2H, $CH_2$-Leu), 0.76 (d, 3H, J 6.2 Hz, $CH_3$-Leu), 0.31 (d, 3H, J 6.4 Hz, $C_3$-Leu); NMR (75 MHz, $CDCl_3$): δ169.3 (C═O), 164.2 (C═N-Tetrazol), 160.5 (C═O), 152.35 (C═N), 147.4 (C), 136.1 (C-Trp), 133.2 (C-Ctriazole), 127.8 (CH), 127.1 (C-Trp), 125.7 (CH), 125.0 (CH), 123.6 (CH-Trp), 122.8 (CH-Trp), 121.2 (C), 120.4 (CH-Trp), 118.7 (CH-Trp), 111.2 (CH-Trp), 109.6 (C-Trp), 57.4 (CH*-Trp), 50.9 (CH*-Leu), 40.7 (CH-Leu), 39.7 ($CH_3$), 27.1 ($CH_2$-Trp), 24.2 ($CH_3$-Leu), 23.2 ($CH_3$-Leu), 19.9 ($CH_3$-Leu).

In an embodiment, the characterization of (6S,9R)-9-(1H-indol-3-yl)methyl)-6-isobutyl-6,7-dihydro-1H-pyrimido[5,4-d]pyrimidine-2,4,8,11 (3H,9H)-tetraone (45) is as follows: Yield: 11.6 mg, 2.3%; mp: 306-306.5° C. (MeOH);

$$[\alpha]_D^{30} = -226.7(c0.025; CHCl_3);$$

$v_{max}$(KBr) $cm^{-1}$; 3384, 2956, 1670, 1457, 1322, and 1095; $^1H$ NMR (300 MHz, $CDCl_3$): δ8.21 (s, 1H, NH-Trp), 7.65 (d, 1H, J 7.8 Hz, CH-Trp), 7.39 (d, 1H, J 8.0 Hz, CH-Trp), 7.22 (dd, J 8.1 and 1.1 Hz, CH-Trp), 7.18-7.12 (m, 1H, CH-Trp), 7.11 (d, 1H, 2.3 Hz, CH-Trp), 6.73 (s, 1H, NH-amide), 5.98 (s, 1H, NH-Ant), 5.96 (s, 1H, NH-Ant), 4.28 (m, 1H, CH*-Trp), 3.52 (dd, 1H, J 14.6 and 3.6 Hz, $CH_2$-Trp), 3.44 (m, 1H, CH*-Leu), 3.19 (dd, 1H, J 14.7 and 8.5 Hz, $CH_2$-Trp), 1.69 (m, 1H, CH-Leu), 1.54 (m, 2H, $CH_2$-Leu), 0.90 (d, J 6.1 Hz, $CH_3$-Leu), 0.76 (d, 3H, J 6.1 Hz, $CH_3$-Leu); $^{13}C$ NMR (75 MHz, $CDCl_3$): δ168.7 (C═O), 168.2 (C═O), 165.9 (C═O), 160.2 (C═O), 150.5 (C═N), 146.9 141.74 (C), 136.5 (C-Trp), 126.7 (C-Trp), 123.9 (CH-Trp), 122.8 (CH-Trp), 122.3 (C), 120.2 (CH-Trp), 118.8 (CH-Trp), 111.4 (CH-Trp), 109.3 (C-Trp), 54.7 (C*-Trp), 53.1 (C*-Leu), 42.1 ($CH_2$-Leu), 29.9 ($CH_2$-Trp), 24.0 (CH-Leu), 23.1. (CH-Leu), 20.8 ($CH_3$-Leu).

In an embodiment, the characterization of (1S,4R)-1,4-bis((1H-indol-3-yl)methyl)-1,2-dihydro-6H-pyrazino[2,1-b] quinazoline-3,6(4H)-dione (46) is as follows: Yield: 27.4 mg, 5.7%; er=99:0; mp: 177.4-178.2° C. (MeOH);

$$[\alpha]_D^{30} = -66.17(0.13; CHCl_3);$$

$v_{max}$ (KBr) 3404, 3060, 2923, 1681, 1597, 1455, 695 and 668 $cm^{-1}$; $^1H$ NMR (300 MHz, $CDCl_3$): δ8.41 (dd, 1H, J 8.0 and 1.3, CH), 8.10 (s, 1H, NH-Trp), 8.04 (s, 1H, NH-Trp), 7.82 (ddd, 1H, J 8.5, 7.2 and 1.5 Hz, CH), 7.66 (d, 1H, J 7.7 Hz, CH), 7.57 (ddd, 1H, J 8.1, 7.5 and 1.2 Hz, CH), 7.36 (d, 2H, J 8.1 Hz, CH-Trp), 7.34 (d, 2H, J 8.0 Hz, CH-Trp), 7.22 (ddd, 1H, J 8.1, 7.5 0.8 Hz, CH-Trp), 7.14 (t, 1H, J 7.3 Hz, CH-Trp), 7.08 (ddd, 1H, J 8.1, 7.5 0.8 Hz, CH-Trp), 6.80 (t, 1H J 7.3, CH-Trp), 6.65 (d, 1H J 2.3 Hz, CH-Trp), 6.42 (d, 1H J 1.9 Hz, CH-Trp), 5.68 (s, 1H, NH-amide), 5.66 (dd, 1H, J 7.8, 3.8 Hz, CH*-Trp), 3.73 (dd, 2.3 Hz, CH*-Trp), 3.67 (dd, 2H, J 18.1 and 3.7 Hz, $CH_2$-Trp), 3.11 (dd, 1H, J 11.0 and 3.4 Hz-CH2-Trp), 2.75 (dd, 15.1 and 11.1 Hz, $CH_2$-Trp); $^{13}C$ NMR (75 MHz, $CDCl_3$): δ159.6 (C═O), 161.7 (C═O), 154.6, (C═N), 146.2 (C), 136.2 (C-Trp), 135.9 (C-Trp), 134.9 (CH), 133.3 (CH), 131.4 (CH), 127.8 (CH), 127.5 (C-Trp), 127.3 (C-Trp), 123.9 (CH), 123.7 (CH), 122.4 (CH-Trp), 122.3 (CH-Trp), 121.6 (CH-Trp), 119.7 (C-Trp (2)), 118.2 (CH-Trp), 114.1 (CH-Trp), 111.4 (CH-Trp), 110.1 (C-Trp), 64.6 (CH*-Trp), 54.0 (CH*-Trp), 30.9 ($CH_2$-Trp), 25.1 ($CH_2$-Trp).

In the present disclosure, all reagents were from analytical grade. Dred pyridine and triphenylphosphite were purchased from Sigma (Sigma-Aldrich Co. Ltd., Gillinghan, UK). Anthranilic acids (47) and protected amino acids 48 and 50 were purchased from TCI (Tokyo Chemical Industry Co. Ltd., Chu-Ru, Tokyo, Japan). Column chromatography purifications were performed using flash silica Merck 60, 230-400 mesh (EMD Millipore corporation, Billerica, MA, USA) and preparative TLC was carried out on precoated plates Merck Kieselgel 60 $F_{254}$ (EMO Millipore corporation, Billerica, MA, USA), spots were visualized with UV light (Vilber Lourmat, Marne-la-Vallée, France). Melting points were measured in a Köfler microscope and are uncorrected.

Infrared spectra were recorded in a KBr microplate in a FTIR spectrometer Nicolet iS10 from Thermo Scientific (Waltham, MA, USA) with Smart OMNI-Transmission accessory (Software 188 OMNIC 8.3). $^1H$ and $^{13}C$ NMR spectra were recorded in $CDCl_3$ (Deutero GmbH, Kasteliaun, Germany) at room temperature unless otherwise mentioned on Bruker AMC instrument (Bruker Biosciences Corporation, Billerica, MA, USA), operating at 300 MHz for $^1H$ and 75 MHz for $^{13}C$). Carbons were assigned according to HSQC and or HMBC experiments. Optical rotation was measured at 25° C. using the ADP 410 polarimeter (Bellingham+Stanley Ltd., Tunbridge Wells, Kent, UK), using the emission wavelength of sodium lamp, concentrations are given in g/100 mL. High resolution mass spectra (HRMS) were measured on a Bruker FTMS APEX III mass spectrometer (Bruker Corporation, Billerica, MA, USA) recorded as ESI (Electrospray) made in Centro de Apolo Cientifico e Tecnolóxico á Investigation (CACTI, University of Vigo, Pontevendra, Spain). The purity of synthesized compounds was determined by reversed-phase LC with diode array detector (DAD) using C18 column (Kimetex®, 2.6 EV0 C18 100 Å, 250×4.6 mm), the mobile phase was methanol:water (50:50), and the flow rate was 1.0 ml/min. Enantiomeric ratio was determined by enantioselective LC (LCMS-2010EV, Shimadzu, Lisbon, Portugal), employing a system equipped with a chiral column (Lux® 5 μm Amylose-1, 250×4.6 mm) and UV-detection at 254 nm, mobile phase was hexane:EtOH (90:10) and the flow rate was 0.5 mL/min. for semipreparative chromatography, a HLPC system consisted of a Shimadzu LC-6AD pump with a 200 μL loop was used with an amylose tris-3,5-dimethylphenylcarbamate coated with Nucleosil (500 A, 7 m, 20%, w/w) packed into a stainless-steel (200 mm×7 mm ID size) column, prepared in the UFSCar laboratory[39A].

Antibacterial Activity

The present disclosure also relates to antibacterial activity of the compounds herein disclosed.)

In the present disclosure, two Gram-positive—*Staphylococcus aureus* ATCC 29213 and *Enterococcus faecalis* ATCC 29212—and two Gram-negative—*Escherichia coli* ATCC 25922 and *Pseudomonas aeruginosa* ATCC 27853—reference bacterial strains were used. When it was possible to determine a minimal inhibitory concentration (MIC) value for these strains, clinically relevant strains were also used. These included methicillin-resistant *S. aureus* (MRSA) 66/1, isolated from public buses, as well as a isolate sensitive to the most commonly used antibiotic families (*S. aureus* 40/61/24) and two vancomycin-resistant *Enterococcus* (VRE) strains isolated from river water, *E. faecalis* B3/101 and *E. faecalis* A5/102, which is sensitive to ampicillin. Frozen stocks of all strains were grown on Mueller-Hinton agar (MH-BioKar Diagnostics, Allone, France) at 37° C. for 24 h. All bacterial strains were sub-cultured on MH agar and incubated overnight at 37° C. before each assay, in order to obtain fresh cultures.

An initial screening of the antibacterial activity of the compounds was performed by the Kirby-Bauer disk diffusion method, as recommended by the Clinical and Laboratory Standards institute (CLSI). Briefly, sterile 6 mm blank paper disks (Oxoid, Basingstoke, England) impregnated with 15 μg of each compound were placed on inoculated MH agar plates. A blank disk with DMSO was used as a negative control. MH inoculated plates were incubated for 18-20 hours at 37° C. At the end of the incubation, the inhibition halos where measured. The minimal inhibitory concentration (MIC) was used to determine the antibacterial activity of each compound, in accordance with the recommendations of the CLSI. Two-fold serial dilutions of the compounds were prepared in Mueller-Hinton Broth 2 (MHB2-Sigma-Aldrich, St. Louis, MO, USA) within the concentration range of 0.062-64 μg/mL. Cefotaxime (CTX) ranging between 0.031-16 μg/mL was used as a control. Sterility and growth controls were included in each assay. Purity check and colony counts of the inoculum suspensions were also performed in order to ensure that the final inoculum density closely approximates the intended number ($5\times10^5$ CFU/mL). The MIC was determined as the lowest concentration at which no visible growth was observed. The minimal bactericidal concentration (MBC) was assessed by spreading 10 μL of culture collected from wells showing no visible growth on MH agar plates. The MBC was determined as the lowest concentration at which no colonies grew after 16-18 hours incubation at 37° C. These assays were performed in duplicate.

In order to evaluate the combined effect of the compounds and clinically relevant antimicrobial drugs, a screening was conducted using the disk diffusion method, as previously described. A set of antibiotic disks (Oxoid, Basingstoke, England) to which the isolates were resistant was selected: cefotaxime (CTX, 30 μg) for extended spectrum beta-lactamase-producer *E. coli* SA/2, oxacillin (OX, 1 μg) for *S. aureus* 66/1, and vancomycin (VA, 30 μg) for *E. faecalis* B3/101. Antibiotic disks alone (controls) and antibiotic disks impregnated with 15 μg of each compound were placed on MH agar plates seeded with the respective bacteria. Sterile 6 mm blank papers impregnated with 15 μg of each compound alone were also tested. A blank disk with DMSO was used as a negative control. MH inoculated plates were incubated for 18-20 hours at 37° C. Potential synergism was recorded when the halo of an antibiotic disk impregnated with a compound was greater than the halo of the antibiotic or compound-impregnated blank disk alone.

Therefore, an initial screening of the antibacterial activity of the compounds 10-37 against the above-mentioned different reference strains of Gram-positive bacteria, Gram-negative bacteria, as well as clinically relevant multidrug-resistant (MDR) strains was performed by the disk diffusion method. This primary assessment was followed by the determination of minimal inhibitory concentrations (MIC) of reference strains. For active compounds, this determination was also made for MDR strains. In the range of concentrations tested, none of the compounds was active against Gram-negative bacteria, and none of 10-25, 26, 33, 34 and 37 was active against any of the tested strains (results not shown). The results of antibacterial activity on Gram-positive strains regarding all other compounds are presented in Table 3.

TABLE 3

Antibacterial activity of quinazolinones 27-32, 35 and 36 on Gram-positive reference and clinically relevant strains.

| | *S. aureus* ATCC 29213 | | *S. aureus* 40/61/24 | | *S. aureus* 66/1 (MRSA) | | *E. faecalis* ATCC 29212 | | *E. faecalis* A5/102 (VRE) | | *E. faecalis* B3/101 (VRE) | |
|---|---|---|---|---|---|---|---|---|---|---|---|---|
| | MIC | MBC | MIC | MBC | MIC | MBC | MIC | MBC | MIC | MBC | MIC | MBC |
| 27 | 32 | >64 | 64 | >64 | >64 | >64 | 64 | >64 | 64 | >64 | >64 | >64 |
| 27a | >64 | >64 | ND | ND | ND | ND | >64 | >64 | ND | ND | ND | ND |
| 27b | >64 | >64 | ND | ND | ND | ND | >64 | >64 | ND | ND | ND | ND |
| 28 | 32 | >64 | 64 | >64 | >64 | >64 | 32 | >64 | 64 | >64 | >64 | >64 |
| 28b | >64 | ND | ND | ND | ND | ND | >64 | >64 | ND | ND | ND | ND |
| 29 | 16 | >64 | 64 | >64 | >64 | >64 | 32 | >64 | 64 | >64 | >64 | >64 |
| 30 | 16 | >64 | >64 | >64 | >64 | >64 | >64 | >64 | ND | ND | ND | ND |
| 31 | 4 | >64 | 8 | >64 | 8 | >64 | >64 | >64 | ND | ND | ND | ND |
| 31a | 4 | >64 | 4 | >64 | 4 | >64 | >64 | >64 | ND | ND | ND | ND |
| 31b | >64 | >64 | ND | ND | ND | ND | >64 | >64 | ND | ND | ND | ND |
| 32 | 4 | >64 | 8 | >64 | 8 | >64 | >64 | >64 | ND | ND | ND | ND |
| 35 | 16 | >64 | 64 | >64 | >64 | >64 | >64 | >64 | ND | ND | ND | ND |
| 36 | 16 | >64 | >64 | >64 | >64 | >64 | >64 | >64 | ND | ND | ND | ND |

MIC, minimal inhibitory concentration;
MBC, minimal bactericidal concentration;
VRE, vancomycin-resistant *Enterococcus*;
MRSA, methicillin-resistant *Staphylococcus aureus*;
ND, not determined.
MIC and MBC are expressed in μg/mL.

None of the derivatives exhibit antibacterial activity against Gram-negative bacteria, similarly to the described for the natural isolated neofiscalin A (2A). Regarding antimicrobial activity against Gram-positive bacteria, 27, 28, and 29 had an inhibitory effect on both *Enterococcus faecalis* ATCC 29212 and *Staphylococcus aureus* ATCC 29213 reference strains, while 30, 31, 32, 35, and 36 only showed an inhibitory effect on *S. aureus* ATCC 29213. The most effective compounds against *S. aureus reference strain were* 31 and 32, with MIC values of 4 μg/mL. All of those compounds presented a bacteriostatic activity, with minimal bactericidal concentrations (MBC) greater than 64 μg/mL.

Analog 29 was the most effective, with MIC values of 32 μg/mL and 16 μg/mL against *E. faecalis* ATCC 29212 and *S. aureus* ATCC 29213, respectively. When tested against vancomycin-resistant *Enterococcus* (VRE) that was sensitive to ampicillin, the MICs obtained for 27, 28 and 29 were higher than those obtained for the reference strain (64 μg/mL as opposed to 32 μg/mL). In the range of concentrations tested, ail these compounds were ineffective against *E. faecalis* B3/101, a VRE strain that was also resistant to ampicillin. Regarding *S. aureus,* 27, 28 and 29 inhibited the growth of the strain 40/61/24 (MIC, 64 μg/mL), which is sensitive to the most commonly used antibiotic families, but not of methicillin-resistant *S. aureus* (MRSA 66/1. More importantly, compounds 31 and 32 showed a greater inhibitory capacity on both sensitive (40/61/24) and methicillin-resistant *S. aureus* (66/1) strains, with MIC values of 8 μg/mL.

In an embodiment, the synergistic effects with vancomycin and oxacillin were evaluated for MDR strains, but no effect was found. These antibiotics are relevant in the treatment of infections caused by *Enterococcus* spp. and *Staphylococcus aureus*, respectively.

The compounds showed activity only for Gram-positive strains and, overall, this activity was greater for reference strains than for clinically relevant strains, whether MDR or not. Regarding Gram-positive strains, the range was not equal for all compounds, with a greater number of compounds being active against *S. aureus* than *E. faecalis*. Whereas for *E. faecalis* there appeared to exist an inverse relationship between compound activity and resistance against clinically important antibiotics, there was not a clear tendency for *S. aureus*. It would be interesting to further study the promising inhibitory effect of compounds 31 and 32 on MRSA. Noteworthy, the first series of compounds ($1^{st}$ approach) showed no relevant effect in the growth of non-malignant cells.

In an embodiment, in order to evaluate the in vitro activities, such as antibacterial, the most promising derivatives 27, 28, and 31, were obtained in milligram scale by semipreparative enantioselective liquid chromatography, employing a tris-3,5-dimethylphenylcarbamate amylose column with multiple injection in a 200 μL loop.

The analytical method presented good separation ($\alpha$>1.2) and resolution values (Rs>8) for all compounds to allow the scale-up to the preparative mode. The semipreparative separation was optimized by adjusting the sample volume from the analytical method. The optimized mobile phase of analytical system (hexane:EtOH, 90:10) was transferred without any modification to semipreparative mode and 254 was chosen as minimum wavelength absorption. The column diameter was enlarged to a scale-up factor of 3. The flow rate was increase from 0.5 to 2 mL/min, and the retention times were between 15 to 50 min. The loading effect in semipreparative mode was examined by keeping the concentration of the feed solution at the maximum (1.5 mg/mL) and by varying the volume (100 to 200 μL). The mobile phase composition, chromatograms, and chromatographic parameter are summarized in FIG. 8 at analytical and semipreparative scales.

The elution order, specific rotation, and enantiomeric ratio e.r) of resolved enantiomers were measured and the data is presented in Table 4. The e.r was greater than 97% for each enantiomer.

TABLE 4

| Elution order, specific rotation, and enantiomeric excess (e.r) of the resolved compound 27, 28, and 31 enantiomers. | | | |
|---|---|---|---|
| Enantiomer | Elution order | [α]D (c)[a] | e.r (%)[b] |
| (−)-27 (27a) | First order | −0.06 (0.08) | >99 |
| (+)-27 (27b) | Second order | +0.04 (0.10) | >99 |
| (−)-28 (28a) | First order | −0.08 (0.05) | >99 |
| (+)-28 (28b) | Second order | +0.22 (0.12) | >99 |
| (−)-31 (31a) | First order | −0.16 (0.03) | 97:3 |
| (+)-31 (31b) | Second order | +0.15 (0.03) | >99 |

[a]Specific rotation in methanol with c = concentration in g/ml.
[b]Enantiomeric ratio (e.r) determinated by enantioselective LC under condition.

The pure enantiomers of 27, 28, and 31 were evaluated for antibacterial and antifungal activity. Enantiomer 31a showed a MIC of 4 μg/mL for reference strain *S. aureus* ATCC. 29213, sensitive clinical isolate *S. aureus* 40/61/24, and methicillin-resistant strain *S. aureus* 66/1, while enantiomer 31b showed no effect (Table 3). Noteworthy, the derivatives showed higher potency than the natural product neofiscalin A (2), (tested by the group with the same conditions)[24,26]. None of the pure enantiomers was active against the fungi tested.

Regarding antibacterial activity, the structure-activity relationship (SAR) study suggested that the presence of a halogen atom at positions C-9 or C-11 plays a crucial role for this activity, since all the non-halogenated compounds were inactive against all the tested strains (FIG. 4). In fact, compounds containing chlorine atoms at one or both positions exhibited better antibacterial activity compared to those having bromine and iodine. Higher antibacterial activities were obtained when the halogen atom is present at both C-9 and C-11 positions compound 30, 31, 32 and 37) and/or the presence of longer side chains at C-1. The enantiopure compound 31a showed significant antibacterial effect against a resistant strain of *S. aureus* while its antipode (31b) did not. This emphasizes that configuration (1S,4R) is crucial for antibacterial activity of quinazolinone scaffold.

Antimalarial Activity

The present disclosure also relates to antimalarial activity of the compounds herein disclosed.

The principle of the in vitro susceptibility test to malaria is to assess the degree of development of parasites *P. falciparum* in the presence of different concentrations of the compounds. In this assay, *P. falciparum* 3D7, a CQ-susceptible strain, was used to evaluate the antimalarial activity of the 29 quinazolinones. Activity was described in terms of C50 (concentration that inhibits the growth of 50% of *P. falciparum* parasite present in the culture) for 14 compounds (Table 5). The remaining 15, exhibited non-appreciable antiparasitic activity, they fail to produce dose-response curves and/or displayed >75% survival at 10 μM (data not shown).

To evaluate the antimalarial potential of the pyrazino[2,1-b]quinazoline-3,6-dione scaffold, the following compounds were screened: compounds 10-17 ($1^{st}$ approach), having 4 types of stereoisomers; compounds 19, 21, 23, 25 and 26 ($2^{nd}$ approach), compounds 28, 29, 31, 32, 35-38 ($3^{rd}$ approach) and compounds 39-46 ($4^{th}$ approach).

it was observed that anti-isomers 1S, 4R, like compounds 12 (fiscalin B) and 16, exhibited the highest antimalarial activity while syn-isomers 1S, 4S were inactive (compounds 10 and 14) and syn-isomers 1R,4R had decreased activity (compounds 13 and 17). Furthermore, compounds in the $1^{st}$ approach (10-17) demonstrated that increasing the size of the C-1 substituent increased the antimalarial activity, for example, compound 16 with C-1 having an isobutyl the same position. Compounds 12, 13, 16, 17, and 31, preferably 12, 13, 16 and 31, showed the highest antimalarial activity against *P. falciparum* strain 307.

To further evaluate the effect of C-1 substituent on the activity, the compounds of the $2^{nd}$ approach (19, 21, 23, 25 and 26) was evaluated, and SAR indicates that a sulfur substituent at C-1 do not favor activity (compounds 21).

In the investigation of the $3^{rd}$ approach of compounds (28, 29, 31, 32, 35-38) with different substituents on A ring, only compound 31 having chlorine atom at position 9 and 11 showed favourable antimalarial activity with an $IC_{50}$ value of 0.2 μM (weaker than compounds 12 and 16), while other derivatives (substituted with Br or I) showed to be inactive.

For the $4^{th}$ approach of pyrazino[2,1-b]quinazoline-3,6-diones (39-46), isosteric substitutions with the nitrogen atom at different positions of ring A (positions (9, 10, 11), led to a decrease/inactivation of the antimalarial activity (compounds 42 and 43). Compounds 39 and 41 each bearing a hydroxy or methoxy group at position 9 of ring A also showed a decrease in activity. Contrary to other reports of febrifugine derivatives, compound 44 with a tetrazole group at position 10 also showed a weak activity against *P. falciparum*.

TABLE 5

| In vitro activity against *Plasmodium falciparum* 3D7 strain. *P. falciparum* (3D7) | | | |
|---|---|---|---|
| Compounds | $IC_{50}$ [μM] | Compound | $IC_{50}$ [μM] |
| 12 ($1^{st}$ approach) | 0.10 ± 0.02 | 31 ($3^{rd}$ approach) | 0.20 ± 0.14 |
| 13 ($1^{st}$ approach) | 0.15 ± 0.05 | 32 ($3^{rd}$ approach) | 1.51 ± 0.53 |
| 15 ($1^{st}$ approach) | 2.00 ± 0.32 | 38 ($3^{rd}$ approach) | 4.00 ± 0.02 |
| 16 ($1^{st}$ approach) | 0.05 ± 0.02 | 39 ($4^{th}$ approach) | 0.73 ± 0.07 |
| 17 ($1^{st}$ approach) | 0.47 ± 0.22 | 42 ($4^{th}$ approach) | 4.00 ± 0.02 |
| 26 ($2^{nd}$ approach) | 3.68 ± 0.62 | 43 ($4^{th}$ approach) | 3.76 ± 060 |
| 25 ($2^{nd}$ approach) | 4.18 ± 0.03 | 44 ($4^{th}$ approach) | 1.02 ± 0.27 |
| CQ (6)* | 15.08 ± 0.08 | | |

*the $IC_{50}$ value of CQ is in nM.

An important criterion in evaluating active antimalarial compounds is their cytotoxicity in mammalian host cells. Compounds that showed the lowest $IC_{50}$ values against *P. falciparum* (12, 16, and 31) were selected to evaluate their cytotoxicity. The cell lines used for in vitro cytotoxicity assay were the V79 from non-tumor cell line of Chinese hamster lung fibroblasts and CQ (6) was used as control. The results showed relatively low $LD_{50}$ values ($LD_{50}$ concentration that inhibits the growth of 50% of cells present in the culture) when compared to CQ (6) (Table 6). Nonetheless, the selectivity index (SI; calculated by $LD_{50}/IC_{50}$) for compounds 12, 16, and 31 were between 19-70 (Table 6) and within the acceptable safety range (SI values greater than 10 indicates that a compound has an acceptable therapeutic window for the development of antimalarial drugs).

In general, the higher the SI, the more promising as an anti-malarial are the compounds, due to its selective action against the parasite.

TABLE 6

| Cytotoxicity against mammalian cells of compounds 12, 16, and 31. | | | |
|---|---|---|---|
| Compounds | *P. falciparum* (3D7) $IC_{50}$ (μM) | Mammalian cells (V79) $DL_{50}$ (μM) | SI |
| 12 ($1^{st}$ approach) | 0.10 ± 0.02 | 1.91 ± 0.44 | 19 |
| 16 ($1^{st}$ approach) | 0.05 ± 0.02 | 1.78 ± 0.47 | 34 |

TABLE 6-continued

| Cytotoxicity against mammalian cells of compounds 12, 16, and 31. | | | |
|---|---|---|---|
| Compounds | *P. falciparum* (3D7) $IC_{50}$ (μM) | Mammalian cells (V79) $DL_{50}$ (μM) | SI |
| 31 (3rd approach) | 0.20 ± 0.14 | 14.00 ± 1.41 | 70 |
| CQ (6)* | 15.08 ± 0.80* | 167.00 ± 42.00 | 11074 |

*the $IC_{50}$ value of CQ is in nM;
SI—Selectivity Index;
The results of $IC_{50}$ and $LD_{50}$ are presented as mean ± standard deviation.

Figure 6:
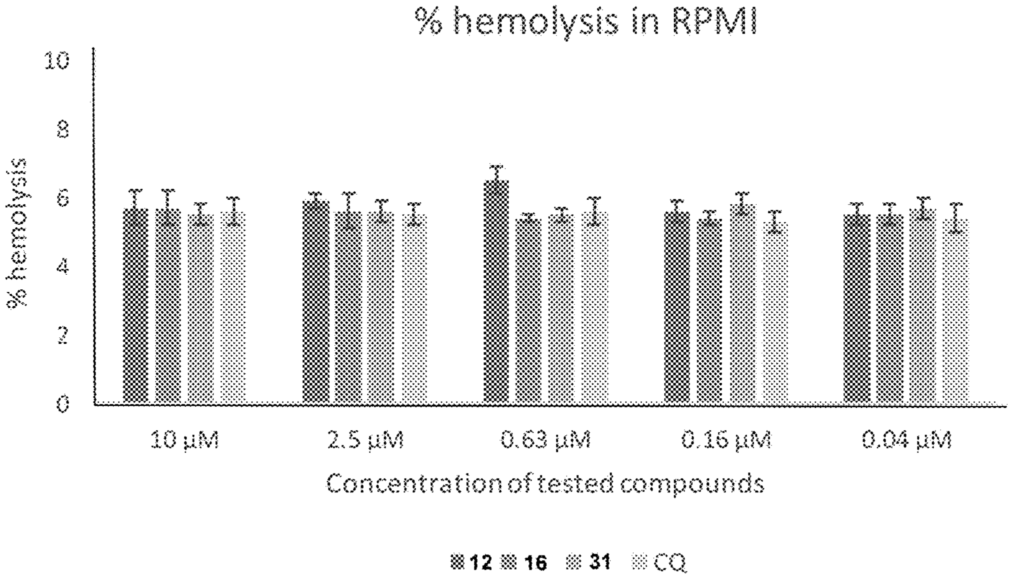
FIG. 6. Hemolysis of healthy erythrocytes in vitro induced by the compounds. The error bars represent the mean±standard deviation of % hemolysis of the compounds relative to the positive control obtained by action of Triton® X100.

In an embodiment, the evaluation of hemotoxicity in vitro was performed as follows. The in vitro hemolysis assay evaluates the release of hemoglobin in the medium (as an indicator of lysis of erythrocytes) after exposure to the test compounds. Drug-induced hemolysis can occur by two mechanisms; allergic hemolysis (toxicity caused by an immunological reaction in patients previously sensitized to a drug) and toxic hemolysis (direct toxicity of the drug, its metabolite or an excipient in the formulation) (26B). This test was intended to determine the potential toxic hemolytic effect of the hit compounds 12, 16, and 31 on healthy/non-parasitized erythrocytes (FIG. 6) The % of hemolysis induced by the compounds was also determined under standard culture conditions of *P. falciparum.*

The % of hemolysis of healthy erythrocytes induced by 12, 16, and 31 was lower than 6% (FIG. 6) and within the range of that of CQ (6). Compounds 12, 16, and 31 and CO (6) had no hemolytic activity at ≤10 μM. CO (6) is considered a non-hemolytic antimalarial drug in healthy human erythrocytes. Compounds 12, 16, and 31 did not present hemolytic activity, since the % hemolysis was <10% (% hemolysis >25% is considered as indicative of risk of hemolysis).

The assay of inhibition of the polymerization of hemozoin (β-hematin) in vitro was based on the protocol of Basilica et al. with some modifications and was carried out for compounds 12, 16, 31 and CO (6) by using a heroin solution (ferriprotoporphyrin IX chloride). In this assay, CO (6) was used as a positive control to evaluate the quality of the test since compound 6 binds to portions of hemozoin produced from the proteolytic process of hemoglobin in infected erythrocytes, thus interfering with hemozoin detoxification. Compounds, 12, 16, and 31 did not show to inhibit the polymerization of β-hematin in vitro (FIG. 5). Febrifuge (compound 9) significantly inhibits the formation of hemozoin required for the maturation of the parasite *Plasmodium* spp. in the trophozoite stage via axial ligand or π-π interaction to heme. Even though pyrazino[2,1-b]quinazoline-3,6-diones 12, 16, and 31 possess structure similarities with febrifugine compound 9), results suggested that the mechanism of action of these derivatives might be different from febrifugine (compound 9).

Recently, the cytoplasmic prolyl-tRNA synthetase of *P. falciparum* (PfcPRS), a member of the aminoacyl-tRNA synthetase (aaPS) family that drive protein translation, has been identified as the functional target of febrifugine (compound 9) and analogues, such as halofuginone (HF), a semisynthetic analogue in clinical trials. Therefore, a putative target for this approach of new antimalarials could be the PfcPRS and this hypothesis was explored with in silica studies. The computational docking study on inhibitory effect of prolyl-tRNA synthetase was carried out as follows. The binding affinity of twenty-nine pyrazinoquinazolinones (1017, 19, 21, 23, 25, 26, 28, 29, 31, 32, 35-46) to PRS enzyme target was predicted using computational docking AutodockTools. The positive controls were febrifugine (9, FF), HF, tetrahydroquinazolinone febrifugine (ThFF), and 6-fluorofebrifugine (6FFF) that were predicted as having high binding affinity to PRS, with docking scores between −9.3 and 9.7 kcal·mol$^{-1}$, whereas the negative control, CQ (6), revealed a docking score of −7.4 kcal·mol$^{-3}$. The most active antimalarials in vitro, compounds 12, 13, 16, 17 and 31, preferably 12, 13, 16 and 31, presented docking score from −9.1 to −11.4 kcal·mol$^{-1}$, predicted as forming complexes with PRS enzyme (Table 7, FIG. 7A).

TABLE 7

| Docking scores of the test compounds and controls onto 4ydq PRS binding site. | |
|---|---|
| Compounds | Docking scores (kcal · mol$^{-1}$) |
| 12 (1st approach) | −9.1 |
| 13 (1st approach) | −11.4 |
| 16 (1st approach) | −10.0 |
| 31 (3rd approach | −9.9 |
| Febrifugine (9, FF) | −9.5 |
| Halofugine (HF) | −9.3 |
| ThFF | −9.5 |
| 6FFF | −9.7 |
| CQ (6) | −7.4 |

Halofuginone (HF) is described as being mimetic of the enzyme substrates L-Pro and adenine-76 of tRNA, binding into the active site pockets simultaneously with ATP. Other quinazolinone-based compounds such as FF, 6FFF, and ThFF have also been described as specific for PfPRS when in the presence of the ATP analogue adenosine 5'-(β,γ-imido)triphosphate (AMPPNP). The structure of the ternary complex of PfPRS-AMPPNP-HF reveals hydrogen interactions with Thr359, Glu361, Arg390, Thr478, and His480, and π-π stacking interactions with Phe335 (FIG. 7B). Compound 13 fits the same binding pocket as HF, binding with some of the same residues as HF. The N atom of the indole ring forms hydrogen bonds with Thr478 and His480, and with AMPPNP phosphate groups; and the pyrazinoquinazolinone ring of 13 is mainly stabilized by hydrogen interactions with Glu361 and π-π stacking contacts with Phe335, but does not establish polar interactions with Arg390, suggesting chemical spaces available for additional modifications or derivatizations (FIGS. 7C and D). Compounds 12, 16, and 31 bind in the same positions in the PRS cavity but do not stablish hydrogen interactions with AMPPNP. Hydrogen interactions are formed with residues Glu361, Leu325, and Asn330; π-π stacking interactions are stablished with Phe335 and His331 (FIGS. 7E and F). The indole ring of 12, 16, and 31 dock into a lateral cavity flanked by His-331 that is not occupied by HF (FIG. 7F). The binding pose of 13, different from the binding poses of 12, 16, and 31, provides a hint on the relevance of chirality in the affinity of the binding to PRS target.

A series of halogenated and non-halogenated indolomethyl pyrazine [1,2-b]quinazoline-3,6-diones was designed and synthesized. Among all the obtained compounds, 31 and 32 exhibited a potent antibacterial activity against *S. aureus* strains, with MIC values of 4 μg/mL for a reference strain and MIC values of 8 μg/mL for a sensitive clinical isolate (*S. aureus* 40/61/24) and a methicillin-resistant strain (*S. aureus* 66/1). Isolation of the enantiomers of 31 revealed that only enantiomer (1S, 4R), 31a, was active, indicating that stereochemistry is vital for the referred activity. Comparing with the marine natural product neofiscalin A (2), an unexpected two-fold reduction in the MIC was observed. The presence of five stereocenters in neofiscalin A (2) makes its synthesis a challenge, while with this one-pot microwave-assisted multicomponent polycondensation of amino acids, highly active compounds were obtained in one single step.

Regarding antimalarial activity, the pyrazino[2,1-b]quinazoline-3,6-diene scaffold showed productive derivatives which demonstrated good antimalarial activity in vitro against *P. falciparum* strain 307. The compounds were not shown to be cytotoxic in vitro against non-tumor mammalian cells V79. These compounds did not show significant hemolytic activity in healthy human erythrocytes and also did not inhibit 3-hematin in vitro. These new antimalarial compounds were hypothesized to interact with the prolyl-tRNA similarly to halofuginone.

In the present disclosure, the antimalarial activity was also evaluated. Each compound was lyophilized and solubilized in DMSO (Sigma-Aldrich) to obtain a final concentration of 5 mM. Some intermediate dilutions were made to achieve the final concentration of 10 μM in the first well of the plate. Chloroquine (CQ Sigma-Aldrich) was prepared with RPMI-1640 (Invitrogen™) supplemented with AlbuMAXII (Invitrogen™) to obtain a final concentration of 10 μM.

In an embodiment, the culture of *P. falciparum* was carried out as follows. Laboratory-adapted *P. falciparum* 3D7 (chloroquine and mefloquine sensitive) were continuously cultured using the method of Trager and Jensen, with previously described modifications (Nogueira et at, 2010). Parasites were cultivated at 5% hematocrit, 37° C. and atmosphere with 5% of $CO_2$, human serum was replaced with 0.5% AlbuMAXII (Invitrogen™) in the culture medium. Synchronized cultures were obtained by treatments with a 5% (m/v) solution of D-sorbitol (Sigma-Aldrich).

In the present disclosure, the in vitro susceptibility assay of *P. falciparum* using SYBR Green I was carried out as follows. All compounds were screened for their in vitro antimalarial activity against chloroquine-susceptible (3D7) *P. falciparum* strain, using the Whole cell SYBR Green I assay as previously described with modifications. Briefly, early ring stage parasites (>80% of rings, 3% haematocrit and 1% parasitaemia) were tested in duplicate in a 96-well plate and incubated with the compounds for 48 h (37° C., 5% $CO_2$), parasite growth was assessed with SYBR Green I (Thermo Fisher Scientific). Each compound was tested in concentrations ranging from 10 to 0.001 μM. Fluorescence intensity was measured with a microplate reader with excitation and emission wavelengths of 485 and 535 nm, respectively, and analysed by nonlinear regression using GraphPad Prism 5 demo version to determine $IC_{50}$.

In the present disclosure, the cytotoxicity in vitro against mammalian cell was carried out as follows. Cytotoxicity was assessed on the mammalian cell line V79 (Chinese hamster lung), using an MTT based assay, as previously described [38B]. Tests were conducted in triplicate for each compound, at a range of concentrations (800 μM to 0.0512 μM), and with culture media containing 0.5% DMSO (no drug control); incubation time 24 h. Absorbance was read at 570 nm on a multi-mode microplate reader to produce a log dose-dependence curve. The $LD_{50}$ value for each compound was estimated by non-linear interpolation of the dose-dependence curve (GraphPad Software).

In the present disclosure, the evaluation of hemotoxicity in vitro was performed as follows. In a 96-flat bottom plate 3% HTC, 20 μL of 20% Triton X-100, and 20 μL of PBS or RPMIc in 2% DMSO was added. Compounds were tested in a 1:4 serial dilution in concentrations ranging from 10 μM to 0.04 μM. After the incubation of 60 minutes, the plate was centrifuged at 2000 rpm for 5 minutes. 100 mL of Supernatant was transferred to a flat bottom plate. The absorbance reading was made at 450 nm in a Mode (Triad, Dynex Technologies). Two independent tests were carried out in triplicate. The results are presented in the form of a percentage of hemolysis-% hemolysis, obtained by the following formula; % Hemolysis=ABS (sample)/abs (C+)×100. Whereas C+ is a Triton x-100 to 20% solution RPMIc.

In the present disclosure, the evaluation of inhibition of polymerization of hemozoin was performed as follows. 100 μL of a freshly prepared solution of heroin (ferriprotoporphyrin IX chloride; Sigma-Aldrich) 4 mM dissolved in 0.1 M NaOH (Sigma-Aldrich) was mixed with 50 μL of acetic acid (Sigma-Aldrich) and 50 μL of each tested compound. The mixture was incubated for 24 h at 37° C. in a U-bottom 96-well plate. Compounds were tested at the following doses: compounds 12 and 16 at 48.0 μM, 24.0 μM and 12.0 μM, compound 31 at 96.0 μM, 48.0 μM and 24.0 μM. After incubation, the resulting solution was spun down for 15 min at 4000 rpm, the supernatant discarded and the pellet was washed with 200 μL DMSO (3 washes) after an additional final wash with water (200 μL), the pellet was dissolved in 0.1 M NaOH (200 μL). 50 μL of the solution was transferred to a flat-bottom 96-well clean plate and mixed with 150 μl of water and absorption measured at 405 nm using a multi microplate reader plate reader (Triad, Dynex Technologies).

Figure 7:
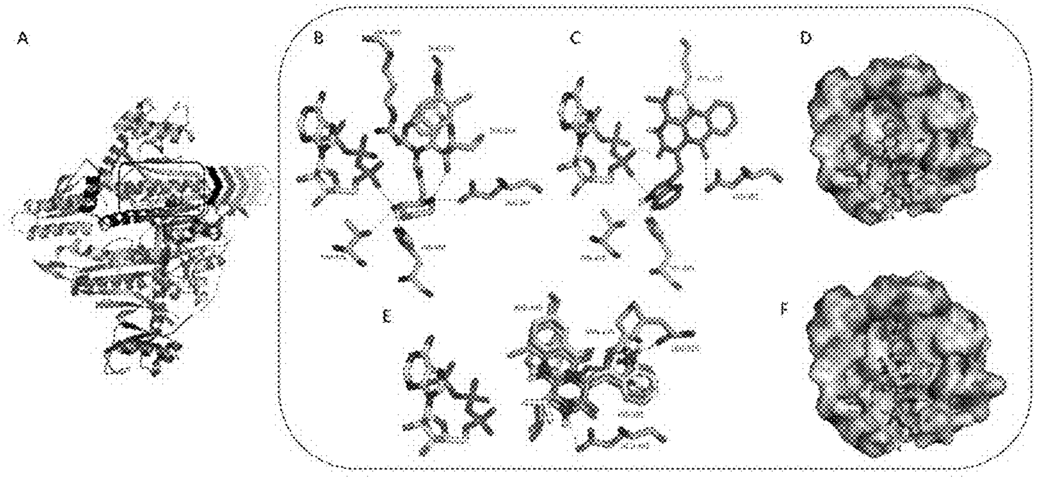
FIG. 7. (A) Ribbon representation of Prolyl-tRNA Synthetase (PRS) (PDB code: 4YDQ) with crystallographic HF and top scored test molecules 12, 13, 16, and 31. (B) Crystallographic HF; (C) 13, (E) 12, 16, and 31 docked into PRO active site. Relevant amino acids are represented in capped sticks and labeled. AMPPNP is represented as light gray sticks. Polar interactions are represented in light gray broken lines. Capped surface representation of PRS with docked conformations of (D) crystallographic HF and 13, and (F) crystallographic HF, 12, 16, and 31. Some PRS residues are omitted for simplification. Polar interactions are represented in light gray broken lines.
Figure 8A:
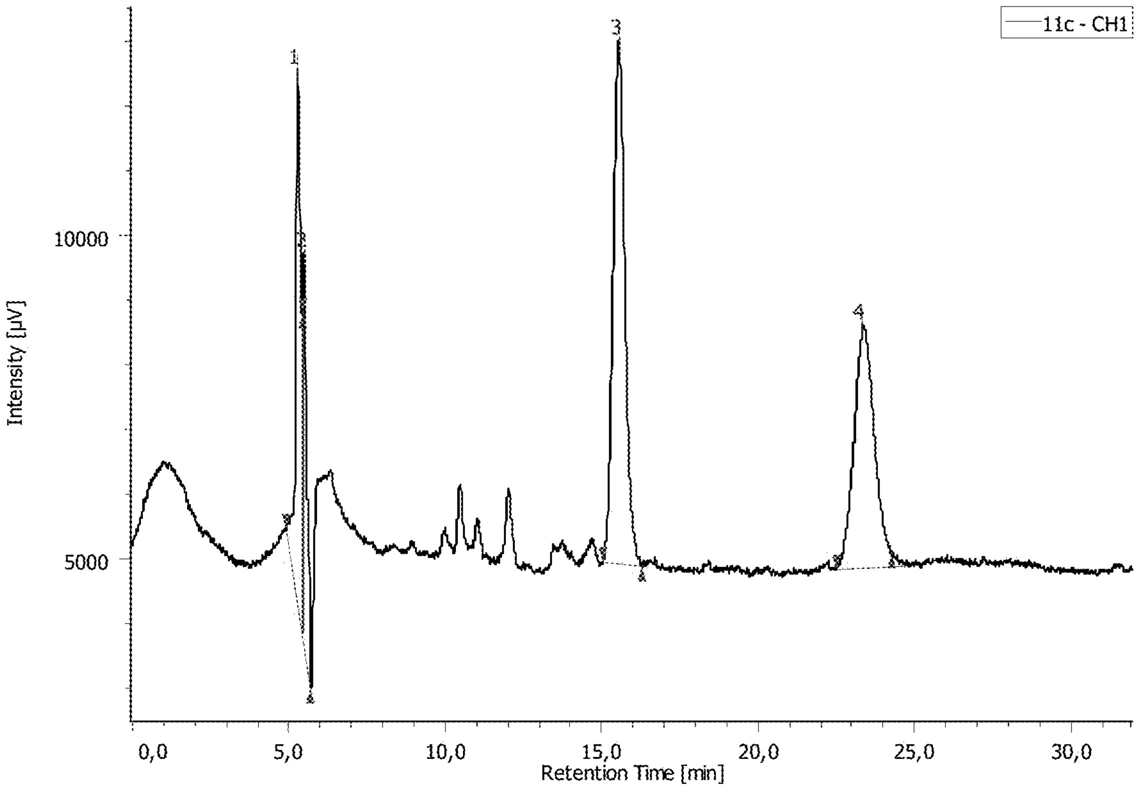
FIG. 8. Separation performance on the amylose tris-3,5 dimethylphenylcarbamate phase for compounds 27 wherein $k_1=1.95$, $\alpha=1.76$ Rs=8.43 (A analytical column; B semipreparative column), 28 wherein $k_1=2.64$, $\alpha=1.94$ Rs=8.15 (C analytical column; D semipreparative column), and 31 wherein $k_1$=5.60, α=1.75 Rs=11.69, wherein $k_1$=1.95, α=1.76 Rs=8.43 (E analytical column; F semipreparative column) [a] Flow rate: 0.5 mL/min, loop 20 μL, detection: 254 nm, column: Lux® 5 μm Amylose-1, (250×4.6 mm), mobile phase hexane:EtOH, 90:10. k: retention factor, α: enantioselective selectivity, Rs: resolution index; [b] Flow rate: 2 mL/min, loop 200 μL, loading ca. 1.5 mg/mL in hexane: EtOH (50:50), detection 254 nm, column: amylose tris-3,5-dimethylphenylcarbamate coated with Nucleosil (200 mm×7 mm); mobile phase hexane:EtOH, 90:10.
Figure 8B:
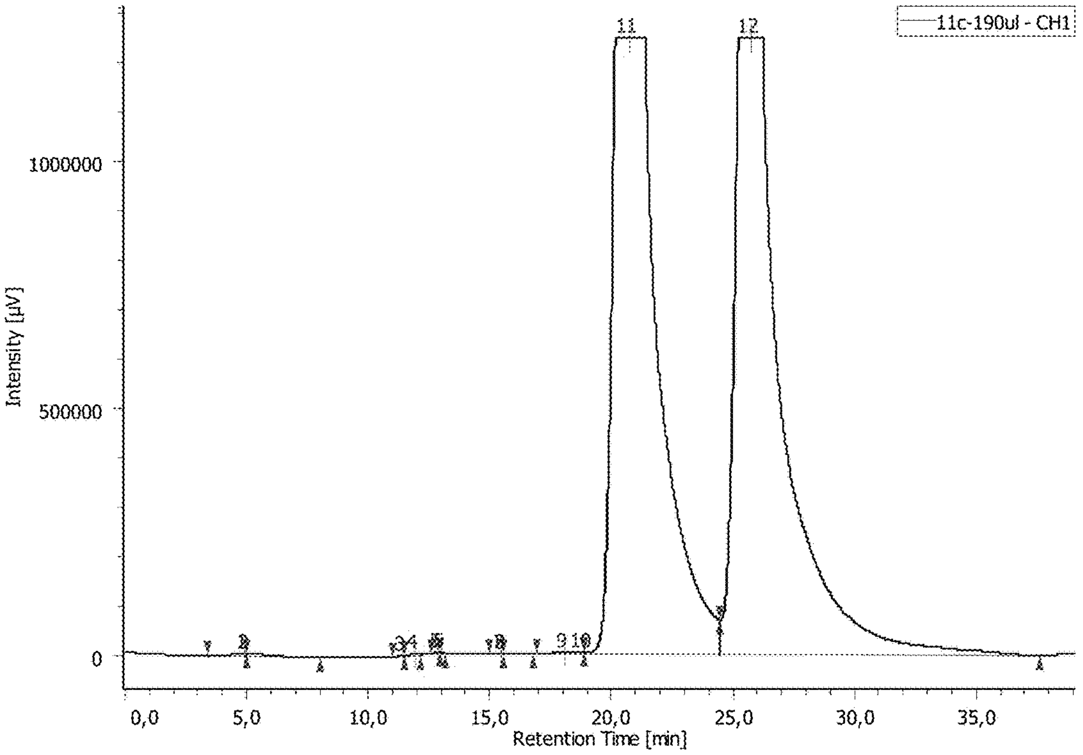
Figure 8C:
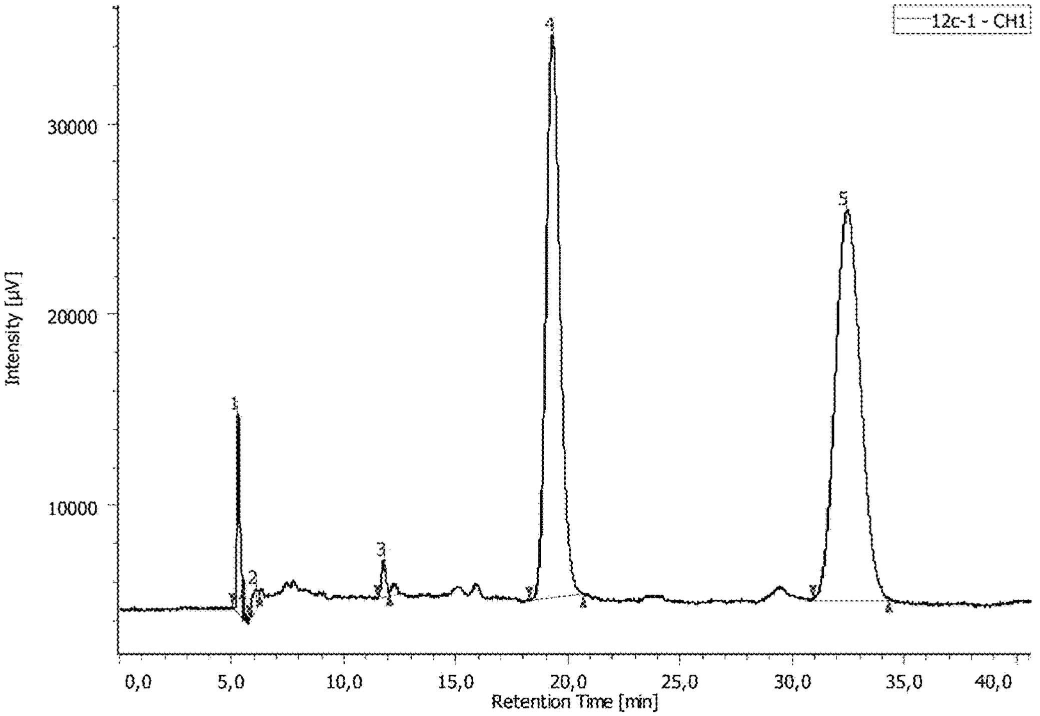
Figure 8D:
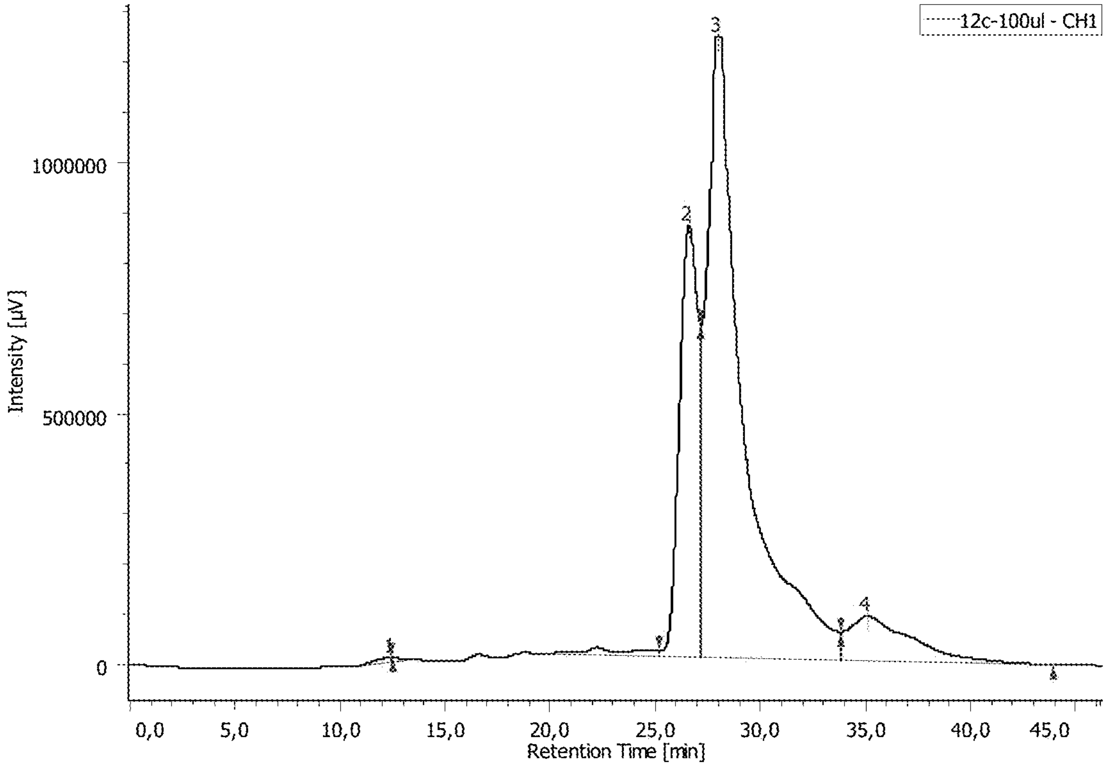
Figure 8E:
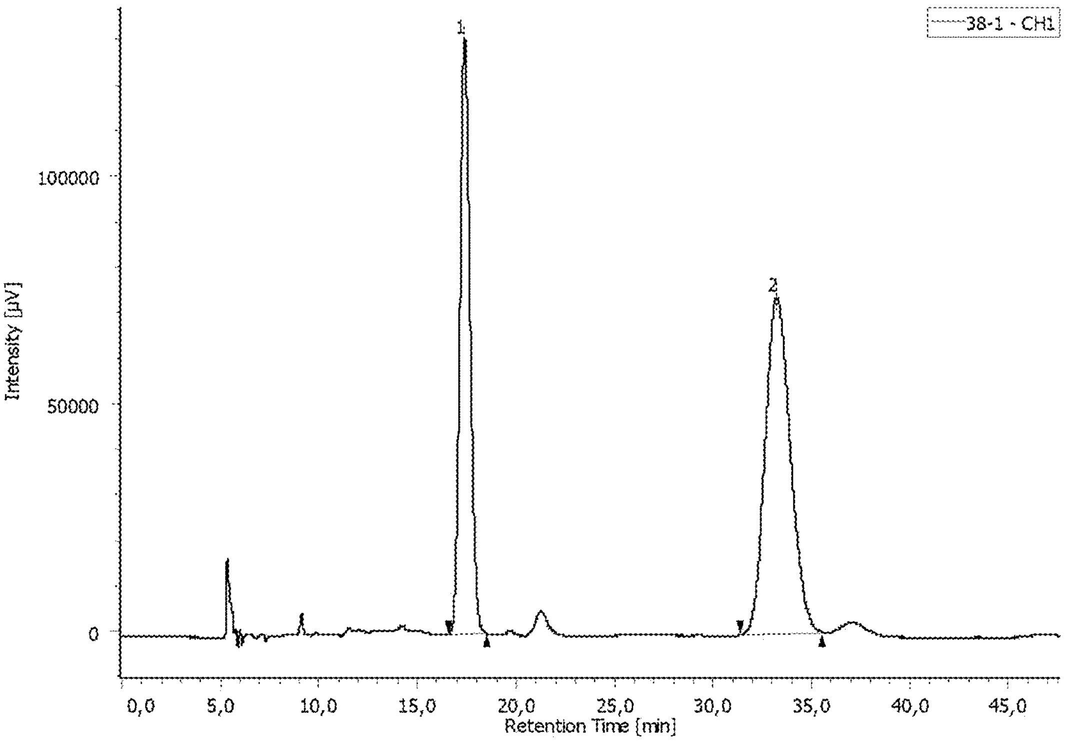
Figure 8F:
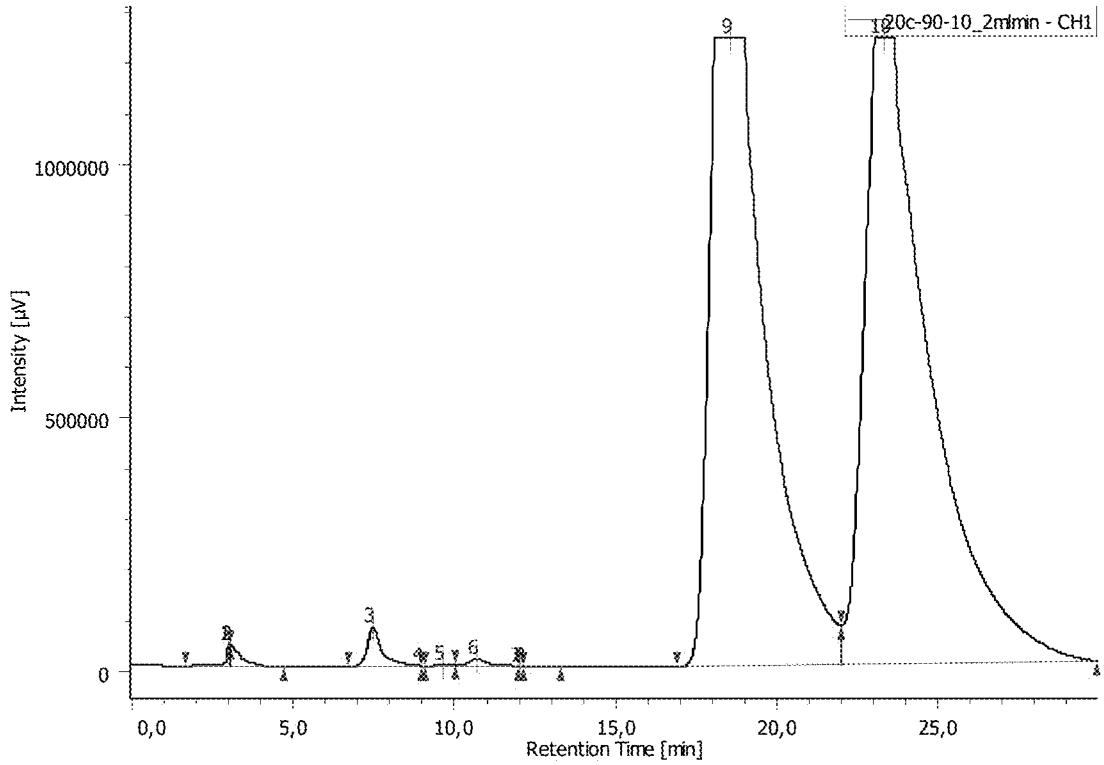

In the present disclosure, the crystal structure of Prolyl-tRNA Synthetase (PRS) (PDB code: 4YDQ), downloaded from the protein databank (PDB), was used. Structure files of 60 test molecule, four positive (halofuginone (HF), febrifugine (FF, 9), 6-fluorofebrifugine (6F-FF), and tetrahydro quinazolinone febrifugine (Th-FF)) and one negative (chloroquine, CQ 6) controls were created and minimized using the chemical structure drawing tool Hyperchem 7.5 (Hypercube, FL, USA) and prepared for docking using Autodock-Tools. Structure-based docking was carried out using AutoDock Vina (Molecular Graphics Lab, CA, USA). The active site was defined by a grid box (X: 19 Å; Y:14 Å; Z: 15 Å) drawn around the PRS crystallographic ligand HF. Default settings for small molecule-protein docking were used throughout the simulations. Top 9 poses were collected for each molecule and the lowest docking score value was associated with the more favorable binding conformation. PyMol1.3 (Schrödinger, NY, USA) was used for visual inspection of results and graphical representations. To validate the docking approach for the protein structure used, the respective co-crystallized inhibitor HF was docked to the active site using Autodock Vina (FIG. 7).

Compounds Synthetized and Tested in the Present Disclosure:

10

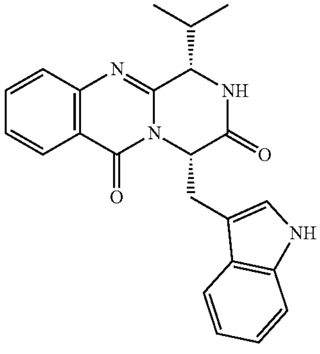

(1S,4S)-4-((1H-indol-3-yl)methyl)-1-isopropyl-1,2-dihydro-6H-pyrazino[2,1-b]quinazoline-3,6(4H)-dione -continued

28

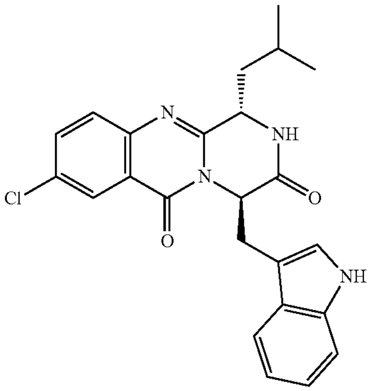

(1S,4R)-4-((1H-indol-3-yl)methyl)-8-chloro-1-isobutyl-1,2-dihydro-6H-pyrazino[2,1-b]quinazoline-3,6(4H)-dione

11

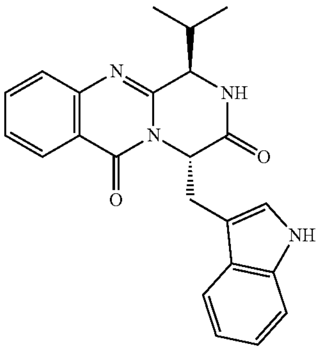

(1R,4S)-4-((1H-indol-3-yl)methyl)-1-isopropyl-1,2-dihydro-6H-pyrazino[2,1-b]quinazoline-3,6(4H)-dione

29

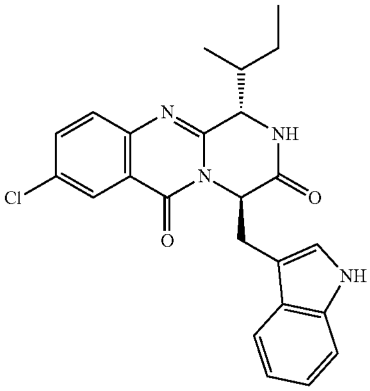

(1S,4R)-4-((1H-indol-3-yl)methyl)-1-((S)-sec-butyl)-8-chloro-1,2-dihydro-6H-pyrazino[2,1-b]quinazoline-3,6(4H)-dione -continued

12

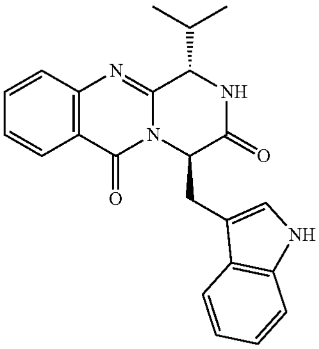

(1S,4R)-4-((1H-indol-3-yl)methyl)-1-isopropyl-1,2-dihydro-6H-pyrazino[2,1-b]quinazoline-3,6(4H)-dione

30

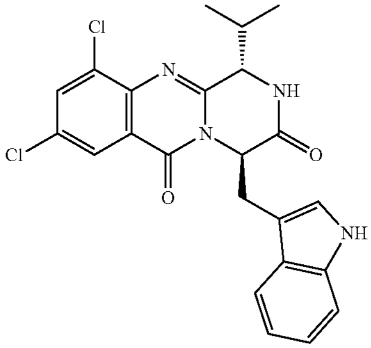

(1S,4R)-4-((1H-indol-3-yl)methyl)-8,10-dichloro-1-isopropyl-1,2-dihydro-6H-pyrazino[2,1-b]quinazoline-3,6(4H)-dione

13

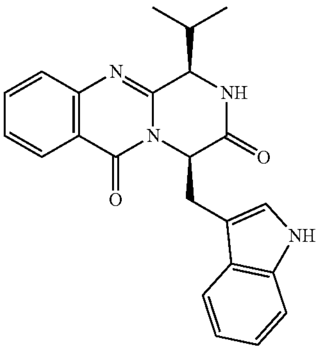

(1R,4R)-4-((1H-indol-3-yl)methyl)-1-isopropyl-1,2-dihydro-6H-pyrazino[2,1-b]quinazoline-3,6(4H)-dione

31

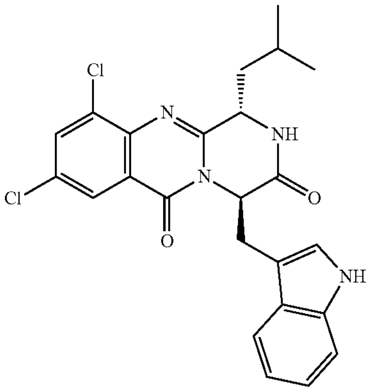

(1S,4R)-4-((1H-indol-3-yl)methyl)-8,10-dichloro-1-isobutyl-1,2-dihydro-6H-pyrazino[2,1-b]quinazoline-3,6(4H)-dione

14

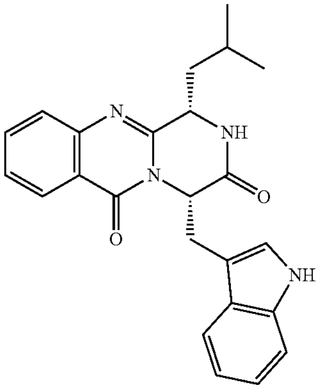

(1S,4S)-4-((1H-indol-3-yl)methyl)-1-isobutyl-1,2-dihydro-6H-pyrazino[2,1-b]quinazoline-3,6(4H)-dione

32

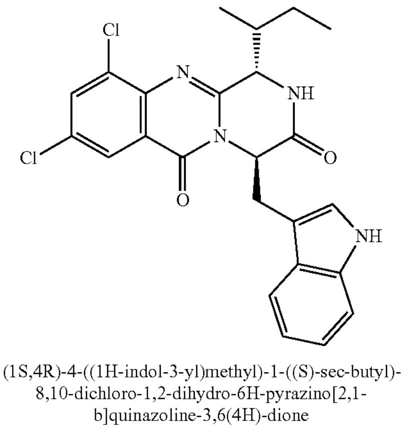

(1S,4R)-4-((1H-indol-3-yl)methyl)-1-((S)-sec-butyl)-8,10-dichloro-1,2-dihydro-6H-pyrazino[2,1-b]quinazoline-3,6(4H)-dione

15

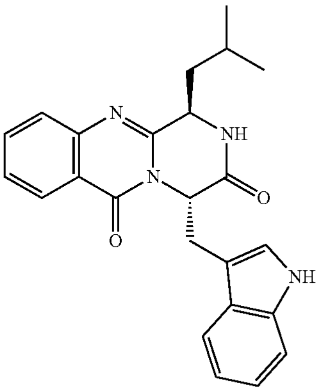

(1R,4S)-4-((1H-indol-3-yl)methyl)-1-isobutyl-1,2-dihydro-6H-pyrazino[2,1-b]quinazoline-3,6(4H)-dione

35

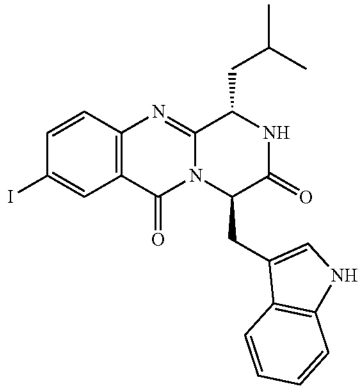

(1S,4R)-4-((1H-indol-3-yl)methyl)-8-iodo-1-isobutyl-1,2-dihydro-6H-pyrazino[2,1-b]quinazoline-3,6(4H)-dione

16

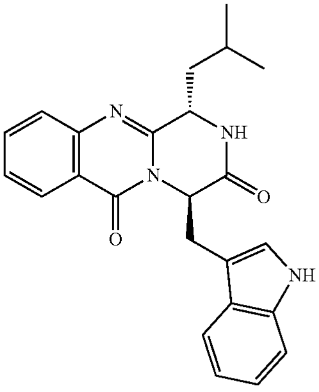

(1S,4R)-4-((1H-indol-3-yl)methyl)-1-isobutyl-1,2-dihydro-6H-pyrazino[2,1-b]quinazoline-3,6(4H)-dione -continued

36

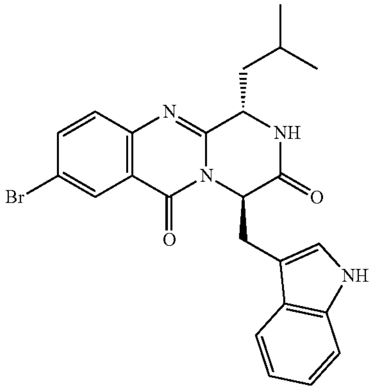

(1S,4R)-4-((1H-indol-3-yl)methyl)-8-bromo-1-isobutyl-1,2-dihydro-6H-pyrazino[2,1-b]quinazoline-3,6(4H)-dione

17

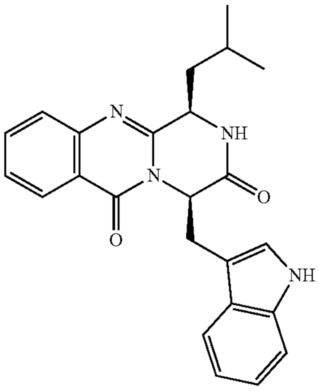

(1R,4R)-4-((1H-indol-3-yl)methyl)-1-isobutyl-1,2-dihydro-6H-pyrazino[2,1-b]quinazoline-3,6(4H)-dione

37

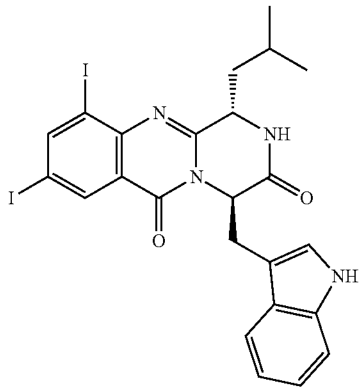

(1S,4R)-4-((1H-indol-3-yl)methyl)-8,10-diiodo-1-isobutyl-1,2-dihydro-6H-pyrazino[2,1-b]quinazoline-3,6(4H)-dione -continued

26

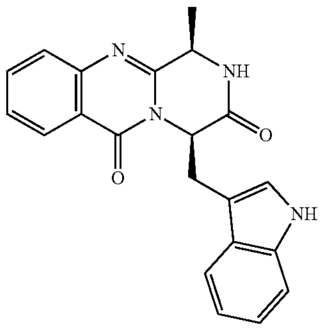

(1R,4R)-4-((1H-indol-3-yl)methyl)-1-methyl-1,2-dihydro-6H-pyrazino[2,1-b]quinazoline-3,6(4H)-dione

38

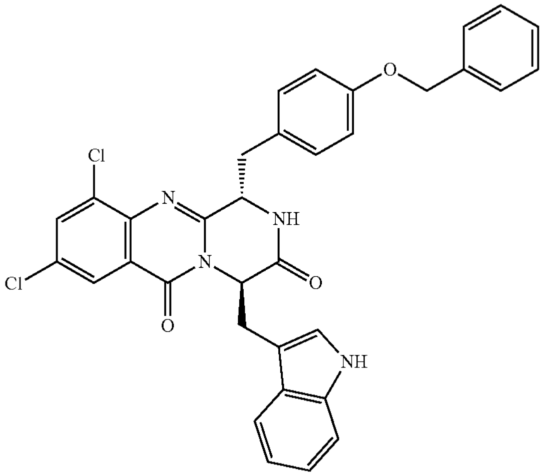

(1S,4R)-4-((1H-indol-3-yl)methyl)-1-(4-(benzyloxy)benzyl)-8,10-dichloro-1,2-dihydro-6H-pyrazino[2,1-b]quinazoline-3,6(4H)-dione

18

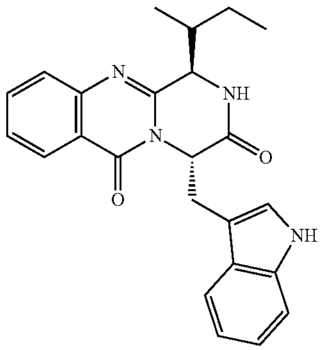

(1R,4S)-4-((1H-indol-3-yl)methyl)-1-((R)-sec-butyl)-1,2-dihydro-6H-pyrazino[2,1-b]quinazoline-3,6(4H)-dione -continued

39

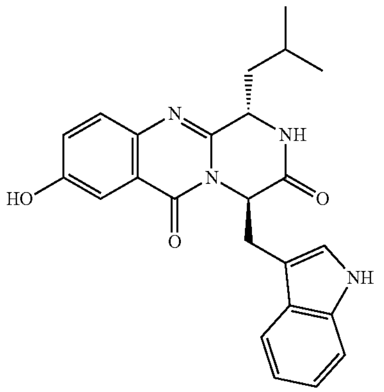

(1S,4R)-4-((1H-indol-3-yl)methyl)-8-hydroxy-1-isobutyl-1,2-dihydro-6H-pyrazino[2,1-b]quinazoline-3,6(4H)-dione

19

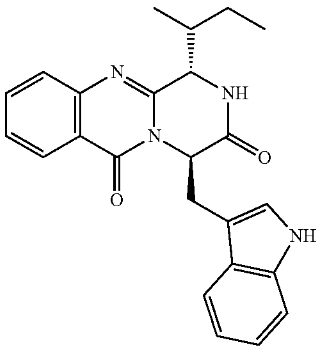

(1S,4R)-4-((1H-indol-3-yl)methyl)-1-((S)-sec-butyl)-1,2-dihydro-6H-pyrazino[2,1-b]quinazoline-3,6(4H)-dione

40

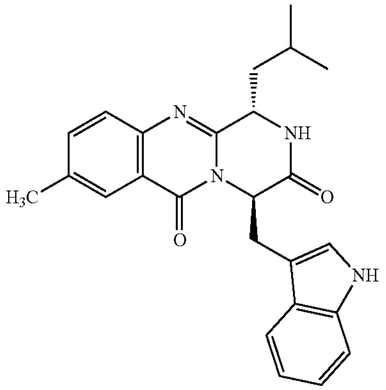

(1S,4R)-4-((1H-indol-3-yl)methyl)-1-isobutyl-8-methyl-1,2-dihydro-6H-pyrazino[2,1-b]quinazoline-3,6(4H)-dione -continued

20

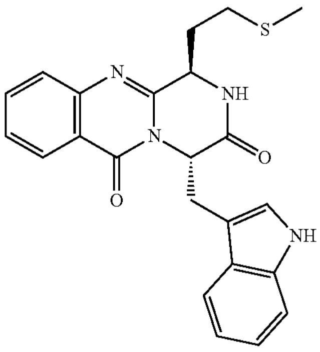

(1R,4S)-4-((1H-indol-3-yl)methyl)-1-(2-(methylthio)ethyl)-1,2-dihydro-6H-pyrazino[2,1-b]quinazoline-3,6(4H)-dione

41

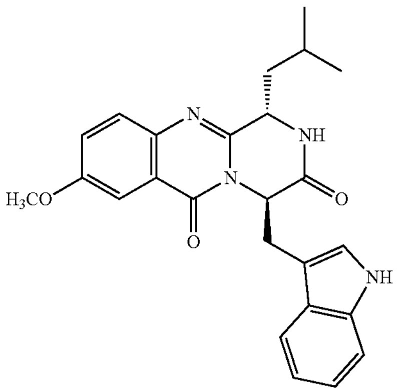

(1S,4R)-4-((1H-indol-3-yl)methyl)-1-isobutyl-8-methoxy-1,2-dihydro-6H-pyrazino[2,1-b]quinazoline-3,6(4H)-dione

21

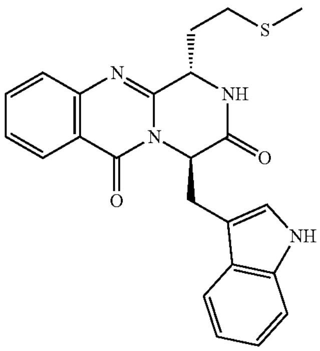

(1S,4R)-4-((1H-indol-3-yl)methyl)-1-(2-(methylthio)ethyl)-1,2-dihydro-6H-pyrazino[2,1-b]quinazoline-3,6(4H)-dione -continued

44

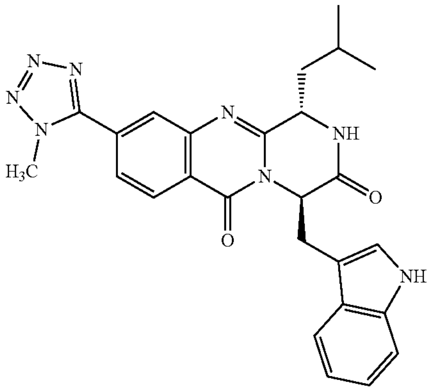

(1S,4R)-4-((1H-indol-3-yl)methyl)-1-isobutyl-9-(1-methyl-1H-tetrazol-5-yl)-1,2-dihydro-6H-pyrazino[2,1-b]quinazoline-3,6(4H)-dione

22

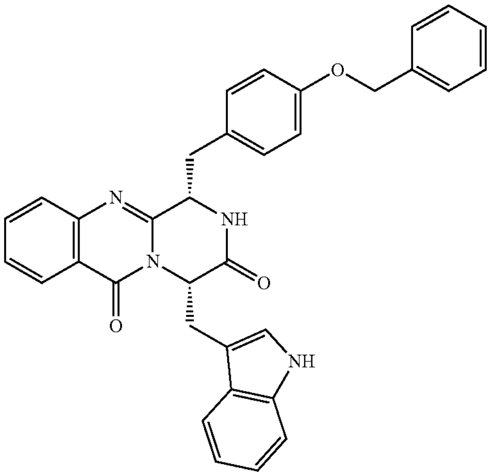

(1S,4S)-4-((1H-indol-3-yl)methyl)-1-(4-(benzyloxy)benzyl)-1,2-dihydro-6H-pyrazino[2,1-b]quinazoline-3,6(4H)-dione

42

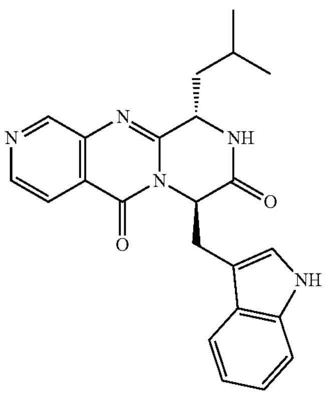

(1S,4R)-4-((1H-indol-3-yl)methyl)-1-isobutyl-1,2-dihydro-6H-pyrazino[1,2-a]pyrido[3,4-d]pyrimidine-3,6(4H)-dione -continued

23

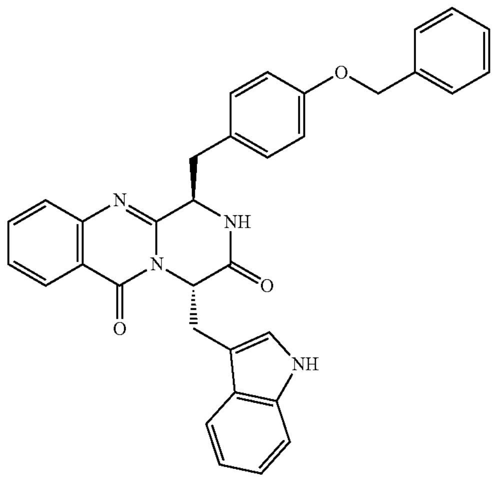

(1R,4S)-4-((1H-indol-3-yl)methyl)-1-(4-(benzyloxy)benzyl)-1,2-dihydro-6H-pyrazino[2,1-b]quinazoline-3,6(4H)-dione

43

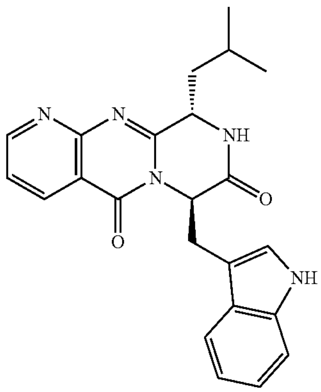

(7R,10S)-7-((1H-indol-3-yl)methyl)-10-isobutyl-9,10-dihydro-5H-pyrazino[1,2-a]pyrido[2,3-d]pyrimidine-5,8(7H)-dione

24

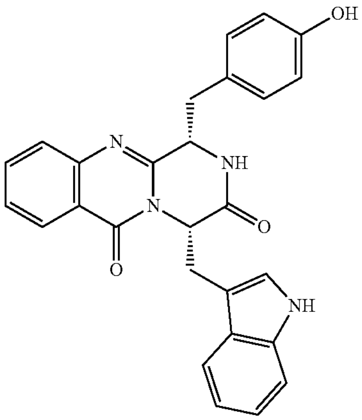

(1S,4S)-4-((1H-indol-3-yl)methyl)-1-(4-hydroxybenzyl)-1,2-dihydro-6H-pyrazino[2,1-b]quinazoline-3,6(4H)-dione -continued

45

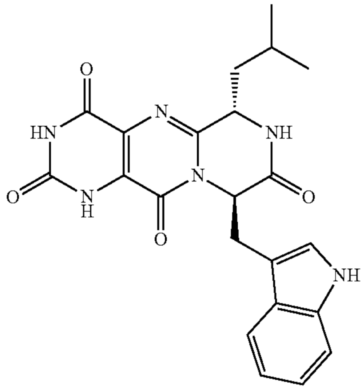

(6S,9R)-9-((1H-indol-3-yl)methyl)-6-isobutyl-6,7-dihydro-1H-pyrimido[5,4-d]pyrimidine-2,4,8,11(3H,9H)-tetraone

25

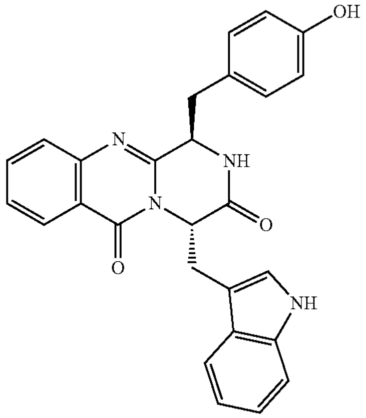

(1R,4S)-4-((1H-indol-3-yl)methyl)-1-(4-hydroxybenzyl)-1,2-dihydro-6H-pyrazino[2,1-b]quinazoline-3,6(4H)-dione

46

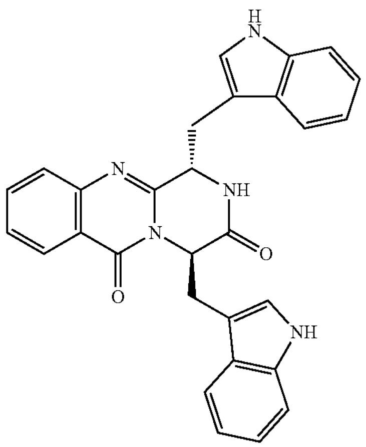

(1S,4R)-1,4-bis((1H-indol-3-yl)methyl)-1,2-dihydro-6H-pyrazino[2,1-b]quinazoline-3,6(4H)-dione -continued

27

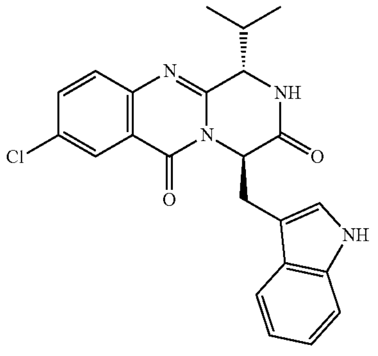

(1S,4R)-4-((1H-indol-3-yl)methyl)-8-chloro-1-isopropyl-1,2-dihydro-6H-pyrazino[2,1-b]quinazoline-3,6(4H)-dione

REFERENCES

1. Resende, D. I. S. P.; Boonpothong, P.; Sousa, E.; Kijjoa, A.; Pinto, M. M, M., Chemistry of the fumiquinazolines and structurally related alkaloids *Natural Product Reports* 2019, 36 (1), 7-34.
2. Bessa, L. J.; Buttachon, S.; Dethoup, T.; Martins, R.; Vasconcelos, V.; Kijjoa. A.; da Costa, P. M., Neofiscalin A and fiscalin C are potential novel indole alkaloid alternatives for the treatment of multidrug-resistant Gram-positive bacterial infections. *FEMS Microbial. Lett.* 2016, 363 (15), 1-5.
3. Long, S.; Resende, D. I. S. P.; Kijjoa, A.; Silva, A. M. S.; Pina, A., Fernández-Marcelo, T.; Vasconcelos, M. H.; Sousa, E.; Pinto, M. M. M., Antitumor Activity of Quinazolinone Alkaloids Inspired by Marine Natural Products. Marine Drugs 2018, 16 (8).
4. Long, S.; Resende, D. I. S. P.; Kijjoa, A.; Silva, A. M. S.; Fernandes, R.; Xavier, C. P. R.; Vasconcelos, M. H.; Sousa, E.; Pinto, M. M. M., Synthesis of New Proteomimetic Quinazolinone Alkaloids and Evaluation of Their Neuroprotective and Antitumor Effects. Molecules 2019, 24 (3), 534.
5. Gamo F J, Sanz L. M, Vidal J, De Cozar C, Alvarez E, Lavandera J L, Vanderwall D E, Green D V S, Kumar V, Hasan S et al: Thousands of chemical starting points for antimalarial lead identification. Nature 2010, 465(7296): 305-310.

The invention claimed is:

1. A compound of formula I:

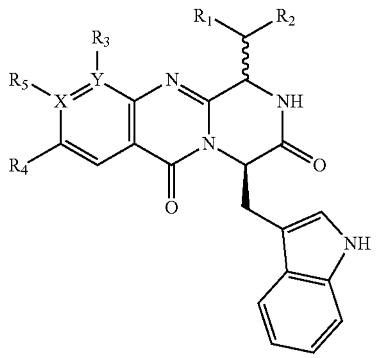

wherein $R_1$, $R_2$, $R_3$, $R_4$, $R_5$, X and Y are independently selected from each other;

$R_1$ and $R_2$ are selected from H or $CH_3$ or $CH(CH_3)_2$ or $CH_2CH_3$;

$R_3$ and $R_4$ are selected from H or Cl or Br or I or F or OH or $OCH_3$;

$R_5$ is H or

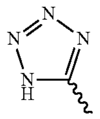

;

and

X and Y are selected from N or C;

or a pharmaceutically acceptable salt, or ester or solvate thereof;

provided that if X and Y are C then $R_4$ is different from H; or if X and Y are C then $R_4$ is H and $R_5$ is

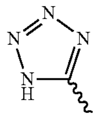

;

or if X is N then $R_5$ is absent, or if Y is N then $R_3$ is absent.

2. The compound of claim 1, wherein X and Y are C.

3. The compound of claim 1, wherein $R_1$ is H or $CH_3$.

4. The compound of claim 1, wherein $R_2$ is $CH_3$ or $CH(CH_3)_2$ or $CH_2CH_3$.

5. The compound of claim 1, wherein $R_3$ is H or Cl or I.

6. The compound of claim 1, wherein $R_4$ is Cl or I.

7. The compound of claim 1, wherein $R_5$ is H.

8. The compound of claim 1, wherein the compound is

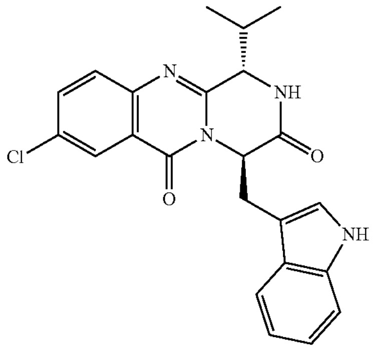

or,

-continued

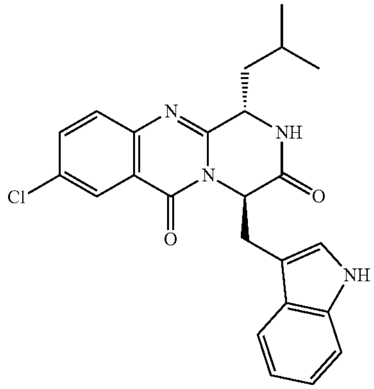

or,

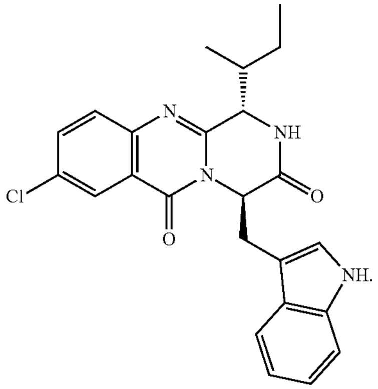

9. The compound of claim 1, wherein the compound is

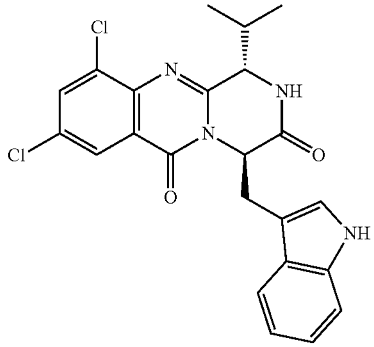

or,

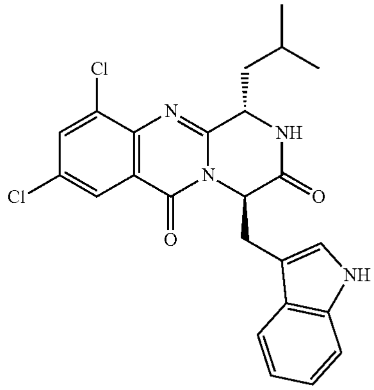

or,

-continued
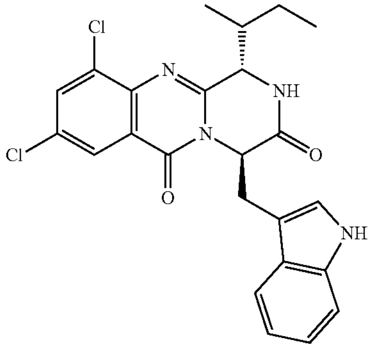
or,
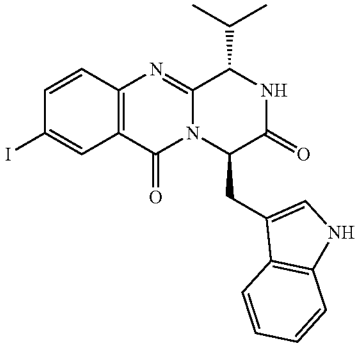
or,
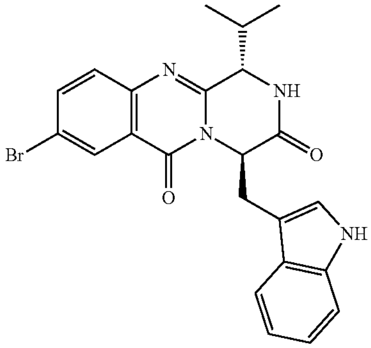
or,
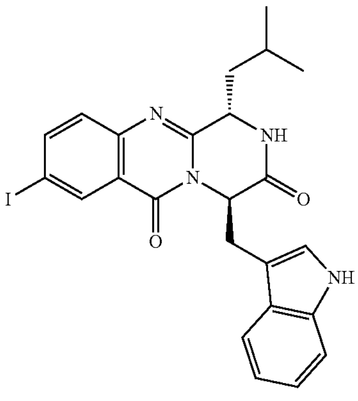
or,
-continued
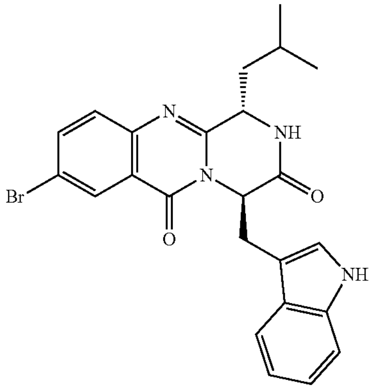
or,
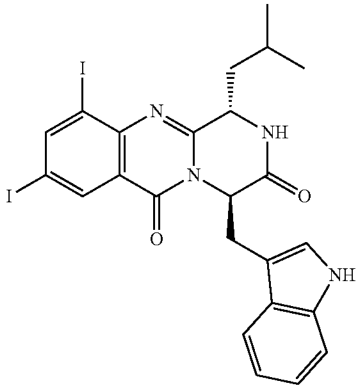
or,
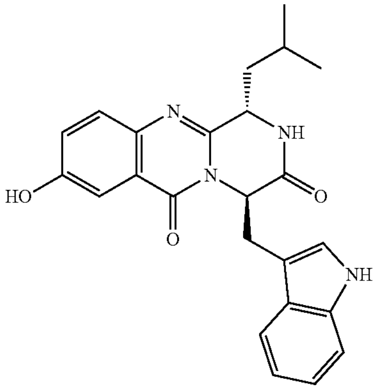
or,
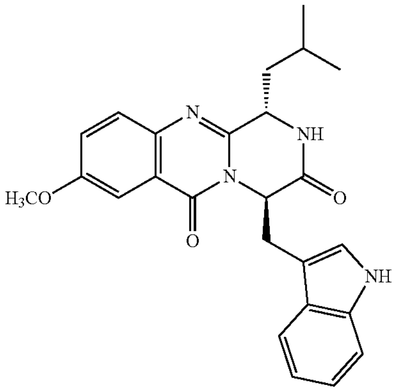
or, -continued

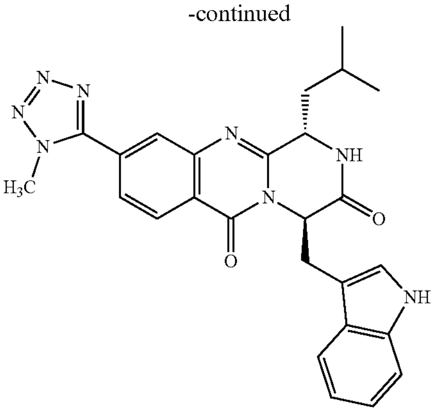

or,

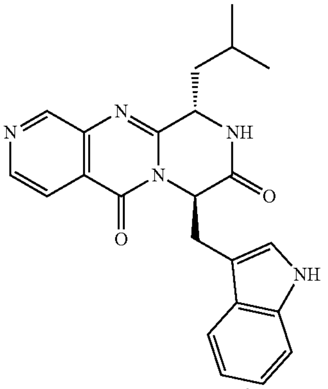

or,

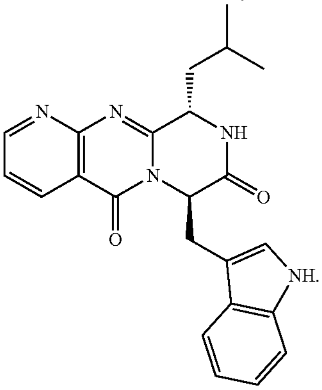

10. A compound of formula I:

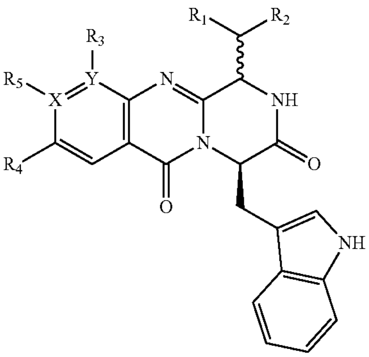

wherein $R_1$, $R_2$, $R_3$, $R_4$, $R_5$, X and Y are independently selected from each other;

$R_1$ and $R_2$ are selected from H or $CH_3$ or $CH(CH_3)_2$ or $CH_2CH_3$;

$R_3$ and $R_4$ are selected from H or Cl or Br or I or F or OH or $OCH_3$;

$R_5$ is H or

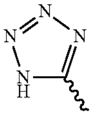

;

and

X and Y are selected from N or C;

or a pharmaceutically acceptable salt, or ester or solvate thereof;

provided that if X and Y are C then $R_4$ is different from H; or if X and Y are C then $R_4$ is H and $R_5$ is

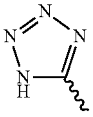

;

or if X is N then $R_5$ is absent, or if Y is N then $R_3$ is absent, wherein the compound is suitable for the treatment or prevention of bacterial infections.

11. The compound of claim 10, wherein the compound is suitable for the treatment or prevention of malaria, and wherein the compound is

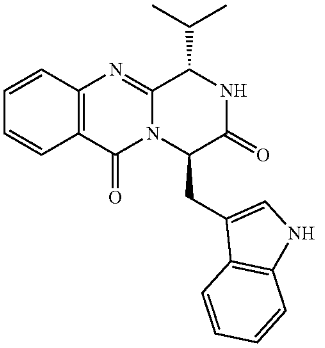

or,

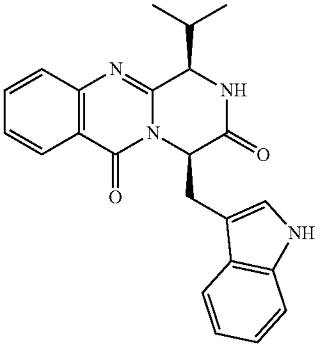

or,

-continued

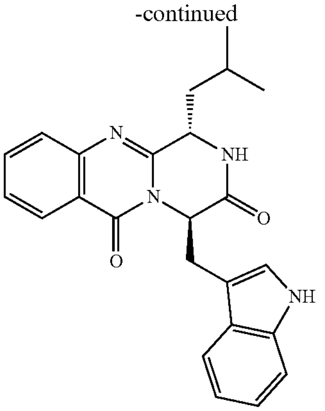

or,

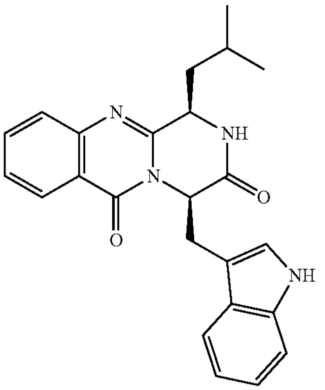

or,

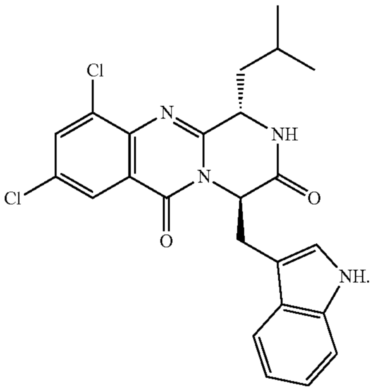 [SMILES: CC(C)C[C@@H]1NC(=O)[C@@H](Cc2c[nH]c3ccccc23)n2c1nc1c(Cl)cc(Cl)cc1c2=O]

12. The compound of claim 10, wherein the compound is suitable for the treatment of Gram-positive bacterial infections caused by *Staphylococcus* spp. and/or *Enterococcus* spp.

13. The compound of claim 12, wherein the compound is suitable for treatment of bacterial infections caused by *Staphylococcus aureus* and *Enterococcus faecalis*, wherein the compound is

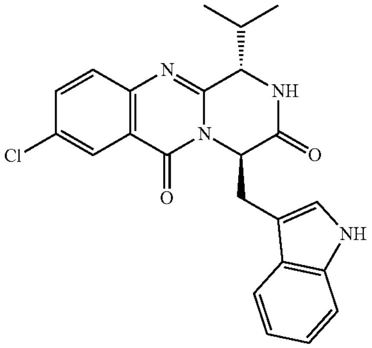

or,

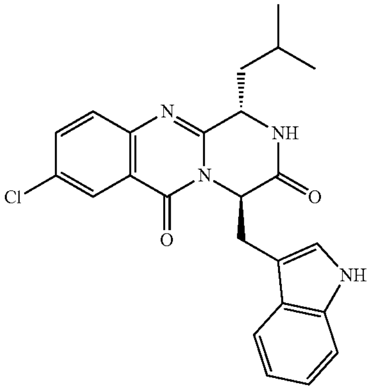

or,

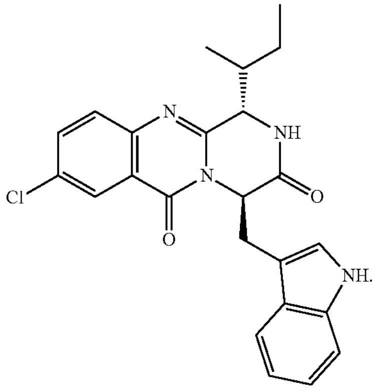

14. The compound of claim 12, wherein the compound is suitable for treatment of bacterial infections caused by *Staphylococcus aureus*, wherein the compound is

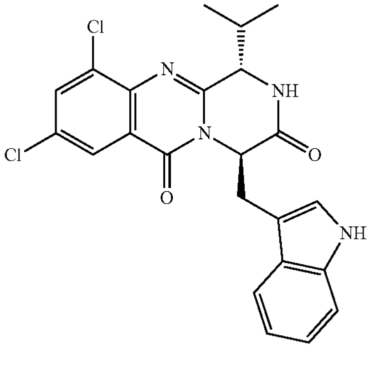

or,

-continued

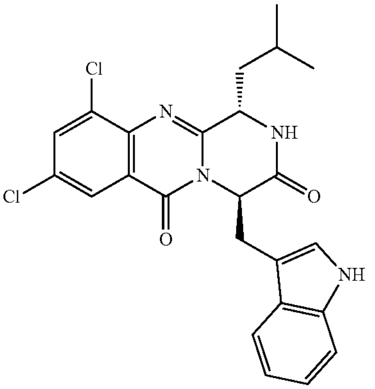

or,

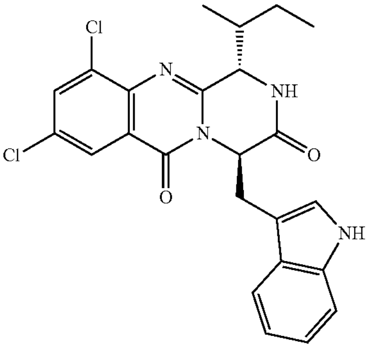

or,

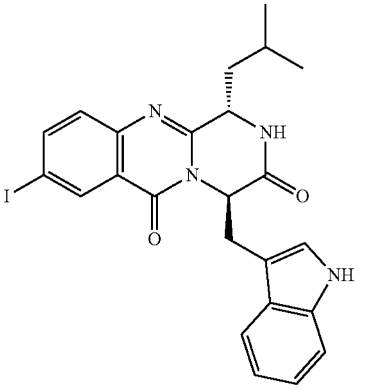

or,

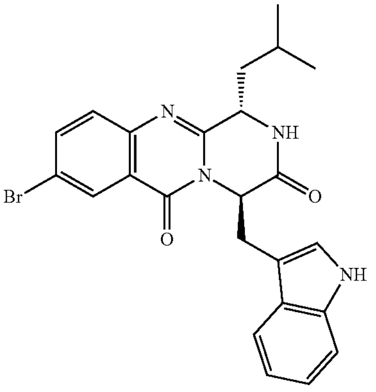

or,

-continued

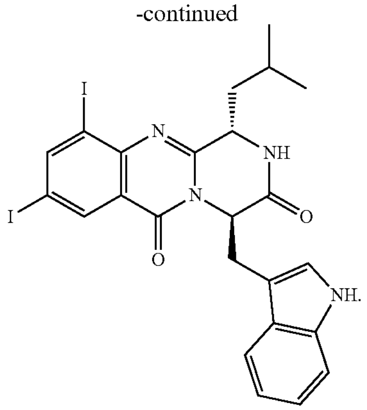

15. A composition comprising:

the compound of claim 1, wherein the compound is in a therapeutically effective amount;

and a pharmaceutically acceptable excipient.

16. The composition of claim 15, further comprising an antibiotic.

17. A method for treating or preventing malaria in a subject, the method comprising administering the compound of formula I to the subject,

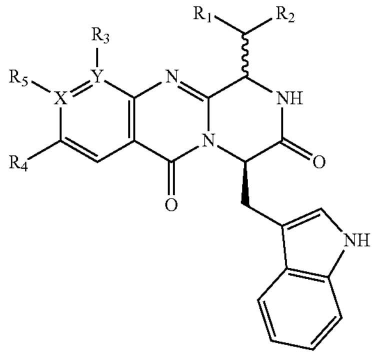

wherein $R_1$, $R_2$, $R_3$, $R_4$, $R_5$, X and Y are independently selected from each other;

$R_1$ and $R_2$ are selected from H or $CH_3$ or $CH(CH_3)_2$ or $CH_2CH_3$;

$R_3$ and $R_4$ are selected from H or Cl or Br or I or F or OH or $OCH_3$;

$R_5$ is H or

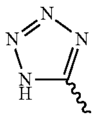

;

and

X and Y are selected from N or C;

or a pharmaceutically acceptable salt, or ester or solvate thereof;

provided that if X is N then $R_5$ is absent, or if Y is N then $R_3$ is absent.

* * * * *